US008377851B2

(12) United States Patent
Cotterill

(10) Patent No.: US 8,377,851 B2
(45) Date of Patent: Feb. 19, 2013

(54) METHOD OF ALTERING THE ALKALOID COMPOSITION IN POPPY PLANTS

(75) Inventor: Paul Cotterill, Latrobe (AU)

(73) Assignee: GlaxoSmithKline Australia Pty. Ltd., Boronia, Victoria (AU)

( * ) Notice: Subject to any disclaimer, the term of this patent is extended or adjusted under 35 U.S.C. 154(b) by 955 days.

(21) Appl. No.: 11/568,651

(22) PCT Filed: May 6, 2005

(86) PCT No.: PCT/AU2005/000651
§ 371 (c)(1),
(2), (4) Date: Aug. 28, 2008

(87) PCT Pub. No.: WO2005/107436
PCT Pub. Date: Nov. 17, 2005

(65) Prior Publication Data
US 2009/0075822 A1 Mar. 19, 2009

Related U.S. Application Data

(60) Provisional application No. 60/569,385, filed on Jun. 4, 2004.

(30) Foreign Application Priority Data

Jun. 4, 2004 (AU) .................................. 2004202517

(51) Int. Cl.
*A01N 43/40* (2006.01)
*A01N 37/08* (2006.01)
*C07D 489/00* (2006.01)
(52) U.S. Cl. ........ 504/260; 504/313; 504/320; 504/334; 546/44
(58) Field of Classification Search .................. 504/101, 504/260, 313, 320, 334; 546/44
See application file for complete search history.

(56) References Cited

U.S. PATENT DOCUMENTS

| 4,560,403 A | 12/1985 | Motojima et al. |
| 4,693,745 A | 9/1987 | Brunner |
| 4,909,835 A | 3/1990 | Tobler |
| 6,083,882 A | 7/2000 | Evans et al. |

FOREIGN PATENT DOCUMENTS

| AU | B-8369/91 | 3/1992 |
| AU | 646074 B2 * | 2/1994 |

OTHER PUBLICATIONS

Forbes, JJ, Poppies-Growth Regulators, 1984-85, Vegetables and Allied Crop Industries Annual Report, Department of Agriculture Tasmania, vol. 3, Part 1, pages Title page and 19-21.*
Rademacher, W., On the Mode of Action of Acylcylcohexanediones-A New Type of Plant Growth Retardant with Possible Relationships to Daminozide, 1993, Acta Horticulturae, Plant Growth Regulators, vol. 329, pp. 31-34.*

Trinexapac Data Sheet, Compendium of Pesticide Common Names,Datasheet [online]. Alanwood., 2011 [retrieved on May 20, 2011]. Retrieved from the Internet: <URL:http://www.alanwood.net/pesticides/index_cn_frame.html> p. 1.*
Brown et al., Phytochemistry, 47(5), pp. 679-687 (1998).
Facchini et al., Plant Physiology, American Society of Plant Physiologists, vol. 112, pp. 1669-1677 (1996).
Facchini et al., Phytochemistry, 49(2), pp. 481-490 (1998).
Huang, et al, "Distribution of morphinan and benzo[c]phenanthridine alkaloid gene transcript in *Papaver somniferum*," *Phytochemistry*(2000)53:555-564.
Facchini, et al, "Uncoupled defense gene expression and antimicrobial alkaloid accumulation in elicited opium poppy cell cultures," *Plant Physiology* (1996)111:687-697.
Millgate, et al., "Morphine-pathway block in top1 poppies," *Nature*(2004)431:413-414.
Opposition by Tasmanian Alkaloids Pty Ltd. Against European Patent Ep-B-1 755 373 granted in the name of Glaxosmithkline Australia PTY Ltd. (2 pages) Mar. 1, 2011; printed Jan. 18, 2011.
Geoff Johnson Dean Curriculum Vitae, March 1, 2011 ; printed Jan. 18, 2011.
Geoff Dean Email: SFS Strikes Again (Email Press Release) dated May 5, 2004.
Geoffrey Johnson Dean Declaration signed Dec. 15, 2010.
A.J. Fist: The Tasmanian Poppy Industry: A Case Study of the Application of Science and Technology; The Regional Institute 2001; pp. 1-8.
Heidrun, Halbwirth et al., Induction of Antimicrobial 3-Deoxyflavonoids in Pome Fruit Trees Controls Fire Blight Z Naturforsch [C] 58 (11-12):765-70, 2003.
Bruce Ross Mounster, Resume Mar. 1, 2011; printed Jan. 18, 2011.
Bruce Ross Mounster Declaration signed on Dec. 21, 2010.
Bruce Mounster: Short Poppy Shock Bonus; Tasmanian Country, Friday May 7, 2004.
Qian Y.L. et al., Influence of Trinexapac-Ethyl on Diamond Zoysiagrass in a Shade Environment; *Crop Sci.*, 39: 202-208 (1999).
Rademacher, Wilhelm: Growth Retardants: Effects on Gibberellin Biosynthesis and Other Metabolic Pathways; *Annu. Rev. Plant. Physiol. Plant Mol Biol.* 2000; vol. 51 pp. 501-531.
Rademacher, W.: On the Mode of Action of Acylcylcohexanediones — A New Type of Plant Growth Retardant with Possible Relationships to Daminozide; *Acta Horticulturae* 329, 1993 Plant Growth Regulators, pp. 31-34. Rajala a. et al.; Timing Applications of Growth Regulators to Alter Spring Cereal Development at High Latitudes; Agricultural and Food Science in Finland, vol. 11 (2002) 233-244.
Table of Contents from Annual Review of Plant Physiology and Plant Molecular Biology, vol. 51, 2000.
Vegetables and Allied Crop Industries Annual Report 1984-1985, vol. 3, part 1, pp. 19-21.

* cited by examiner

*Primary Examiner* — Johann Richter
*Assistant Examiner* — Andriae M Holt
(74) *Attorney, Agent, or Firm* — Nora L. Stein; Theodore R. Furman

(57) ABSTRACT

The method of altering the alkaloid composition of a poppy plant comprising the step of applying an effective amount of acylcyclohexanedione compound or agriculturally acceptable salt thereof to said poppy plant or locus thereof. Further, the present invention also provides the method of altering the alkaloid composition of a poppy plant comprising the step of applying an effective amount of methyl jasmonate or agriculturally acceptable salt thereof to said poppy plant or locus thereof.

8 Claims, 1 Drawing Sheet

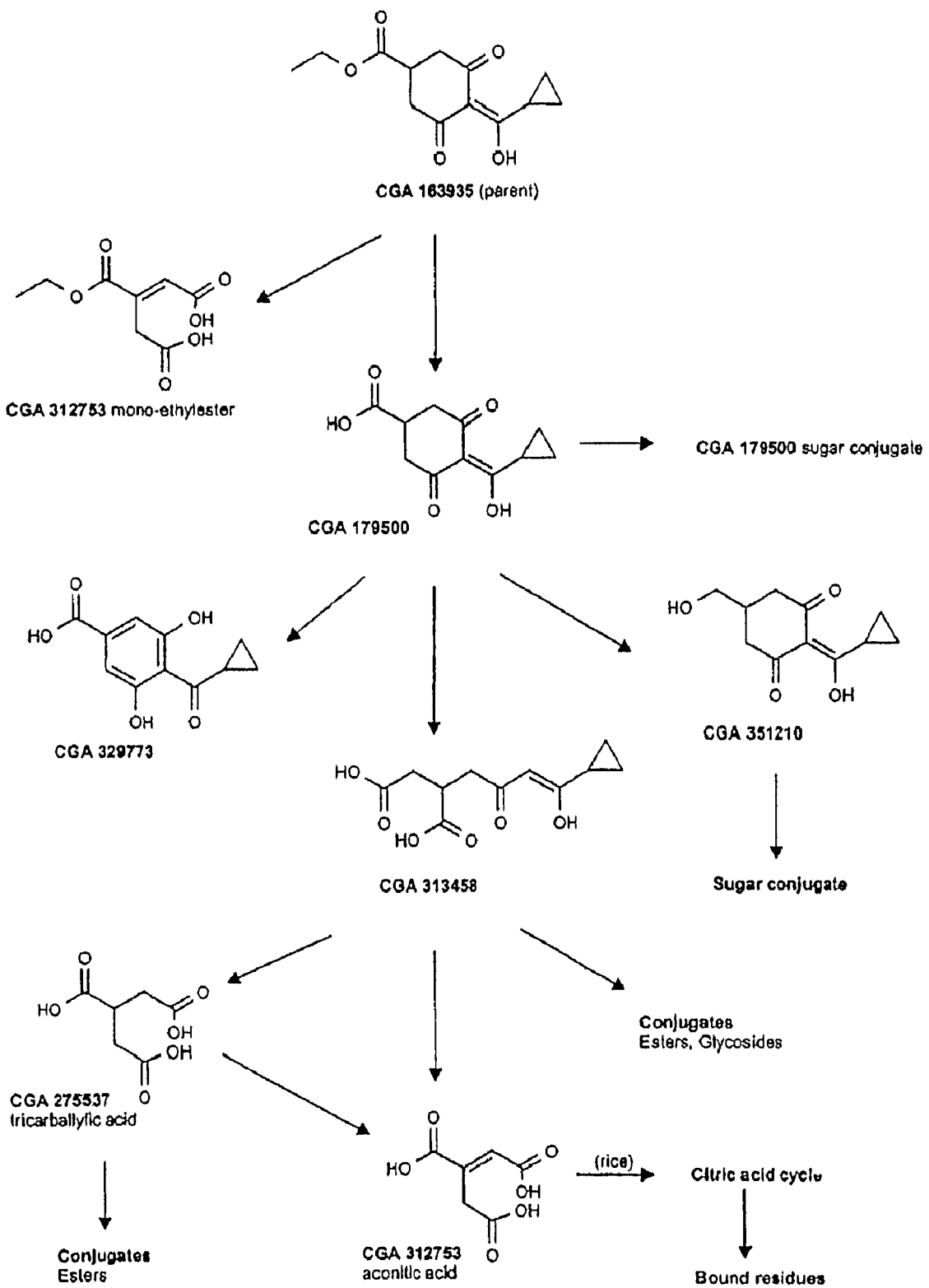

METHOD OF ALTERING THE ALKALOID COMPOSITION IN POPPY PLANTS

This application is a §371 national phase entry of International Application No. PCT/AU2005/000651, filed May 6, 2005 which claims priority to U.S. provisional U.S. Ser. No. 60/569,385 filed Jun. 4, 2004 and international patent application AU2004/202517 filed Jun. 4, 2004.

FIELD OF THE INVENTION

The present invention relates to the field of improved production of alkaloids from poppy plants. More particularly, the present invention relates to the application of certain compounds, including cyclohexanedione compounds, to poppy plants and/or loci in order to alter alkaloid composition.

BACKGROUND OF THE INVENTION

The opium or oil poppy, *Papaver somniferum*, is an erect annual plant which is cropped in order to produce alkaloids such as morphine, thebaine, oripavine, codeine, pseudomorphine and the like. Alkaloids are extracted from the poppy capsules of *Papaver somniferum* by two commercial methods. In one method, the immature capsule is cut and the latex collected from the wound. The air-dried latex is opium which contains alkaloids.

In a second method, the mature poppy capsules and the poppy capsule stems are collected, and threshed to remove the seeds and form a straw. When necessary, the straw is dried to a water content below 16%. Extraction by solvent or water or super critical fluid, such as $CO_2$, is usually employed to remove the alkaloids from the straw to produce a "concentrate of poppy straw".

While thebaine has no direct medical use, during recent years, demand for this alkaloid has increased as it is the raw material for the production of semi-synthetic drugs having analgesic, antitussive and sedative properties. Hydrocodone, thebacon, oxycodone and drotebanolare are other useful drugs that may be derived from thebaine. Naloxone made from thebaine is used as an antagonist in the treatment of morphine and heroin addicts. Etorphine and some of its analogues known as Bentley compounds prepared from thebaine have a much greater activity than morphine and are used in veterinary medicine and in capturing wild animals. The Diels-Adler adducts of thebaine are easily prepared in high yields and are of great interest.

The availability of thebaine is limited and its cost high. One reason for the limited availability of thebaine, and its high cost, is that total synthesis is difficult. Yet, the demand for thebaine remains. A second reason for the limited availability of thebaine, and its high cost, is that the primary source of thebaine is by extraction from the poppy plant, *Papaver somniferum*.

Morphine, is the major alkaloid that accumulates in capsules of *Papaver somniferum*. Moreover, according to the Merck Index, 11th edition, air dried latex contains alkaloids in the amounts shown in Table I.

TABLE I

|  | opium | straw |
|---|---|---|
| morphine, % | 10-16 | 1-3 |
| codeine, % | 0.8-2.5 | 0.05-0.3 |
| oripavine, % | 0-0.1 | 0-0.05 |
| thebaine, % | 0.5-2 | 0.15-0.65 |

As can be seen, from the above table the yield of thebaine and oripavine is confounded with that of other alkaloids. Thus, the supply of thebaine and oripavine is to a great degree limited to some fraction of the demand for morphine.

As seen from Table I oripavine is not recoverable from *Papaver somiferum* in any practical yield. Since oripavine has traditionally not been demanded in the same quantities as thebaine, there has been no real shortage of this material. However *Papaver somniferum* is now being increasingly cultivated for the production of oripavine for the pharmaceutical market.

Traditionally, trinexapac-ethyl, an acylcyclohexanedione compound has been used as a plant growth regulator, which reduces stem growth by inhibition of internode elongation. It is absorbed by the foliage with translocation to the growing shoot. Used commonly on highly maintained turfgrasses, it has had a role in evaluating growth suppression patterns and suppression of seedhead formation. Further uses of trinexapac-ethyl include the prevention of lodging in cereals, on winter oilseed rape and as a maturation promoter in sugar cane. Prohexadione-calcium is the calcium salt of another acylcyclohexanedione compound and is a plant growth regulator and retardant and, like trinexapac-ethyl, has also been used as an anti-lodging agent in small grain cereals. It could also be used as a growth retardant in turf, peanuts, flowers and to inhibit new twig elongation of fruit trees.

In work leading up to the present invention, the inventors unexpectedly found that the application of certain plant growth regulators, such as acylcyclohexanedione compounds and methyl jasmonate, in combination or individually, to poppy plants altered the alkaloid composition of a poppy plant, in particular by decreasing the proportion of morphine and increasing the proportion of thebaine and oripavine in poppy plants when compared to control plants to which the plant growth regulators had not been applied.

SUMMARY OF THE INVENTION

The present invention now provides a method of altering the alkaloid composition of a poppy plant comprising the step of applying an effective amount of an acylcyclohexanedione compound or agriculturally acceptable salt or ester thereof to said poppy plant or a locus thereof.

Another aspect of the invention provides a method of decreasing the proportion of morphine and/or increasing the proportion of thebaine and/or oripavine in a poppy plant comprising the step of applying an effective amount of an acylcyclohexanedione compound or agriculturally acceptable salt or ester thereof to said poppy plant or a locus thereof.

Yet another aspect of the invention provides a method of producing thebaine and/or oripavine comprising the steps of:
 (i) applying an effective amount of an acylcyclohexanedione compound or agriculturally acceptable salt or ester thereof to a poppy plant or locus thereof;
 (ii) harvesting poppy capsules to produce a straw from the poppy plant; and
 (iii) extracting thebaine and/or oripavine from the straw.

Still yet another aspect of the invention provides a method of producing thebaine and/or oripavine comprising the steps of:
 (i) applying an effective amount of an acylcyclohexanedione compound or agriculturally acceptable salt or ester thereof to a poppy plant or locus thereof;
 (ii) collecting and drying immature poppy capsules from the poppy plant to produce opium; and
 (iii) extracting thebaine and/or oripavine from the opium.

In a preferred embodiment, the acylcyclohexanedione compound or agriculturally acceptable salt or ester thereof is trinexapac-ethyl or prohexadione-calcium.

Preferably, the step of extraction in (iii) comprises either solvent or aqueous extraction to form a concentrate of poppy straw.

In yet another aspect of the invention there is provided a method of altering the alkaloid composition of a poppy plant, comprising the step of applying an effective amount of methyl jasmonate or agriculturally acceptable salt or ester thereof to said poppy plant or a locus thereof.

In still yet another aspect of the invention, there is provided method of decreasing the proportion of morphine and/or increasing the proportion of thebaine and/or oripavine in a poppy plant comprising the step of applying an effective amount of methyl jasmonate or agriculturally acceptable salt or ester thereof to said poppy plant or a locus thereof.

Yet another aspect of the invention provides a method of producing thebaine and/or oripavine comprising the steps of:
  (i) applying an effective amount of a methyl jasmonate or agriculturally acceptable salt or ester thereof to a poppy plant or locus thereof;
  (ii) harvesting poppy capsules to produce a straw from the poppy plant; and
  (iii) extracting thebaine and/or oripavine from the straw.

Preferably, the step of extraction in (iii) comprises either solvent or aqueous extraction to form a concentrate of poppy straw.

Still yet another aspect of the invention provides a method of producing thebaine and/or oripavine comprising the steps of:
  (i) applying an effective amount of a methyl jasmonate or agriculturally acceptable salt or ester thereof to a poppy plant or locus thereof;
  (ii) collecting and drying immature poppy capsules from the poppy plant to produce opium; and
  (iii) extracting thebaine and/or oripavine from the opium.

BRIEF DESCRIPTION OF THE FIGURES

FIG. 1 structurally depicts a number of metabolic products derived from trinexapac-ethyl.

DETAILED DESCRIPTION OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference to any prior art in this specification is not, and should not be taken as, an acknowledgment or any form of suggestion that that prior art forms part of the common general knowledge in Australia.

As used herein, the term "alkyl", used either alone or in compound words, denotes saturated straight chain, branched or cyclic hydrocarbon groups, preferably $C_{1-20}$ alkyl, eg $C_{1-10}$ or $C_{1-6}$. Examples of straight chain and branched alkyl include methyl, ethyl, propyl, isopropyl, butyl, sec-butyl, tert-butyl, n-pentyl and branched isomers thereof, n-hexyl and branched isomers thereof, n-heptyl and branched isomers thereof, n-octyl and branched isomers thereof, n-nonyl and branched isomers thereof, and n-decyl and branched isomers thereof. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like. An alkyl group may be further optionally substituted by one or more optional substituents as herein defined. Some preferred substituted alkyl include alkoxyalkyl (such as alkoxymethyl), alkylthioalkyl (such as alkylthiomethyl), phenylalkyl (such as phenylmethyl (benzyl) or phenylethyl, and wherein the phenyl group may be further substituted), thienylalkyl (such as thienylmethyl), haloalkyl, and aryloxyalkyl (such as phenoxymethyl). When used as a specified radical for any of R, $R_1$, $R_2$, $R_3$ or $R_4$. These may be further optionally substituted as described herein.

The term "alkenyl" as used herein denotes groups formed from straight chain, branched or cyclic hydrocarbon residues containing at least one carbon to carbon double bond including ethylenically mono-, di- or poly-unsaturated alkyl or cycloalkyl groups as previously defined, preferably $C_{2-20}$ alkenyl (eg $C_{2-10}$ or $C_{2-6}$). Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4, pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl. An alkenyl group may be optionally substituted by one or more optional substituents as herein defined.

As used herein the term "alkynyl" denotes groups formed from straight chain, branched or cyclic hydrocarbon residues containing at least one carbon-carbon triple bond including ethynically mono-, di- or poly-unsaturated alkyl or cycloalkyl groups as previously defined. The term preferably refers to $C_{2-20}$ alkynyl more preferably $C_{2-10}$ alkynyl. Examples include ethynyl, 1-propynyl, 2-propynyl, and butynyl isomers, and pentynyl isomers. An alkynyl group may be further optionally substituted by one or more optional substituents as herein defined.

The term "aryl" used either alone or in compound words denotes single, polynuclear, conjugated or fused residues of aromatic hydrocarbons (carboaryl) or aromatic heterocyclic (heteroaryl) systems where one or more carbon atoms (and where appropriate hydrogen atoms attached thereto) of a cyclic hydrocarbon residue are replaced to provide an aromatic heterocyclic residue. Suitable heteroatoms include O, N and S. Examples of carboaryl include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl and chrysenyl. Preferred carboaryl groups include phenyl and naphthyl, particularly phenyl. Examples of heteroaryl include pyridyl, thienyl, furyl, pyrrolyl, indolyl, pyridazinyl, pyrazolyl, pyrazinyl, thiazolyl, pyimidinyl. Preferred heteroaryl include pyridyl, thienyl, furyl and pyrrolyl. An aryl group may be further optionally substituted by one or more optional substituents as herein defined.

The term "heterocyclyl" used either alone or in compound words includes cyclic hydrocarbon residues, preferably $C_3$-$C_{20}$ (e.g. $C_{3-10}$ or $C_{3-6}$) wherein one or more carbon atoms (and where appropriate, hydrogen atoms attached thereto) are replaced by a heteroatom so as to provide a non-aromatic residue. Suitable heteroatoms include N, O and S. Where two or more carbon atoms are replaced, this may be by two or more of the same heteroatom or by different heteroatoms. Suitable examples of heterocyclic groups may include pyrrolidinyl, pyrrolinyl, piperidyl, piperazinyl, morpholino, indolinyl, imidazolidinyl, pyrazolidinyl, thiomorpholino, dioxanyl, tetrahydrofuranyl, tetrahydropyranyl, tetrahydropyrrolyl etc.

A heterocyclyl group may be further optionally substituted by one or more optional substituents as herein defined.

The term "acyl" either alone or in compound words denotes a group containing the moiety C=O (and not being a carboxylic acid, ester or amide) Preferred acyl includes C(O)—R, wherein R is hydrogen or an alkyl, alkenyl, alkynyl, aryl, or heterocyclyl, residue as defined above, preferably a $C_{1-20}$ residue. Examples of acyl include formyl; straight chain or branched alkanoyl such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aryloxyalkanoyl such as phenoxyacetyl and phenoxypropionyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolyglyoxyloyl and thienylglyoxyloyl.

The terms alkoxy, alkenoxy alkynoxy, aryloxy, heteroaryloxy, heterocyclyloxy and acyloxy respectively denote alkyl, alkenyl, alkynyl aryl, heteroaryl, heterocyclyl and acyl groups as hereinbefore defined when linked by oxygen.

The term thioalkyl refers to an alkyl group when linked by sulfur.

"Halogen" or "halo" refers to fluorine, chlorine, bromine or iodine.

The term "carboxylic acid" refers to the group $CO_2H$ and "carboxylic ester" or "ester" refers to the group $CO_2R$ wherein R is any group not being H. Preferred R includes alkyl, alkenyl, alkynyl and aryl (carbaryl and heteroaryl) and heterocyclyl, each of which may be optionally substituted. Some examples include $CO_2C_{1-20}$alkyl, $CO_2$aryl (eg. $CO_2$phenyl) and $CO_2$aralkyl (eg. $CO_2$benzyl).

The terms "amino" and "carboxylic amide" refer to groups NRR' and CONRR' respectively, wherein R and R" can independently be H, alkyl, alkenyl, alkynyl, aryl (carboaryl and heteroaryl), acyl and heterocyclyl, each of which may be optionally substituted. Some examples include $NH_2NHC_{1-20}$alkyl, NHaryl, $NdiC_{1-20}$alkyl, $NHCOC_{1-20}$alkyl, NHCOaryl (eg. NHCOphenyl), $CONH_2$, $CONHC_{1-20}$alkyl, CONHaryl (eg. CONHbenzyl), and $CONHdiC_{1-20}$alkyl.

In this specification "optionally substituted" is taken to mean that a group may or may not be further substituted or fused (so as to form a condensed polycyclic group) with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy mercapto, alkylthio, benzylthio, acylthio, cyano, nitro, sulfate and phosphate groups.

Examples of optional substituents include alkyl, (eg $C_{1-6}$alkyl such as methyl, ethyl, propyl, butyl, cyclopropyl, cyclobutyl, cyclopentyl or cyclohexyl), hydroxyalkyl (eg hydroxymethyl, hydroxyethyl, hydroxypropyl), alkoxyalkyl (eg methoxymethyl, methoxyethyl, methoxypropyl, ethoxymethyl, ethoxyethyl, ethoxypropyl etc) alkoxy (eg $C_{1-6}$ alkoxy such as methoxy, ethoxy, propoxy, butoxy, cyclopropoxy, cyclobutoxy), alkylthio, halogen (F, Cl, Br, I), trifluoromethyl, trichloromethyl, tribromomethyl, hydroxy, phenyl (which itself may be further optionally substituted), benzyl (wherein benzyl itself may be further optionally substituted), phenoxy (wherein phenyl itself may be further optionally substituted), benzyloxy (wherein benzyl itself may be further optionally substituted), amino, alkylamino (eg $C_{1-6}$alkyl, such as methylamino, ethylamino, propylamino etc), dialkylamino (eg $C_{1-6}$alkyl, such as dimethylamino, diethylamino, dipropylamino), acylamino (eg $NHC(O)CH_3$), phenylamino (wherein phenyl itself may be further substituted), nitro, formyl, —C(O)-alkyl (eg $C_{1-6}$ alkyl, such as acetyl), O—C(O)-alkyl (eg $C_{1-6}$alkyl, such as acetyloxy), benzoyl (wherein the phenyl group itself may be further optionally substituted), replacement of $CH_2$ with C=O, $CO_2H$, $CO_2$alkyl (eg $C_{1-6}$ alkyl such as methyl ester, ethyl ester, propyl ester, butyl ester), $CO_2$phenyl (wherein phenyl itself may be further substituted), $CONH_2$, CONHphenyl (wherein phenyl itself may be further substituted), CONHbenzyl (wherein benzyl itself may be further substituted), CONHalkyl (eg $C_{1-6}$ alkyl such as methyl ester, ethyl ester, propyl ester, butyl amide), CONHdialkyl (eg $C_{1-6}$alkyl), thienyl, furyl, pyridyl and methylenedioxy.

As used herein, an "acylcyclohexanedione compound" refers to a 1,3-cyclohexanedione bearing an acyl group (or enol form thereof) at the 2-position and a carboxylic acid, carboxylic ester or carboxylic amide at the 5-position, as well as agriculturally acceptable salts, esters and metabolic products thereof. It will be appreciated that, as noted above, tautomeric forms are also intended to be encompassed by the invention.

As used herein an "enol form" of a 1,3-cyclohexanedione compound having an acyl group at the 2-position refers to the enol which can be formed as a result of abstraction of the hydrogen atom located at C2 of the 1,3-cyclohexanedione ring. It will be understood that the enol can be formed with either of the carbonyl groups of the 1,3-cyclohexanedione ring or with the carbonyl group of the C2 acyl group, preferably with carbonyl of the C2 acyl group.

Exemplary acylcyclohexanedione compounds and methods of making such are disclosed in U.S. Pat. No. 6,083,882, U.S. Pat. No. 4,693,745 and U.S. Pat. No. 4,560,403, which are incorporated herein by reference in their entireties for all purposes.

In one embodiment of the invention, the acylcyclohexanedione compound is a compound of formula (I)

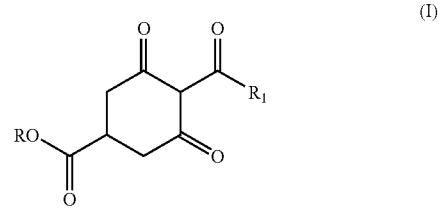

wherein R is selected from the group consisting of hydrogen, optionally substituted alkyl optionally substituted alkenyl, optionally substituted alkynyl and optionally substituted aryl; and $R_1$ is optionally substituted alkyl or optionally substituted aryl;

or an agriculturally acceptable salt or ester thereof.

In a preferred embodiment, $R_1$ is optionally substituted alkyl.

In another preferred embodiment R is hydrogen or optionally substituted alkyl or optionally substituted aryl.

One preferred subgroup of formula (I) is (Ia):

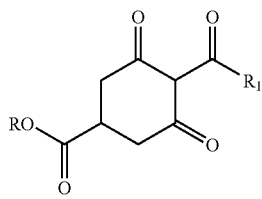

(Ia)

wherein R is selected from the group consisting of hydrogen, an optionally substituted alkyl group, an optionally substituted alkylthioalkyl group, or an optionally substituted phenyl group, and $R_1$ is selected from the group consisting of an optionally substituted alkyl group, an optionally substituted phenethyl group, an optionally substituted benzyl group, an optionally substituted phenoxymethyl group, an optionally substituted 2-thienylmethyl group, an optionally substituted alkoxymethyl group or an optionally substituted alkylthiomethyl group.

Some particular examples of compounds of Formula (I) contemplated by the present invention are depicted below in Table 2. Other specific examples are depicted in Table I of U.S. Pat. No. 4,560,403.

| R | $R_1$ |
|---|---|
| Et | CH(Me)Et |
| Et | $Bu_t$ |
| $Bu_t$ | $Bu_n$ |
| Me | $Pr_t$ |
| $CHEt_2$ | $Pr_n$ |
| Et | Me |
| $Bu_t$ | Et |
| Me | Me |
| Et | $(CH_2)_7Me$ |
| Et | $(CH_2)_6Me$ |
| Et | $(CH_2)_5Me$ |
| Et | $(CH_2)_4Me$ |
| Et | $Bu_I$ |
| Et | $Bu_n$ |
| Et | $Pr_I$ |
| $(CH_2)_2CHMe_2$ | $Pr_n$ |
| CH(Me)Et | $Pr_n$ |
| $Bu_I$ | $Pr_n$ |
| $Bu_n$ | $Pr_n$ |
| $Pr_I$ | $Pr_n$ |
| $Pr_n$ | $Pr_n$ |
| Et | $Pr_n$ |
| Me | $Pr_n$ |
| $Pr_I$ | Et |
| $Pr_n$ | Et |
| Et | Et |
| Me | Et |
| $Bu_t$ | Me |
| CH(Me)Et | Me |
| $Bu^I$ | Me |
| $Bu_n$ | Me |
| $Pr_I$ | Me |
| $Pr_n$ | Me |

Prohexadione, CAS Registry No. 127277-53-6, also known as 3,5-dioxo-4-propionylcyclohexanecarboxylic acid, 3,5-dioxo-4-(1-oxopropyl-)cyclohexanecarboxylic acid, and also 3-hydroxy-4-prionyl-5-oxo-3-cyclohex-ene carboxylic acid is one particularly preferred compound for use in the present invention and is represented below:

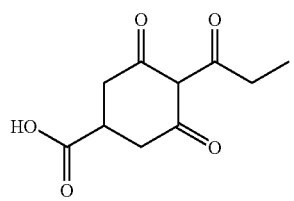

Desirable prohexadione salts include chloride, sulfate, metrab, acetate, carbonate, hydride, hydroxide, sodium, potassium, calcium, magnesium, barium, aluminum, nickel, copper, manganese, cobalt, zinc, iron and silver salts, with prohexadione-calcium, shown below, as a preferred salt.

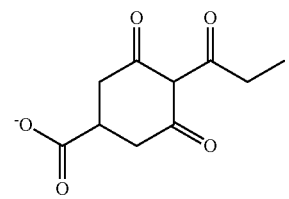

$1/2Ca^{2+}$

In another embodiment of the invention, the acylcyclohexanedione compound is a compound of formula (II)

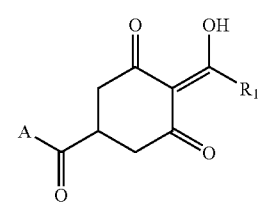

(II)

wherein $R_1$ is optionally substituted alkyl or optionally substituted aryl; and A is $OR_2$ or $NR_3R_4$ wherein $R_2$ is selected from the group consisting of hydrogen, optionally substituted alkyl, optionally substituted alkenyl, optionally substituted alkynyl and optionally substituted aryl; and $R_3$ and $R_4$ are independently selected from hydrogen, optionally substituted alkyl, optionally substituted alkenyl, optionally substituted alkynyl and optionally substituted aryl; or one of $R_3$ or $R_4$ is alkoxy and the other as defined above or $R_3$ and $R_4$ together with the nitrogen atom to which they are attached form a 5- or 6-membered heterocyclic ring which may contain an additional oxygen or sulfur atom;

or an agriculturally acceptable salt or ester thereof.

In a preferred embodiment, $R_1$ is optionally substituted alkyl.

A preferred subgroup of formula (II) is formula (IIa):

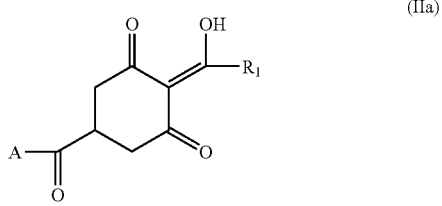

wherein:
$R_1$ is alkyl, preferably $C_3$-$C_6$ cycloalkyl; and
A is $OR_2$ or $NR_3R_4$;
$R_2$, $R_3$, and $R_4$ are each independently hydrogen, $C_1$-$C_6$ alkyl, $C_1$-$C_6$ haloalkyl, $C_2$-$C_{10}$ alkoxyalkyl, $C_2$-$C_{10}$ alkylthioalkyl; $C_3$-$C_6$ alkenyl, which is unsubstituted or substituted by halogen, $C_1$-$C_4$ alkoxy or $C_1$-$C_4$ alkylthio; $C_3$-$C_6$ alkynyl; phenyl or $C_1$-$C_6$ aralkyl, wherein the phenyl nucleus is unsubstituted or substituted by halogen, $C_1$-$C_4$ alkyl, $C_1$-$C_4$ alkoxy, $C_1$-$C_4$ haloalkyl, nitro or cyano; and
one of $R_3$ and $R_4$ is methoxy; or $R_3$ and $R_4$, together with the nitrogen atom to which they are attached, form a 5- or 6-membered heterocyclic ring system which may contain an additional oxygen or sulfur atom in the ring.

Specific compounds of the immediately above noted formula, for use in practicing embodiments of the invention include trinexapac, also known as 4-cyclopropyl(hydroxy)methylene-3,5-dioxocyclohexanecarboxylic acid, and its ethyl ester, trinexapac-ethyl, also known as ethyl 4-cyclopropyl(hydroxy)methylene-3,5-dioxocyclohexanec arboxylate, both shown below.

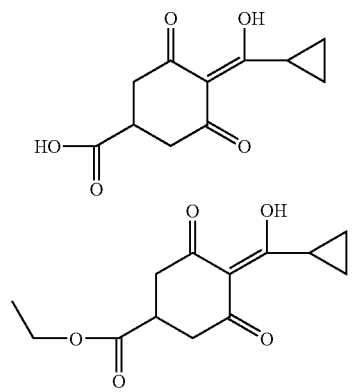

Some Examples of Formula (II) include those depicted below in Table 3. Other specific examples are described in U.S. Pat. No. 4,693,745:

TABLE 3

| A | $R_1$ |
|---|---|
| Et | Me |
| $Bu_i$ | $Pr_n$ |

Another compound useful in the present invention is methyl jasmonate as shown below or agriculturally acceptable salt or ester thereof, which may be used alone or in conjunction with acylcyclohexadiones described herein.

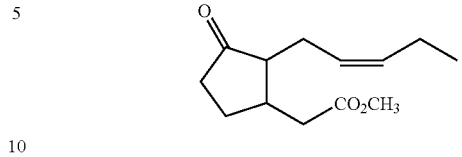

The acylcyclohexadione compounds and methyl jasmonate may be applied as salts or esters.

By the term "agriculturally acceptable salts" is meant salts the cations or anions of which are known and accepted in the art for the formation of salts for agricultural or horticultural use. Preferably the salts are water-soluble. Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts. Suitable acid addition salts, formed by compounds containing an nitrogen atom with an available lone pair, include salts with inorganic acids, for example hydrochlorides, sulfates, phosphates and nitrates and salts with organic acids, for example acetic acid. Suitable metal and alkaline earth metal hydroxides as salt formers include the salts of barium, aluminum, nickel, copper, manganese, cobalt zinc, iron, silver, lithium, sodium, potassium, magnesium or calcium. Additional salt formers include chloride, sulfate, metrab, acetate, carbonate, hydride, and hydroxide.

By the term "agriculturally acceptable esters" is meant those esters of the carboxylic acid group(s) which have an OR moiety that is not itself significantly herbicidal to any crop being treated and not significantly deleterious to the applicator, the environment, or the ultimate user of any crop being treated.

By the term "metabolic products" is meant those compounds produced as a result of the metabolism or degradation of acylcyclohexane compounds preferably within the poppy plant. Possible metabolites are presented in FIG. 1.

The plant growth regulators, such as acylcyclohexadione compounds and methyl jasmonate, may be applied unformulated or formulated into a composition. Preferably the compounds are applied in the form of a composition comprising the compound and one or more agriculturally acceptable additives and/or active ingredients. Compositions may contain the acylcyclohexanedione and/or methyl jasmonate in a range from 0.1 parts to 100 parts by weight.

Compositions for use in the invention may contain a carrier. The carrier may be any natural or synthetic organic or inorganic ingredient that facilitates dispersion of the composition or compound and contact with the plant. The carrier may be solid (e.g. clays, synthetic silicates, silica, resins, waxes, kaolin, bentonite, dolomite, calcium carbonate, talc, powdered magnesia, Fuller's earth, gypsum, diatomaceous earth, China clay, and combinations thereof); liquid (e.g. water, aqueous solutions, N-methylpyrrolidone, kerosene, cyclohexanone, methylethyl ketone, acetonitrile, methanol, ethanol, isopropyl alcohol, acetone, butyl cellosolved, 2-ethyl-1hexanol, cyclohexanone, methyl cellulose, polyvinyl alcohol, sodium lignin sulfonates, polymeric alkyl naphthalene sulfonates, sodium naphthalene sulfonate, polymethylene bisnaphthalenesulfonate, sodium N-methyl-N-(long chain acid) laureates, hydrocarbons and other water-immiscible ethers, esters and ketones, and combinations thereof); or a combination of solid and liquid carriers.

Compositions useful in the present invention may also contain one or more surfactants to increase the biological effectiveness of the active ingredient. Suitable surface active ingredients include surfactants, emulsifying agents, and wetting agents. A wide range of surfactants is available and can be selected readily by those skilled in the art from "The Handbook of Industrial Surfactants," 2nd Edition, Gower (1997), which is incorporated herein by reference in its entirety for all purposes. There is no restriction on the type or chemical class of surfactant(s) that can be used. Nonionic, anionic, cationic and amphoteric types, or combinations of more than one of these types, may all be useful in particular situations.

Among nonionic surfactants, exemplary classes include polyoxyethylene alkyl, alkyne, alkynyl or alkylaryl ethers, such as polyoxyethylene primary or secondary alcohols, alkylphenols or acetylenic diols; polyoxyethylene alkyl or alkyne esters, such as ethoxylated fatty acids; sorbitan alkylesters, whether ethoxylated or not; glyceryl alkylesters; sucrose esters; and alkyl polyglycosides. Exemplary anionic surfactant classes include fatty acids, sulfates, sulfonates, and phosphate mono- and diesters of alcohols, alkylphenols, polyoxyethylene alcohols and polyoxyethylene alkylphenols, and carboxylates of polyoxyethylene alcohols and polyoxyethylene alkylphenols. These can be used in their acid form but are more typically used as salts, for example sodium, potassium or ammonium salts.

Cationic surfactants classes include polyoxyethylene tertiary alkylamines or alkenylamines, such as ethoxylated fatty amines, quaternary ammonium surfactants and polyoxyethylene alkyletheramines. Representative specific examples of such cationic surfactants include polyoxyethylene (5) cocoamine, polyoxyethylene (15) tallowamine, distearyldimethylammonium chloride, N-dodecylpyridine chloride and polyoxypropylene (8) ethoxytrimethylammonium chloride. Many cationic quaternary ammonium surfactants of diverse structures are known in the art to be useful in combination with herbicides and can be used in compositions contemplated herein.

Suitable emulsifying agents and wetting agents include, but are not limited to, ionic and nonionic types such as polyacrylic acid salts, lignosulphonic acid salts, phenolsulphonic or naphthalenesulphonic acids, products of polycondensation of ethylene oxide with fatty alcohols, fatty acids or fatty amines, substituted phenols (especially alkylphenols or arylphenols), sulphonosuccinic acid ester salts, taurine derivatives (especially alkyl taurates), phosphoric esters of alcohols or products of polycondensation of ethylene oxide with phenols, esters of fatty acids with polyhydric alcohols, and derivatives having sulphate, sulphonate and phosphate groups, of the compounds above.

The methods of the invention may also be used in conjunction with the application of other active agents, for example fertilizers such as ammonium nitrate, urea, potash, and superphosphate; phytotoxicants and plant growth regulators; methyl jasmonate; safeners; fungicides; pesticides and other alkaloid altering compositions such as thidiazuron or clopyralid. These additional agents may be used in combination (either together, separately or sequentially) with the above-described compositions. Thus, compositions used in the invention may also contain one or more active agents. Alternatively, the poppy plant(s) may be treated with other active agents before or after applying the acylcyclohexanedione or methyl jasmonate. Alternatively, a separate composition containing the active agent may be applied concurrently.

Other optional components may be admixed with the present compositions to facilitate the application and/or effectiveness of the active ingredient. To this end, optional components that may be added include antifoaming agents including silicone based antifoaming agents; thickening agents such as fumed silica; antimicrobial agents; antioxidants; buffers; dyes; perfumes; stabilizing agents; and antifreezing agents. Exemplary antifreezing agents include but are not limited to, glycols such as propylene glycol and ethylene glycol, N-methylpyrrolidone, cyclohexanone, and alcohols such as ethanol and methanol.

The compounds used in the present invention may be present in any effective formulation, including, but not limited to, dusting powders or granules; dispersible powders, granules or grains; aqueous dispersions; emulsions or microencapsulation.

Powders, including dusting powders or granules and dispersible powders, granules or grains contain at least one active ingredient and an inert solid extender or carrier, such as kaolin, bentonite, dolomite, calcium carbonate, talc, powdered magnesia, Fuller's earth, gypsum, diatomaceous earth and China clay. Dispersible powders, granules and grains typically also include one or more wetting and dispersing agents, such as surfactants.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agents(s). Suitable organic solvents are kerosene, cyclohexanone, methylethyl ketone, acetone, methanol, acetonitrile, and the like. The compositions may also be in the form of liquid preparations for use as dips or sprays which are generally aqueous dispersions or emulsions containing the active ingredient in the presence of one or more of wetting agent(s), dispersing agent(s), emulsifying agent(s) or suspending agent(s).

Typical liquid solutions include the active ingredient, a carrier, and optionally, a surface active agent. The dilute solutions of the present compositions generally contain about 0.1 to about 50 parts active ingredient, about 0.25 to about 50 parts carrier, and about 0 to about 94 parts surface active agent, all parts being by weight based on the total weight of the composition. Similarly, the concentrated compositions typically include about 40 to about 95 parts active ingredient, about 5 to about 25 parts carrier, and about 0 to about 20 parts surface active agent.

Emulsifications are usually solutions of active ingredients in water-immiscible or partially water-immiscible solvents as the carrier together with at least one surface active agent. Suitable solvents for the active ingredients of this invention include, but are not limited to, hydrocarbons and water-immiscible ethers, esters or ketones. The emulsification compositions generally contain from 5 to 95%, preferably 20 to 70% by weight of the active compound of this invention as active ingredient; 1 to 40%, preferably 5 to 20% by weight of surfactant; and 4 to 94%, preferably 10 to 75% by weight of liquid carrier.

The compounds useful in the present invention may be readily synthesized using techniques generally known to synthetic organic chemists. In general, the compounds and compositions may also be purchased commercially. In this regard, examples of commercial formulations of trinexapac-ethyl are Moddus™, Primo™, Primo MAXX™, which are manufactured by Syngenta and an example of commercial formulation of prohexadione-calcium is BAS125 10W™, Regalis™ and Apogee™ all of which are manufactured by BASF™. The compositions may be prepared in known manner, for example by homogeneously mixing or grinding the active ingredients with other ingredients. Additional components may be admixed with the composition at any point during the process, including during and/or after any mixing.

The term "alkaloid" encompasses a class of organic compounds containing nitrogen, isolated from plants, particularly poppy plants and includes thebaine, oripavine, neopinone, codeinone, morphinone, codeine and morphine. Preferably, the alkaloid is selected from the group consisting of morphine, thebaine and oripavine. The term "altering" encompasses the decrease in the proportion of morphine, and/or increase in the proportion of thebaine and/or oripavine when compared to a poppy plant which has not been treated in accordance with the invention.

Preferably, the alteration of the alkaloid content involves either the decrease in morphine yield and/or increase in thebaine and/or oripavine yield. The terms "decrease" or "increase" are relative to those levels of alkaloid content in poppies which have not been treated in accordance with the invention.

An "effective amount" of a compound will vary according to the prevailing conditions such as weather, plant species, feed pressure, growth stage, mode of application, cultivation practice and the like. In general, "effective amount" means the amount of the compound needed to achieve a detectable alteration in alkaloid composition. Suitable rates of the acylcyclohexanedione compound (active ingredient) may range from about 4 g a.i. per hectare to about 1750 g a.i. per hectare. As used herein "a.i." means active ingredient. Preferable rates of trinexapac-ethyl range from 125 g a.i. per hectare to 250 g a.i. per hectare and from 250 g a.i. to 500 g a.i. per hectare. Even more desirable is 500 g a.i. per hectare. Desirable rates of prohexadione-calcium are 5 g a.i. per hectare to 300 g a.i. per hectare.

A suitable concentration of a composition comprising trinexapac-ethyl ranges from 100 g a.i./L to 300 g a.i./L. Desired concentrations are 120 g a.i./L and 250 g a.i./L. Where the concentration of a composition of trinexapac-ethyl used is 250 g a.i./L, a suitable rate of application of a composition comprising trinexapac-ethyl is at least 40 ml per hectare. A suitable rate of application of composition comprising trinexapac-ethyl ranges from 40 mL per hectare to 7.0 L per hectare. Further suitable rates of application are for example 50 mL per hectare, 100 mL per hectare, 0.5 L per hectare, 0.75 L per hectare, 1.0 L per hectare, 1.25 L per hectare, 1.5 L per hectare, 2.0 L per hectare, 2.5 L per hectare, 3.0 L per hectare, 3.5 L per hectare, 4.0 L per hectare, 4.5 L per hectare, 5.0 L per hectare, 5.5 L per hectare and 6.0 L per hectare. Desirably the rate of trinexapac-ethyl applied is 0.5 L to 2.0 L per hectare. Even more desirable is the range of 1.0 L per hectare to 2.0 L per hectare when applied to increase the proportion of thebaine. Also preferable is the range of 0.5 L to 1.0 L per hectare when applied to increase the proportion of oripavine.

In addition, an example of a suitable range of concentration of a composition comprising prohexadione-calcium, which may be further diluted for application, is 50 g a.i./kg to 300 g a.i./kg. Preferred concentrations of prohexadione-calcium are 100 g a.i./kg and 275 g a.i./kg respectively. Where the concentration of a composition of prohexadione-calcium used is 100 g a.i./kg, a desirable rate of application is at least 40 g of composition per hectare. Even more preferable is the range of 50 g per hectare to 12 kg per hectare. Even more preferable is a range of 50 g per hectare to 6 kg per hectare. Even more desirable is a rate of at least 3 kg per hectare. However, the rates of 50 g per hectare, 100 g per hectare, 1 kg per hectare, 1.5 kg per hectare, 2 kg per hectare, 2.5 kg per hectare, 3 kg per hectare, 3.5 kg per hectare, 4 kg per hectare, 4.5 kg per hectare, 5 kg per hectare, 5.5 kg per hectare, 6 kg per hectare, 6.5 kg per hectare, 7 kg per hectare, 7.5 kg per hectare, 8 kg per hectare, 8.5 kg per hectare, 9 kg per hectare, 9.5 kg per hectare, 10 kg per hectare, 10.5 kg per hectare, 11 kg per hectare, 11.5 kg per hectare and 12 kg per hectare are all suitable rates of application.

Further, suitable concentrations of a composition comprising methyl jasmonate are for example greater than 95% pure methyl jasmonate. Suitable rates of application of a composition comprising greater than 95% pure methyl jasmonate include 10 ml per hectare to 1.0 L per hectare. Preferable rates range from 20 ml per hectare to 1.0 L per hectare. Further suitable rates include 20 ml per hectare, 30 ml per hectare, 40 ml per hectare, 50 ml per hectare, 100 ml per hectare, 150 ml per hectare, 200 ml per hectare, 250 ml per hectare, 300 ml per hectare, 350 ml per hectare, 400 ml per hectare, 450 ml per hectare, 500 ml per hectare, 550 ml per hectare, 600 ml per hectare, 650 ml per hectare, 700 ml per hectare, 800 ml per hectare, 900 ml per hectare, and 1.0 L per hectare. A desirable rate of application is 300 ml per hectare. Another desirable rate is 600 ml per hectare. Another desirable rate is 1.0 L per hectare.

Desirably, the alkaloid altering effects result in an increase or decrease in the amount of a particular alkaloid produced when compared with a control. Desirably the application of the compound or salt produces an increase or decrease in alkaloid amount when compared with a control. The term "control" refers to the same type, variety, or cultivar of poppy plant which has not been subjected to any alkaloid composition altering treatment or is not the result of any alkaloid composition altering treatment and has been subjected to exactly the same set of conditions but for application of an alkaloid composition altering treatment. Even more desirable is a decrease in morphine amount ranging from 60% to 90% when compared to a control. Also preferred is an increase in thebaine amount ranging from 50% to 1900%. An increase in oripavine amount ranging from 20% to 1800% is desirable. One of ordinary skill in the art will recognize that the potency and, therefore, an "effective amount," can vary for the various compounds/compositions used in the invention.

The term "poppy plant" refers to the *Papaver somniferum* as well as any part of a *Papaver somniferum* plant including, but not limited to, bud stem, seed, capsules, flowers, and leaves.

The term "morphine variety" encompasses a plant or strain of poppy wherein the amount of morphine and codeine produced is greater than the amount of thebaine and oripavine.

The term "thebaine variety" encompasses a plant or strain wherein the amount of morphine and codeine produced is less than the amount of thebaine and oripavine. The methods of the present invention relate especially to altering the alkaloid composition in the capsule and/or stem of the poppy plant.

Preferably, when a decrease in morphine is to be achieved, a composition comprising an acylcyclohexadione is applied to a morphine or thebaine variety. Preferably, when an increase in thebaine is to be achieved, a composition comprising trinexapac-ethyl or prohexadione-calcium is applied to a morphine or thebaine variety. Even more preferable is if the composition is applied to a thebaine variety. Preferably, when an increase in oripavine is to be achieved, a composition comprising trinexapac-ethyl or prohexadione-calcium is applied to a morphine or thebaine variety. Even more preferable is if the composition is applied to a morphine variety. In order to maximise the proportion of oripavine and minimize the proportion of morphine it is preferable that the composition is applied to a thebaine variety. However, a maximal amount of oripavine may be achieved if the composition is applied to a morphine variety.

As used throughout, the term "applying", or variations thereof such as "application", is used to mean that the poppy plant or locus thereof has contact with the described compound(s) or composition(s) thereof by application methods known in the art. As such, the compounds (and their salts) of the present invention can be applied in a number of ways, for example, they can be applied, formulated or unformulated, directly to the foliage of the plant or they can be sprayed on, broadcast, dusted on or applied as a cream or paste formulation or they can be applied as slow release granules (ie by injecting, shanking, chiseling or working into the soil). Compositions may be applied in a single application. Multiple, or separate or sequential applications of the compound(s) or composition(s) used in the invention are preferred to decrease the proportion of morphine and increase the proportion of thebaine and/or oripavine. "Locus thereof" refers to the general area in which the poppy plant(s) are grown to which application of compound(s) used in the invention achieve the effect of altering the alkaloid composition in the poppy plant(s) or parts thereof. Thus, for example, the locus, can refer to the surrounding soil in which the plants are grown and may encompass the whole or part of the planted area. Also compounds used in the invention may also be applied to fertilizer or poppy seed and placed in the soil at sowing time. In addition, a (jet stream) of compound or chemical used in the invention may be directed at a point into the ground next to the poppy plant(s) and allowed to diffuse through the soil and be taken up by the roots of the poppy plant(s). The locus can also refer to the air surrounding the plant(s), when the compound or composition used in the invention can be applied in the form of a spray or vapour.

Poppy plants are normally grown from seed until they mature to produce capsules. Once the plant has matured the capsules and a part of the stem are harvested. After the seeds are collected for culinary use the deseeded capsules and stem (together known as "straw") are processed in order to extract useful chemicals such as plant alkaloids. The most valuable part of the plant is the capsule containing the majority of the total plant alkaloids. Stems and other parts of the plant also contain the alkaloids although in lower concentration.

During the growth from seed, poppy plants go through several developmental stages which are herein designated by the following terms: 4-6 leaf stage (early post emergent), 6-8 leaf stage, 8-10 leaf stage, 10-12 leaf stage (row cover), ground cover (12-14 leaf), run up, bud emergence, bud to hook, hook and lastly flowering. Maturity and harvesting occur 6-8 weeks post flowering. The ground cover stage is where plants have 12-14 leaves, are in a rosette habit and, as the term implies are covering the ground such that the bare ground is not easily visible when the plants have the normal row spacing of 15-20 cm. Run-up includes both early run-up and late run-up. Early run-up is the emergence of the stem from the rosettes. Late run-up is the beginning of the emergence of the buds as the stem is elongated. Clearly not all the plants in any given crop will be at the same growth stage however the terms used herein refer to the growth stage of the leaves of the majority of the plants or of the majority of primary buds once they have appeared.

The compositions for use in the present invention, comprising for example acylcyclohexanedione, may be applied anytime up to flowering, but application during 10-12 leaf stage, ground cover, run up, bud emergence or hook growth stages is preferred in order to decrease the proportion of morphine and increase the proportion of thebaine or oripavine. Application at an early growth stage, for example at the 10-12 leaf stage or early run-up is also desirable to increase the proportion of oripavine. Application during at least one of the growth stages selected from the group consisting of ground cover, run-up, bud emergence, hook and early flowering is also desirable to increase the proportion of thebaine in a poppy plant or part thereof. Further, a composition comprising methyl jasmonate may be applied for example during the growth stages including run up, bud-emergence, hook and flowering. A preferred growth stage for the application of a composition comprising methyl jasmonate is early flowering.

When operating in accordance with the present invention, the poppy plants or area proximate to the poppy plants is contacted with an effective amount of the compound or composition of the present invention. The application of such compositions to terrestrial plants can be carried out by conventional methods, e.g. power dusters, boom and hand sprayers and spray dusters.

*Papaver somniferum* is postulated to have two biosynthetic pathways from thebaine to morphine as shown in the scheme below.

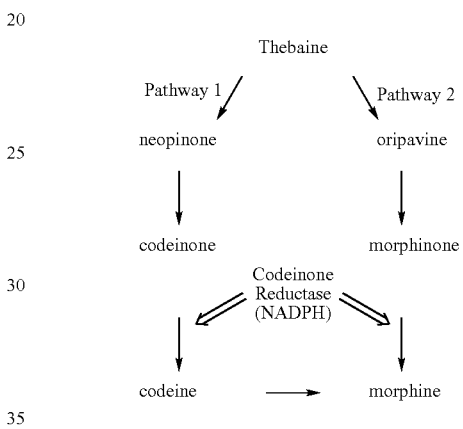

By the methods herein, varieties of *Papaver somniferum* were obtained having reduced morphine or codeine. Without wishing to limit the invention to one theory, it is believed, that the production or activity of codeinone reductase (NADPH) is substantially inhibited by the application of an acyclocyclohexadione compound, particularly, trinexapac-ethyl or prohexadione-calcium, to a poppy plant.

The term "opium" encompasses the air dried latex or the milky exudate from an immature or unripe (green) capsule of a poppy plant. The term "poppy straw" encompasses mature or ripe (dry) poppy capsules and stems which have been treated to remove the seeds, and form a straw.

The term "concentrate of poppy straw" includes the material arising when poppy straw has entered into a process for the concentration of its alkaloids, when such material is made available in trade, (Multilingual Dictionary Of Narcotic Drugs And Psychotropic Substances Under International Control, United Nations, New York, 1983). Not inconsistent with the foregoing definition, concentrate of poppy straw is defined as "the crude extract of poppy straw in either liquid, solid or powder form which contains the phenanthrene alkaloids of the opium poppy," 45 U.S. Federal Register 77466, Nov. 24, 1980. When in liquid form, the liquid is preferably concentrated before entering into commerce. The generally preferred concentrate of poppy straw is the powder form which results from simply removing the solvent or water following extraction of the poppy straw.

Recovering thebaine and/or oripavine from either the dried straw or from the opium of *Papaver somniferum* is a process well established in the art. Until now, thebaine has been extracted from this plant as a part of the process of extracting morphine and codeine. In one process, the straw is treated with a small amount of lime and water to soften the capsules and to form a free base of the alkaloids. Countercurrent extraction of the softened straw with methanol, ethanol or other suitable solvent forms a solventwater extract or "miscella" containing the alkaloids, with morphine at a concentration of about 0.5-1 g/L where the straw is from standard *Papaver somniferum*. The volume of the miscella is reduced about 30.times. under vacuum to produce an aqueous concentrate. Thebaine is extracted from aqueous concentrate using a liquid/liquid extraction with toluene, xylene or similar water immisible solvent, adjusting pH for the best separation of thebaine. The thebaine is recovered from the solvent. Of course, recovering thebaine from the improved *Papaver somniferum* provided herein will be facilitated by the fact that the concentration of the thebaine in the miscella will be much higher than that of other alkaloids and thus can be more easily collected by precipitation. Also, in the substantial absence of morphine and codeine, the thebaine might be directly extracted from the straw using solvent. In the case of oripavine, however, oripavine may be recovered from an aqueous concentrate by adjusting to basic pH and extracting with organic solvent such as toluene. The oripavine will remain in the aqueous layer and the thebaine will be found in the organic solvent. The oripavine can then be recovered from the aqueous phase by adjusting the pH to precipitate the oripavine.

The present invention is further described by the following non-limiting Examples.

GENERAL METHODS USED IN EXAMPLES

Poppy seed was treated with Thiram (5.6 g of Thiram 800/kg seed) and Apron (4 g/kg) and sown at a rate of approximately 1 kg/ha. Fertilisers were applied at sowing. Most commonly, either 50:50 lime:super/triplesuper phosphate at 125 kg/ha, or lime:super (50:50) at 250 kg/ha, were mixed with seed and planted at a depth of 15 mm. In the same operation, NPK (nitrogen:phosphorous:potassium) at various rates was banded 75 mm below the seed, unless otherwise stated. All crops were subjected to herbicide sprays for weed control, fungicide sprays for disease control, insecticide sprays if appropriate and were irrigated as required.

Spray applications were made with a purpose-built precision sprayer, using Silvan Lurmark flat-fan, low-drift nozzles (LD110-0015). Spray equipment was calibrated to deliver 153 L water/ha or 250 L/ha.

At harvest, a 2 m×4 m quadrat was placed in each plot and capsules hand-picked from this area. Capsules were broken up, seed and capsule material separated and weighed. Capsule moisture readings were taken with a moisture meter and a capsule sample from each plot was assayed for morphine, thebaine, codeine, and oripavine. Yield parameters, alkaloid assay (%) and alkaloid production (kg/ha), were calculated on a software program entitled "Pesticide Research Manager" (version 5 for Windows) using the formulae set out below under "Harvest Parameter Calculations". Briefly, capsule weight was adjusted for moisture to a dry weight, 5% of seed weight was added to this (this amount of capsule material regularly occurs in seed samples after processing) to give a capsule weight per plot. Seed weight was adjusted to 95% of crude weight. Straw weights were determined by multiplying dry capsule weight by 1.3 (estimated amount of stem material in a commercial harvest) and adjusted to 11% moisture. Alkaloid production was calculated by multiplying straw assay (calculated on the basis that the stem assay is 11% of capsule assay and that capsules and stems account for 75% and 25% of the straw, respectively) by straw weight. Analyses of variance and a Multiple Range Test were performed on the data. Significant differences (P=0.05) between treatments are denoted by different lower case letters adjacent to treatment means in the tables of results. Treatments denoted by a combination of lower case letters indicates no significant difference between those results and the results shown denoted by each lower case letter contained in the combination.

Harvest Parameter Calculations

HARVEST PARAMETER CALCULATIONS FOR PESTICIDE RESEARCH MANAGER (VERSION 5 FOR WINDOWS)
The [ ] in the calculations below refer to a column e.g. "[2]" is capsule weight which is the subject of the calculation in formula 1.

| Column Number | |
|---|---|
| [1] | Seed weight (unadjusted) g/plot (8 m$^2$) |
| [2] | Capsule weight (unadjusted) g/plot (8 m$^2$) |
| [3] | Moisture (%) |
| [4] | Dry capsule weight (unadjusted) g/plot (8 m$^2$) formula 1: [2] − (([2] * [3])/100) |
| [5] | 5% seed weight (unadjusted) g/plot (8 m$^2$) formula 2: [1] * 0.05 |
| [6] | Dry 5% extra capsule weight g/plot (8 m$^2$) formula 3: [5] − (([5] * [3])/100) |
| [7] | Dry capsule weight (adjusted) g/plot (8 m$^2$) formula 4: [4] + [6] |
| [8] | Seed weight (adjusted) g/plot (8 m$^2$) formula 5: [1] − [5] |
| [9] | Total weight (adjusted) g/plot (8 m$^2$) formula 6: [7] + [8] |
| [10] | Capsule: seed ratio formula 7: [7]/[8] |
| [11] | Straw weight kg/ha formula 8: [7] * 1.11 * 1.3 * 1.25 |
| [12] | Seed weight kg/ha formula 9: [8] * 1.25 |
| [13] | Yield t/ha formula 10: ([11] + [12])/1000 |
| [14] | Capsule morphine assay (anhydrous) % |
| [15] | Capsule morphine assay (11% moisture) formula 11: [14] * 0.89 |
| [16] | Stem morphine assay (11% moisture) formula 12: [14] * 0.89 * 0.115 |
| [17] | Straw morphine assay (11% moisture) % formula 13: ([15] * 0.75) + ([16] * 0.25) |
| [18] | Morphine production kg/ha formula 14: ([11] * [17])/100 |
| [20] | Capsule thebaine assay (anhydrous) % |
| [21] | Capsule thebaine assay (11% moisture) % formula 15: [20] * 0.89 |
| [22] | Stem thebaine assay (11% moisture) % formula 16: [20] * 0.267 |
| [23] | Straw thebaine assay (11% moisture) % formula 17: ([21] * 0.75) + (([22] * 0.25) |
| [24] | Thebaine production kg/ha formula 18: ([11] * [23])/100 |
| [25] | Capsule oripavine assay (anhydrous) % |
| [26] | Capsule oripavine assay (11% moisture) formula 19: [25] * 0.89 |
| [27] | Stem oripavine assay (11% moisture) formula 20: [25] * 0.445 |
| [28] | Straw oripavine assay (11% moisture) % formula 21: ([26] * 0.75) + ([27] * 0.25) |
| [29] | Oripavine production kg/ha formula 22: ([11] * [28])/100 |
| [30] | Capsule codeine assay (anhydrous) % |
| [31] | Capsule codeine assay (11% moisture) formula 23: [30] * 0.89 |
| [32] | Stem codeine assay (11% moisture) % formula 24: [30] * 0.150 |
| [33] | Straw codeine assay (11% moisture) % formula 25: ([31] * 0.75) + ([32] * 0.25) |
| [34] | Codeine production kg/ha formula 26: ([11] * [33])/100 |

| HARVEST PARAMETER HEADINGS FOR PESTICIDE RESEARCH MANAGER | | | | | |
|---|---|---|---|---|---|
| Column Number | Line No 1 | 2 | 3 | Calculation Number | Decimal Places |
| 1 | SEED WT | (CRUDE) | g/plot | — | 0 |
| 2 | CAPS WT. | (CRUDE) | g/plot | — | 0 |
| 3 | MOISTURE | | % | | 1 |
| 4 | DRY CAPS | (CRUDE) | g/plot | 1 | 0 |
| 5 | 5% SEED | | g/plot | 2 | 1 |
| 6 | 5% x CAPS | DRY | g/plot | 3 | 1 |
| 7 | DRY CAPS | (ADJ) | g/plot | 4 | 1 |
| 8 | SEED WT | (ADJ) | g/plot | 5 | 1 |
| 9 | TOTAL WT | | g/plot | 6 | 1 |
| 10 | CAPSULE/SEED | | RATIO | 7 | 3 |
| 11 | STRAW | | kg/ha | 8 | 0 |
| 12 | SEED | | kg/ha | 9 | 0 |
| 13 | YIELD | | t/ha | 10 | 2 |
| 14 | CAPS M | DRY | % | | 3 |
| 15 | CAPSULE | MORPHINE | % | 11 | 3 |
| 16 | STEM M | 11% MOIST. | % | 12 | 3 |
| 17 | STRAW M | 11% MOIST. | % | 13 | 2 |
| 18 | MORPHINE | | kg/ha | 14 | 2 |

Explanation of some of the terms in formulae:

| | |
|---|---|
| 1.11 = | amount to convert dry straw to straw at 11% moisture |
| 1.3 = | amount required to convert capsule weight to capsule + (10 cm) stem weight |
| 1.25 = | conversion from g/plot (4 m$^2$) to kg/ha |
| 0.89 = | conversion of dry assay to assay at 11% moisture |
| 0.115 = | proportion of morphine to 10 cm stem compared to capsule (0.267, 0.445, 0.150 for thebaine, oripavine and codeine, respectively) |
| 0.75 = | proportion of capsule in straw |
| 0.25 = | proportion of stem in straw |

Summary of Results
TRINEXAPAC-ETHYL

| EXAMPLE | VAR. | NO APPLICS. | RATES INVESTIG. (L/ha) | GROWTH STAGE | COMMENTS | REF. |
|---|---|---|---|---|---|---|
| 1 | M | 1 | .5, 1, 1.5, 2 | Early hook | | Table 1 |
| 2 | M | 1 | .5, 1 | Bud-emergence | +/−EDTA | Table 2 |
| 3 | M | 1 | 1 | Early run-up | 2 Formulations × 2 Water rates | Table 3 |
| 4 | M | 3 | 1 | ERU, BE, Hook | +/−Methyl jasmonate | Table 4 |
| 5 | M | 1 or 2 | 1 | ERU, BE, Early hook | +Lontrel | Table 5 |
| 6 | M | 1 or 4 | 1 | ERU, Mid-RU, BE, Hook | +/−Lontrel | Table 6 |
| 7 | M, T | 2 | 1 | ERU, Late RU | | Table 7 |
| 8 | M, T | 2 | 1 | ERU, LRU | +Lontrel | Table 8 |
| 9 | T | 1 or 4 | 1, 1.5, 2 | Ground cover, ERU, LRU, Hook | +Lontrel | Table 9 |
| 10 | T | 3 | 1, 1.5 | ERU, LRU, BE, Hook | +Lontrel | Table 10 |
| 11 | T | 1 or 4 | 1, 1.5, 2 | GC, RU, Late BE, Hook | +Lontrel | Table 11 |
| 12 | T | 3 | 1, 1.5 | RU, BE, Hook | +Lontrel | Table 12 |
| 13 | T | 1 or 4 | 1, 1.5, 2 | GC, ERU, BE, Hook | +Lontrel | Table 13 |
| 14 | T | 3 | 1, 1.5 | ERU, LRU/BE, Hook | +Lontrel | Table 14 |
| 15 | T | 2 | 1 | ERU, BE | +Lontrel + Protectant fungicides | Table 15 |
| 16 | T | 2 | 1 | ERU, BE | +Clopyralid | Table 16 |
| 17 | T | 1 | 1 | LRU/BE | +Lontrel + Curative fungicides | Table 17 |
| 18 | M | 1 | .05, .1, .5, 1 | 10-12 leaf, RU, BE, Hook, Early flowering | +/−Lontrel | Table 18 |
| 19 | T | 1 | .05, .1, .5, 1 | 10-12 leaf RU, BE, Hook, Early flowering | +/−Lontrel | Table 19 |
| 20 | M | 5 | .4 | 10-12 leaf RU, BE, Hook, Early flowering | | Table 20 |

| PROHEXADIONE-CALCIUM | | | | | |
|---|---|---|---|---|---|
| EXAMPLE | VAR | NO APPLICS | RATES INVESTIG. (kg/ha) | GROWTH STAGE | COMMENTS |
| 21 | M | 1 | 3 | Hook | Water rates |
| 22 | T | 1 | 1, 2, 3, 4, 5, 6 | Hook | +Lontrel |
| 23 | T | 1 | 3 | Bud emergence, Hook, Early flowering, Full flower | +Lontrel |
| 24 | T | 1, 2 or 3 | 2.75 | BE, Hook, EF | +Lontrel |
| 25 | T | 1 | 3 | Hook | +Lontrel + Fungicides |
| 26 | T | 1 | 3 | Hook | +Lontrel + Fungicides |
| 27 | T | 1 | 3 | Hook | +Lontrel + Water rates + Compound 2 |
| 28 | M | 1 | .02, .1, .2, 1* | 10-12 leaf, Row cover, Early run up, BE, Hook | +Lontrel |

*Compound 4 (275 g/kg prohexadione-Ca)

| SUMMARY TABLE OF 2004-05 TRIALS | | | | | | |
|---|---|---|---|---|---|---|
| EXAMPLE | VAR. | NO. APPLICS. | RATES INVESTIG. (L/ha) | GROWTH STAGE | COMMENTS | REF. |
| 30 | T | 1, 2 or 3 | 1 | Ground Cover, Mid-Late Run-Up, Bud-Emergence | +Lontrel | Table 30 |
| 31 | T | 2 | .7, .8, 1 | RC, LRU | +Lontrel + Spraytech Oil | Table 31 |
| 32 | T | 2 | .7, .8, 1 | RC, LRU | +Lontrel + Codacide Oil | Table 32 |
| 33 | T | 2 | .7, .8, 1 | RC, LRU | +Lontrel + Codacide Oil | Table 33 |
| 34 | T | 1 | .5, 1 | GC | +Lontrel + Sunny | Table 34 |
| 35 | T | 1 | .5, 1 | GC | +Lontrel + Sunny | Table 35 |
| 36 | T | 2 | 1 | RC, GC, LRU | +Lontrel + Sunny | Table 36 |
| 37 | T | 2 or 3 | 1 | RC, ERU, LRU, BE, Hook | +Lontrel +/− methyl jasmonate | Table 37 |
| 38 | T | 2 or 3 | 1 | RC, ERU, LRU, Hook, Early flower | +Lontrel +/− methyl jasmonate | Table 38 |
| 39 | T | 2 or 3 | 1 | GC, ERU, M-LRU, BE, Hook | +Lontrel +/− methyl jasmonate | Table 39 |
| *40 | T | 5 | .25, .5 methyl jasmonate | GC, ERU, M-LRU, LBE, Hook | +Lontrel | Table 40 |

*No Compound 1 applied in this trial, rates/growth stages refer to methyl jasmonate

| LIST OF PRODUCTS | | |
|---|---|---|
| | ACTIVE INGREDIENT | FORMULATION |
| Compound 1 | 250 g/L trinexapac-ethyl | Emulsifiable concentrate |
| Compound 2 | 250 g/L trinexapac-ethyl | Micro-encapsulation |
| Compound 3 | 120 g/L trinexapac-ethyl | Emulsifiable concentrate |
| Compound 4 | 275 g/kg prohexadione-calcium | Dispersible granule |
| Compound 5 | 100 g/kg prohexadione-calcium | Dispersible granule |
| Lontrel ™ | 300 g/L clopyralid | Liquid |

Example 1

Introduction

Trial to evaluate Compound 1 applied once, but at four different rates. It was applied on 2 December to a morphine crop at early hook stage. Capsules were harvested from trial plots on 18 February.

TABLE 1a

Effect of treatments on yield parameters.

| Trt No. | Treatment Name | Rate | Rate Unit | STRAW kg/ha | SEED kg/ha | CAPSULE/ SEED RATIO | YIELD t/ha |
|---|---|---|---|---|---|---|---|
| 1 | NIL | | | 1870 a | 2143 a | 0.604 d | 4.01 a |
| 2 | COMPOUND 1 | .5 | L/HA | 1898 a | 1810 b | 0.726 c | 3.71 b |
| 3 | COMPOUND 1 | 1 | L/HA | 1902 a | 1754 bc | 0.751 b | 3.66 b |
| 4 | COMPOUND 1 | 1.5 | L/HA | 1866 a | 1665 c | 0.778 a | 3.53 b |
| 5 | COMPOUND 1 | 2 | L/HA | 1892 a | 1691 c | 0.776 a | 3.58 b |
| LSD (P = .05) | | | | 130.8 | 108.5 | 0.0238 | 0.231 |
| Standard Deviation | | | | 94.9 | 78.7 | 0.0173 | 0.168 |
| CV | | | | 5.03 | 4.34 | 2.38 | 4.54 |

TABLE 1b

Effect of treatments on alkaloid parameters.

| Trt No. | Treatment Name | Rate | Rate Unit | STRAW MORPHINE % | MORPHINE kg/ha | STRAW THEBAINE % | THEBAINE kg/ha | O'PAVINE % | ORI-PAVINE kg/ha | STRAW CODEINE % | CODEINE kg/ha |
|---|---|---|---|---|---|---|---|---|---|---|---|
| 1 | NIL | | | 1.79 a | 33.31 a | 0.124 d | 2.352 d | 0.029 c | 0.549 c | 0.046 a | 0.853 a |
| 2 | COMP 1 | .5 | L/HA | 0.68 b | 12.90 b | 0.991 c | 18.778 c | 0.309 a | 5.871 a | 0.043 a | 0.816 a |
| 3 | COMP 1 | 1 | L/HA | 0.53 c | 10.01 c | 1.273 b | 24.188 b | 0.311 a | 5.915 a | 0.037 b | 0.702 b |
| 4 | COMP 1 | 1.5 | L/HA | 0.42 cd | 7.82 d | 1.375 a | 25.629 ab | 0.279 b | 5.199 b | 0.035 b | 0.650 bc |
| 5 | COMP 1 | 2 | L/HA | 0.39 d | 7.33 d | 1.425 a | 26.925 a | 0.261 b | 4.939 b | 0.030 c | 0.573 c |
| LSD (P = .05) | | | | 0.116 | 1.636 | 0.0792 | 1.7565 | 0.0241 | 0.5961 | 0.0046 | 0.1091 |
| Standard Deviation | | | | 0.084 | 1.187 | 0.0575 | 1.2745 | 0.0175 | 0.4326 | 0.0033 | 0.0791 |
| CV | | | | 11.05 | 8.32 | 5.54 | 6.51 | 7.36 | 9.62 | 8.72 | 11.01 |

Example 2

Introduction

Trial to evaluate Compound 1 applied once, in the presence and absence of EDTA. It was applied, tank-mixed with EDTA in treatments 3 and 4, on 2 December to a morphine crop at bud-emergence stage. Capsules were harvested from trial plots on 10 February.

TABLE 2a

Effect of treatments on yield parameters.

| Trt No. | Treatment Name | Rate | Rate Unit | STRAW kg/ha | SEED kg/ha | CAPSULE/ SEED RATIO | YIELD t/ha |
|---|---|---|---|---|---|---|---|
| 1 | NIL | | | 1725 ab | 2049 a | 0.583 c | 3.77 a |
| 2 | COMPOUND 1 | 1 | L/HA | 1798 a | 1663 b | 0.752 a | 3.46 b |
| 3 | COMPOUND 1 | 1 | L/HA | 1768 a | 1666 b | 0.737 a | 3.43 b |
| 3 | EDTA | 1 | KG/HA | | | | |
| 4 | COMPOUND 1 | 5 | L/HA | 1740 ab | 1711 b | 0.705 b | 3.45 b |
| 4 | EDTA | 1 | KG/HA | | | | |
| 5 | EDTA | 1 | KG/HA | 1668 b | 1960 a | 0.590 c | 3.63 ab |
| LSD (P = .05) | | | | 89.1 | 100.9 | 0.0257 | 0.180 |
| Standard Deviation | | | | 64.7 | 73.2 | 0.0187 | 0.130 |
| CV | | | | 3.72 | 4.05 | 2.77 | 3.67 |

TABLE 2b

Effect of treatments on alkaloid parameters.

| Trt No. | Treatment Name | Rate | Rate Unit | STRAW MORPHINE % | MORPHINE kg/ha | STRAW THEBAINE % | THEBAINE kg/ha | STRAW O'PAVINE % | ORI-PAVINE kg/ha | STRAW CODEINE % | CO-DEINE kg/ha |
|---|---|---|---|---|---|---|---|---|---|---|---|
| 1 | NIL | | | 1.93 a | 33.29 a | 0.132 c | 2.262 c | 0.035 b | 0.603 c | 0.045 b | 0.768 b |
| 2 | COMP 1 | 1 | L/HA | 0.60 c | 10.80 c | 1.397 a | 25.051 a | 0.373 a | 6.660 ab | 0.047 b | 0.849 b |
| 3 | COMP 1 | 1 | L/HA | 0.62 c | 10.98 c | 1.380 a | 24.378 a | 0.393 a | 6.884 a | 0.046 b | 0.811 b |
| 3 | EDTA | 1 | KG/HA | | | | | | | | |
| 4 | COMP 1 | .5 | L/HA | 0.87 b | 15.12 b | 1.049 b | 18.290 b | 0.357 a | 6.208 b | 0.054 a | 0.943 a |
| 4 | EDTA | 1 | KG/HA | | | | | | | | |
| 5 | EDTA | 1 | KG/HA | 1.98 a | 32.97 a | 0.139 c | 2.350 c | 0.036 b | 0.618 c | 0.047 b | 0.790 b |
| LSD (P = .05) | | | | 0.128 | 1.932 | 0.0774 | 1.8425 | 0.0389 | 0.6334 | 0.0048 | 0.0881 |
| Standard Deviation | | | | 0.093 | 1.402 | 0.0562 | 1.3370 | 0.0283 | 0.4596 | 0.0035 | 0.0639 |
| CV | | | | 7.74 | 6.8 | 6.86 | 9.24 | 11.83 | 10.96 | 7.34 | 7.68 |

Example 3

Introduction

A trial to compare the performance of two different formulations of trinexapac-ethyl (Compound 1, a 250 g/L emulsifiable concentrate and Compound 3, a 120 g/L emulsifiable concentrate) and at different water volumes (153 L and 250 L/ha). Treatments were applied once to the morphine crop at early run-up, on 24 November. Capsules were harvested from trial plots on 11 February.

TABLE 3a

Effect of treatments on yield parameters.

| Trt No. | Trt Name | Product Rate | Water Rate | Rate Unit | STRAW kg/ha | SEED kg/ha | CAPSULE/SEED RATIO | YIELD t/ha |
|---|---|---|---|---|---|---|---|---|
| 1 | NIL | | | | 1542 b | 1919 a | 0.557 b | 3.46 a |
| 2 | COMPOUND 1 | 1 | 153 | L/HA | 1773 a | 1695 b | 0.730 a | 3.47 a |
| 3 | COMPOUND 1 | 1 | 250 | L/HA | 1850 a | 1793 ab | 0.718 a | 3.64 a |
| 4 | COMPOUND 3 | 2.083 | 153 | L/HA | 1777 a | 1705 b | 0.725 a | 3.48 a |
| 5 | COMPOUND 3 | 2.083 | 250 | L/HA | 1790 a | 1716 b | 0.727 a | 3.51 a |
| LSD (P = .05) | | | | | 123.4 | 173.2 | 0.0366 | 0.289 |
| Standard Deviation | | | | | 89.5 | 125.6 | 0.0266 | 0.210 |
| CV | | | | | 5.12 | 7.12 | 3.84 | 5.97 |

TABLE 3b

Effect of treatments on alkaloid parameters.

| Trt No. | Trt Name | Product Rate | Water Rate | STRAW MORPHINE % | MORPHINE kg/ha | STRAW THEBAINE % | THEBAINE kg/ha | STRAW O'PAVINE % | ORI-PAVINE kg/ha | STRAW CODEINE % | CODEINE kg/ha |
|---|---|---|---|---|---|---|---|---|---|---|---|
| 1 | NIL | | | 1.98 a | 30.55 a | 0.099 c | 1.504 b | 0.028 c | 0.423 b | 0.032 b | 0.500 b |
| 2 | COMP 1 | 1 | 153 | 0.65 c | 11.41 b | 1.218 ab | 21.638 a | 0.461 ab | 8.170 a | 0.044 a | 0.779 a |
| 3 | COMP 1 | 1 | 250 | 0.69 bc | 12.75 b | 1.193 ab | 22.096 a | 0.444 b | 8.230 a | 0.046 a | 0.846 a |
| 4 | COMP 3 | 2.083 | 153 | 0.73 b | 12.88 b | 1.234 a | 21.957 a | 0.487 a | 8.675 a | 0.047 a | 0.839 a |
| 5 | COMP 3 | 2.083 | 250 | 0.74 b | 13.22 b | 1.158 b | 20.725 a | 0.454 b | 8.128 a | 0.047 a | 0.848 a |
| LSD (P = .05) | | | | 0.056 | 2.601 | 0.0634 | 1.8015 | 0.0299 | 0.7482 | 0.0099 | 0.1801 |
| Standard Deviation | | | | 0.041 | 1.888 | 0.0460 | 1.3072 | 0.0217 | 0.5429 | 0.0072 | 0.1307 |
| CV | | | | 4.26 | 11.68 | 4.69 | 7.43 | 5.78 | 8.07 | 16.55 | 17.14 |

Example 4

Introduction

Trial to evaluate sequential applications of Compound 1 in the presence and absence of methyl jasmonate. Applications of Compound 1 were made on 24 November, 2 and 5 December, with morphine crop at early run-up, bud-emergence and early hook stages, respectively. Capsules were harvested from trial plots on 10 February.

TABLE 4a

Effect of treatments on yield parameters.

| Trt No. | Treatment Name | Rate | Rate Unit | Grow Stg | STRAW kg/ha | SEED kg/ha | CAPSULE/ SEED RATIO | YIELD kg/ha |
|---|---|---|---|---|---|---|---|---|
| 1 | NIL | | | | 1737 c | 2088 a | 0.579 d | 3.82 a |
| 2 | COMPOUND 1 | .33 | L/HA | ERU | 2012 a | 1924 b | 0.725 b | 3.93 a |
| 2 | COMPOUND 1 | .33 | L/HA | BE | | | | |
| 2 | COMPOUND 1 | .33 | L/HA | E HOOK | | | | |
| 3 | COMPOUND 1 | .33 | L/HA | ERU | 1927 ab | 1722 c | 0.776 a | 3.65 a |
| 3 | COMPOUND 1 | .33 | L/HA | BE | | | | |
| 3 | METHYL JASMONATE | .3 | L/HA | BE | | | | |
| 3 | COMPOUND 1 | .33 | L/HA | E HOOK | | | | |
| 3 | METHYL JASMONATE | .3 | L/HA | E HOOK | | | | |
| 4 | COMPOUND 1 | .33 | L/HA | ERU | 1918 ab | 1760 bc | 0.757 a | 3.68 a |
| 4 | COMPOUND 1 | .33 | L/HA | BE | | | | |
| 4 | COMPOUND 1 | .33 | L/HA | E HOOK | | | | |
| 4 | METHYL JASMONATE | .6 | L/HA | E HOOK | | | | |
| 5 | METHYL JASMONATE | .6 | L/HA | E HOOK | 1863 b | 1886 bc | 0.685 c | 3.75 a |
| LSD (P = .05) | | | | | 114.5 | 157.8 | 0.0269 | 0.263 |
| Standard Deviation | | | | | 83.1 | 114.5 | 0.0195 | 0.191 |
| CV | | | | | 4.39 | 6.11 | 2.77 | 5.08 |

TABLE 4b

Effect of treatments on alkaloid parameters.

| Trt No. | Treatment Name | Rate | Unit | STRAW MORPHINE % | MORPHINE kg/ha | STRAW THEBAINE % | THEBAINE kg/ha | STRAW O'PAVINE % | ORI-PAVINE kg/ha | STRAW CODEINE % | CODEINE kg/ha |
|---|---|---|---|---|---|---|---|---|---|---|---|
| 1 | NIL | | | 1.91 a | 33.20 a | 0.148 d | 2.550 d | 0.042 c | 0.729 d | 0.044 b | 0.764 bc |
| 2 | COMPOUND 1 | .33 | L/HA | 0.66 c | 13.29 c | 1.332 b | 26.781 b | 0.416 b | 8.366 bc | 0.038 bc | 0.774 b |
| 2 | COMPOUND 1 | .33 | L/HA | | | | | | | | |
| 2 | COMPOUND 1 | .33 | L/HA | | | | | | | | |
| 3 | COMPOUND 1 | .33 | L/HA | 0.50 d | 9.62 d | 1.686 a | 32.496 a | 0.494 a | 9.531 a | 0.035 c | 0.679 bc |
| 3 | COMPOUND 1 | .33 | L/HA | | | | | | | | |
| 3 | METHYL JAS | .3 | L/HA | | | | | | | | |
| 3 | COMPOUND 1 | .33 | L/HA | | | | | | | | |
| 3 | METHYL JAS | .3 | L/HA | | | | | | | | |
| 4 | COMPOUND 1 | .33 | L/HA | 0.48 d | 9.13 d | 1.670 a | 31.999 a | 0.463 ab | 8.873 ab | 0.034 c | 0.644 c |
| 4 | COMPOUND 1 | .33 | L/HA | | | | | | | | |
| 4 | COMPOUND 1 | .33 | L/HA | | | | | | | | |
| 4 | METHYL JAS | .6 | L/HA | | | | | | | | |
| 5 | METHYL JAS | .6 | L/HA | 1.07 b | 19.99 b | 1.028 c | 19.124 c | 0.422 b | 7.853 c | 0.059 a | 1.104 a |
| LSD (P = .05) | | | | 0.071 | 2.616 | 0.0948 | 1.6286 | 0.0478 | 0.9041 | 0.0062 | 0.1154 |
| Standard Deviation | | | | 0.052 | 1.898 | 0.0688 | 1.1817 | 0.0347 | 0.6560 | 0.0045 | 0.0837 |
| CV | | | | 5.61 | 11.13 | 5.87 | 5.23 | 9.45 | 9.28 | 10.61 | 10.56 |

Example 5

Introduction

Trial to evaluate single 1 L/ha applications or split-applications of 0.5 L/ha Compound 1 on morphine crop treated with 1 L/ha Lontrel (applied on 24 November). Compound 1 was applied to plots of treatments 2 and 5 on 25 November, to plots of treatments 3, 4 and 5 on 1 December and to plots of treatment 4 on 4 December (with crop at early run-up, bud-emergence and early hook stages, respectively). Capsules were harvested from trial plots on 23 February.

TABLE 5a

Effect of treatments on yield parameters.

| Trt No. | Treatment Name | Rate | Rate Unit | Grow Stg | STRAW kg/ha | SEED kg/ha | CAPSULE/ SEED RATIO | YIELD kg/ha |
|---|---|---|---|---|---|---|---|---|
| 1 | NIL | | | | 1779 a | 525 a | 2.388 c | 2.30 a |
| 2 | COMPOUND 1 | 1 | L/HA | ERU | 1643 ab | 256 c | 4.687 a | 1.90 b |
| 3 | COMPOUND 1 | 1 | L/HA | BUD-EM | 1566 b | 279 c | 3.981 ab | 1.84 b |
| 4 | COMPOUND 1 | .5 | L/HA | BUD-EM | 1684 ab | 381 b | 3.148 bc | 2.06 b |
| 4 | COMPOUND 1 | .5 | L/HA | E HOOK | | | | |
| 5 | COMPOUND 1 | .5 | L/HA | ERU | 1613 ab | 261 c | 4.404 a | 1.87 b |
| 5 | COMPOUND 1 | .5 | L/HA | BUD-EM | | | | |
| LSD (P = .05) | | | | | 166.6 | 99.2 | 1.0206 | 0.218 |
| Standard Deviation | | | | | 120.9 | 72.0 | 0.7405 | 0.159 |
| CV | | | | | 7.3 | 21.15 | 19.9 | 7.94 |

TABLE 5b

Effect of treatments on alkaloid parameters.

| Trt No. | Treatment Name | Rate | Rate Unit | STRAW MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
| 1 | NIL | | | 1.58 a | 28.12 a | 0.283 c | 5.073 b | 0.040 c | 0.717 c | 0.119 a | 2.111 a |
| 2 | COMPOUND 1 | 1 | L/HA | 0.47 bc | 7.78 c | 1.419 ab | 23.301 a | 0.296 a | 4.856 ab | 0.068 b | 1.126 b |
| 3 | COMPOUND 1 | 1 | L/HA | 0.45 c | 7.08 c | 1.521 a | 23.827 a | 0.266 b | 4.167 b | 0.065 b | 1.016 b |
| 4 | COMPOUND 1 | .5 | L/HA | 0.60 b | 10.05 b | 1.376 b | 23.154 a | 0.296 a | 5.009 a | 0.067 b | 1.119 b |
| 4 | COMPOUND 1 | .5 | L/HA | | | | | | | | |
| 5 | COMPOUND 1 | .5 | L/HA | 0.48 bc | 8.18 bc | 1.498 a | 24.107 a | 0.292 a | 4.715 ab | 0.062 b | 0.995 b |
| 5 | COMPOUND 1 | .5 | L/HA | | | | | | | | |
| LSD (P = .05) | | | | 0.125 | 1.993 | 0.1010 | 2.7234 | 0.0224 | 0.6767 | 0.0087 | 0.2009 |
| Standard Deviation | | | | 0.090 | 1.431 | 0.0733 | 1.9762 | 0.0163 | 0.4910 | 0.0063 | 0.1458 |
| CV | | | | 12.5 | 11.69 | 6.01 | 9.93 | 6.83 | 12.61 | 8.28 | 11.45 |

Example 6

Introduction

Trial to evaluate single 1 L/ha applications or four sequential applications of 0.25 L/ha Compound 1 on morphine crop either treated with Lontrel (on 24 November) or not treated (plots of treatments 1 and 2). Compound 1 sprays were applied to plots of treatments 2 and 5 on 24 and 28 November, 1 and 4 December (early run-up, mid run-up, bud-emergence and early hook, respectively) and to plots of treatments 1 and 4 only on 1 December. Capsules were harvested on 24 February.

TABLE 6a

Effect of treatments on yield parameters.

| Trt No. | Treatment Name | Rate | Rate Unit | Growth Stage | STRAW kg/ha | SEED kg/ha | CAPSULE/ SEED RATIO | YIELD t/ha |
|---|---|---|---|---|---|---|---|---|
| 1 | NIL | | | | 1716 a | 1434 a | 0.826 c | 3.15 a |
| 1 | COMPOUND 1 | 1 | L/HA | | | | | |
| 2 | NIL | | | | 1784 a | 1479 a | 0.839 c | 3.26 a |
| 2 | COMPOUND 1 | .25 | L/HA | ERU | | | | |
| 2 | COMPOUND 1 | .25 | L/HA | MRU | | | | |
| 2 | COMPOUND 1 | .25 | L/HA | BUD-EM | | | | |
| 2 | COMPOUND 1 | .25 | L/HA | HOOK | | | | |
| 3 | LONTREL | 1 | L/HA | ERU | 1290 b | 204 b | 4.754 b | 1.49 b |
| 3 | NIL | | | | | | | |
| 4 | LONTREL | 1 | L/HA | ERU | 1207 b | 127 b | 7.244 a | 1.34 b |
| 4 | COMPOUND 1 | 1 | L/HA | BUD-EM | | | | |
| 5 | LONTREL | 1 | L/HA | ERU | 1105 b | 119 b | 7.231 a | 1.23 b |

TABLE 6a-continued

Effect of treatments on yield parameters.

| Trt No. | Treatment Name | Rate | Rate Unit | Growth Stage | STRAW kg/ha | SEED kg/ha | CAPSULE/ SEED RATIO | YIELD t/ha |
|---|---|---|---|---|---|---|---|---|
| 5 | COMPOUND 1 | .25 | L/HA | ERU | | | | |
| 5 | COMPOUND 1 | .25 | L/HA | MRU | | | | |
| 5 | COMPOUND 1 | .25 | L/HA | BUD-EM | | | | |
| 5 | COMPOUND 1 | .25 | L/HA | HOOK | | | | |
| LSD (P = .05) | | | | | 252.6 | 188.1 | 2.1250 | 0.421 |
| Standard Deviation | | | | | 209.8 | 156.2 | 1.7645 | 0.349 |
| CV | | | | | 14.77 | 23.21 | 42.22 | 16.69 |

TABLE 6b

Effect of treatments on alkaloid parameters.

| Trt No. | Treatment Name | Rate | Rate Unit | STRAW MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
| 1 | NIL | | | 0.50 b | 8.61 b | 1.248 b | 21.612 a | 0.318 b | 5.532 b | 0.03 c | 0.575 b |
| 1 | COMPOUND 1 | 1 | L/HA | | | | | | | | |
| 2 | NIL | | | 0.54 b | 9.64 b | 1.218 b | 21.841 a | 0.375 a | 6.730 a | 0.04 c | 0.757 b |
| 2 | COMPOUND 1 | .25 | L/HA | | | | | | | | |
| 2 | COMPOUND 1 | .25 | L/HA | | | | | | | | |
| 2 | COMPOUND 1 | .25 | L/HA | | | | | | | | |
| 2 | COMPOUND 1 | .25 | L/HA | | | | | | | | |
| 3 | LONTREL | 1 | L/HA | 1.55 a | 20.00 a | 0.262 c | 3.373 b | 0.043 c | 0.549 d | 0.14 a | 1.785 a |
| 3 | NIL | | | | | | | | | | |
| 4 | LONTREL | 1 | L/HA | 0.39 c | 4.73 c | 1.698 a | 20.457 a | 0.288 b | 3.474 c | 0.06 b | 0.720 b |
| 4 | COMPOUND 1 | 1 | L/HA | | | | | | | | |
| 5 | LONTREL | 1 | L/HA | 0.39 c | 4.34 c | 1.639 a | 18.101 a | 0.361 a | 3.985 c | 0.06 b | 0.659 b |
| 5 | COMPOUND 1 | .25 | L/HA | | | | | | | | |
| 5 | COMPOUND 1 | .25 | L/HA | | | | | | | | |
| 5 | COMPOUND 1 | .25 | L/HA | | | | | | | | |
| 5 | COMPOUND 1 | .25 | L/HA | | | | | | | | |
| LSD (P = .05) | | | | 0.080 | 2.011 | 0.1021 | 3.9775 | 0.0362 | 1.1966 | 0.014 | 0.2379 |
| Standard Deviation | | | | 0.066 | 1.670 | 0.0848 | 3.3026 | 0.0300 | 0.9936 | 0.012 | 0.1975 |
| CV | | | | 9.84 | 17.65 | 6.99 | 19.34 | 10.84 | 24.51 | 17.85 | 21.96 |

Example 7

Introduction

Trial to evaluate the effect of 1 L/ha Compound 1 on a morphine cultivar (V100) and two thebaine cultivars (T17 and T22). Plots were sown on 8 September. Six plots of each cultivar remained untreated and six were sprayed with 0.5 L/ha Compound 1 on 20 and 28 November, with crop at early and late run-up, respectively. Capsules were harvested on 9 February.

TABLE 7a

Effect of treatments on yield parameters.

| Trt No. | Treatment Name | Rate | Rate Unit | Grow Stg | STRAW kg/ha | SEED kg/ha | CAPSULE/ SEED RATIO | YIELD t/ha |
|---|---|---|---|---|---|---|---|---|
| 1 | NIL | | | | 1738 a | 2015 a | 0.600 e | 3.75 a |
| 1 | V100 | | | | | | | |
| 2 | NIL | | | | 1649 a | 1595 c | 0.717 d | 3.24 ab |
| 2 | T17 | | | | | | | |
| 3 | NIL | | | | 1636 a | 1933 ab | 0.588 e | 3.57 a |
| 3 | T22 | | | | | | | |
| 4 | COMPOUND 1 | .5 | L/HA | ERU | 1898 a | 1740 bc | 0.761 c | 3.64 a |

TABLE 7a-continued

Effect of treatments on yield parameters.

| Trt No. | Treatment Name | Rate | Rating Unit Rate Unit | Grow Stg | STRAW kg/ha | SEED kg/ha | CAPSULE/ SEED RATIO | YIELD t/ha |
|---|---|---|---|---|---|---|---|---|
| 4 | COMPOUND 1 | .5 | L/HA | LRU | | | | |
| 4 | V100 | | | | | | | |
| 5 | COMPOUND 1 | .5 | L/HA | ERU | 1643 a | 1174 d | 0.979 a | 2.82 b |
| 5 | COMPOUND 1 | .5 | L/HA | LRU | | | | |
| 5 | T17 | | | | | | | |
| 6 | COMPOUND 1 | .5 | L/HA | ERU | 1767 a | 1532 c | 0.799 b | 3.30 ab |
| 6 | COMPOUND 1 | .5 | L/HA | LRU | | | | |
| 6 | T22 | | | | | | | |
| LSD (P = .05) | | | | | 239.1 | 259.0 | 0.0330 | 0.490 |
| Standard Deviation | | | | | 201.1 | 217.7 | 0.0278 | 0.412 |
| CV | | | | | 11.68 | 13.08 | 3.75 | 12.17 |

TABLE 7b

Effect of treatments on alkaloid parameters.

| TrT No. | Trt Name | Rate | Rating Unit Rate Unit | STRAW MORPHINE % | STRAW MORPHINE kg/ha | THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
| 1 | NIL | | | 1.67 a | 29.03 a | 0.075 e | 1.292 c | 0.021 f | 0.370 e | 0.036 c | 0.623 c |
| 1 | V100 | | | | | | | | | | |
| 2 | NIL | | | 0.53 b | 8.79 b | 0.829 d | 13.676 b | 0.223 e | 3.685 d | 0.061 a | 1.008 a |
| 2 | T17 | | | | | | | | | | |
| 3 | NIL | | | 0.09 de | 1.42 c | 0.902 c | 14.753 b | 0.626 a | 10.208 a | 0.007 e | 0.115 e |
| 3 | T22 | | | | | | | | | | |
| 4 | COMP 1 | .5 | L/HA | 0.45 c | 8.59 b | 1.246 b | 23.617 a | 0.33 c | 6.282 b | 0.042 b | 0.805 b |
| 4 | COMP 1 | .5 | L/HA | | | | | | | | |
| 4 | V100 | | | | | | | | | | |
| 5 | COMP 1 | .5 | L/HA | 0.10 d | 1.70 c | 1.431 a | 23.532 a | 0.284 d | 4.664 c | 0.022 d | 0.368 d |
| 5 | COMP 1 | .5 | L/HA | | | | | | | | |
| 5 | T17 | | | | | | | | | | |
| 6 | COMP 1 | .5 | L/H | 0.04 e | 0.78 c | 1.228 b | 21.717 a | 0.385 b | 6.842 b | 0.006 e | 0.106 e |
| 6 | COMP 1 | .5 | L/HA | | | | | | | | |
| 6 | T22 | | | | | | | | | | |
| LSD (P = .05) | | | | 0.049 | 2.332 | 0.0615 | 2.9185 | 0.0246 | 0.8807 | 0.0057 | 0.1285 |
| Standard Deviation | | | | 0.041 | 1.96 | 0.0517 | 2.4539 | 0.0207 | 0.7405 | 0.0048 | 0.108 |
| CV | | | | 8.56 | 23.38 | 5.43 | 14.93 | 6.64 | 13.86 | 16.48 | 21.43 |

Example 8

Introduction

Trial to evaluate the effect of 1 L/ha Compound 1 on a morphine cultivar (V100) and two thebaine cultivars (T17 and T22). Plots were sown on 8 September and all were sprayed with 1 L/ha Clopyralid (Lontrel™) on 7 November, with crop at 12-14 leaf/row cover. Six plots of each cultivar remained untreated and six were sprayed with 0.5 L/ha Compound 1 on 20 and 28 November, with crop at early and late run-up, respectively. Capsules were harvested on 17 February.

TABLE 8a

Effect of treatments on yield parameters.

| Trt No. | Treatment Name | Rate | Rating Unit Rate Unit | Growth Stage | STRAW kg/ha | SEED kg/ha | CAPSULE/ SEED RATIO | YIELD t/ha |
|---|---|---|---|---|---|---|---|---|
| 1 | NIL | | | | 2235 a | 251 a | 7.153 a | 2.49 a |
| 1 | V100 | | | | | | | |
| 2 | NIL | | | | 1850 b | 257 a | 5.788 a | 2.11 c |

TABLE 8a-continued

Effect of treatments on yield parameters.

| Trt No. | Treatment Name | Rate | Rate Unit | Growth Stage | STRAW kg/ha | SEED kg/ha | CAPSULE/ SEED RATIO | YIELD t/ha |
|---|---|---|---|---|---|---|---|---|
| 2 | T17 | | | | | | | |
| 3 | NIL | | | | 2214 a | 251 a | 6.625 a | 2.46 a |
| 3 | T22 | | | | | | | |
| 4 | COMPOUND 1 | .5 | L/HA | ERU | 2043 a | 152 a | 10.126 a | 2.19 bc |
| 4 | COMPOUND 1 | .5 | L/HA | LRU | | | | |
| 4 | V100 | | | | | | | |
| 5 | COMPOUND 1 | .5 | L/HA | ERU | 1842 b | 168 a | 10.310 a | 2.01 c |
| 5 | COMPOUND 1 | .5 | L/HA | LRU | | | | |
| 5 | T17 | | | | | | | |
| 6 | COMPOUND 1 | .5 | L/HA | ERU | 2144 a | 262 a | 7.244 a | 2.40 ab |
| 6 | COMPOUND 1 | .5 | L/HA | LRU | | | | |
| 6 | T22 | | | | | | | |
| LSD (P = .05) | | | | | 184.2 | 109.5 | 4.6076 | 0.234 |
| Standard Deviation | | | | | 154.9 | 92.0 | 3.8741 | 0.197 |
| CV | | | | | 7.54 | 41.21 | 49.2 | 8.65 |

TABLE 8b

Effect of treatments on alkaloid parameters.

| Trt No. | Treatment Name | Rate | Rate Unit | STRAW MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
| 1 | NIL | | | 1.53 a | 34.23 a | 0.192 d | 4.298 d | 0.026 e | 0.594 d | 0.087 b | 1.947 a |
| 1 | V100 | | | | | | | | | | |
| 2 | NIL | | | 0.57 b | 10.51 b | 1.054 c | 19.495 c | 0.201 d | 3.709 c | 0.102 a | 1.895 a |
| 2 | T17 | | | | | | | | | | |
| 3 | NIL | | | 0.08 e | 1.82 e | 1.043 c | 23.007 b | 0.586 a | 13.002 a | 0.007 e | 0.151 d |
| 3 | T22 | | | | | | | | | | |
| 4 | COMPOUND 1 | 1 | L/HA | 0.41 c | 8.47 c | 1.372 b | 28.023 a | 0.313 bc | 6.414 b | 0.053 c | 1.073 b |
| 4 | COMPOUND 1 | .5 | L/HA | | | | | | | | |
| 4 | V100 | | | | | | | | | | |
| 5 | COMPOUND 1 | 1 | L/HA | 0.15 d | 2.82 d | 1.618 a | 29.729 a | 0.269 c | 4.952 c | 0.029 d | 0.520 c |
| 5 | COMPOUND 1 | .5 | L/HA | | | | | | | | |
| 5 | T17 | | | | | | | | | | |
| 6 | COMPOUND 1 | 1 | L/HA | 0.05 f | 0.97 f | 1.321 b | 28.326 a | 0.348 b | 7.485 b | 0.004 e | 0.073 d |
| 6 | COMPOUND 1 | .5 | L/HA | | | | | | | | |
| 6 | T22 | | | | | | | | | | |
| LSD (P = .05) | | | | 0.030 | 0.812 | 0.0882 | 2.5623 | 0.0478 | 1.3342 | 0.0084 | 0.1584 |
| Standard Deviation | | | | 0.025 | 0.683 | 0.0741 | 2.1544 | 0.0402 | 1.1218 | 0.0070 | 0.1332 |
| CV | | | | 5.39 | 6.97 | 6.74 | 9.73 | 13.85 | 18.62 | 15.03 | 14.12 |

Example 9

Introduction

Trial to compare the effect of 1 L/ha Compound 1 applied at early run-up with 1 and 2 L/ha applied over four dates and 1.5 L/ha, applied in different variations over four dates in Lontrel-treated thebaine crop. Sprays were applied on 19, 24 and 28 November and 4 December, with crop at ground cover, early run-up, late run-up and hook stages, respectively. Capsules were harvested from the trial and from crop adjacent to the trial (Nil) on 18 February.

TABLE 9a

Effect of treatments on yield parameters.

| Trt No. | Treatment Name | Rate | Rate Unit | Growth Stage | STRAW kg/ha | SEED kg/ha | CAPSULE/ SEED RATIO | YIELD kg/ha |
|---|---|---|---|---|---|---|---|---|
| | NIL | | | | 1505 | 1140 | 0.937 | 2.65 |
| 1 | COMPOUND 1 | 1 | L/HA | ERU | 1493 a | 902 a | 1.147 a | 2.39 a |
| 2 | COMPOUND 1 | .25 | L/HA | GC | 1536 a | 952 a | 1.134 a | 2.49 a |
| 2 | COMPOUND 1 | .25 | L/HA | ERU | | | | |
| 2 | COMPOUND 1 | .25 | L/HA | LRU | | | | |
| 2 | COMPOUND 1 | .25 | L/HA | HOOK | | | | |
| 3 | COMPOUND 1 | .5 | L/HA | GC | 1631 a | 970 a | 1.186 a | 2.60 a |
| 3 | COMPOUND 1 | .5 | L/HA | ERU | | | | |
| 3 | COMPOUND 1 | .5 | L/HA | LRU | | | | |
| 3 | COMPOUND 1 | .5 | L/HA | HOOK | | | | |
| 4 | COMPOUND 1 | .5 | L/HA | GC | 1490 a | 930 a | 1.125 a | 2.42 a |
| 4 | COMPOUND 1 | .5 | L/HA | ERU | | | | |
| 4 | COMPOUND 1 | .25 | L/HA | LRU | | | | |
| 4 | COMPOUND 1 | .25 | L/HA | HOOK | | | | |
| 5 | COMPOUND 1 | .25 | L/HA | GC | 1566 a | 981 a | 1.120 a | 2.55 a |
| 5 | COMPOUND 1 | .25 | L/HA | ERU | | | | |
| 5 | COMPOUND 1 | .5 | L/HA | LRU | | | | |
| 5 | COMPOUND 1 | .5 | L/HA | HOOK | | | | |
| LSD (P = .05) | | | | | 208.4 | 164.6 | 0.1414 | 0.341 |
| Standard Deviation | | | | | 151.3 | 119.4 | 0.1026 | 0.248 |
| CV | | | | | 9.8 | 12.61 | 8.98 | 9.95 |

TABLE 9b

Effect of treatments on alkaloid parameters.

| Trt No. | Treatment Name | Rate | Rate Unit | STRAW MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
| | NIL | | | 0.74 | 11.12 | 0.995 | 15.070 | 0.181 | 2.767 | 0.100 | 1.478 |
| 1 | COMPOUND 1 | 1 | L/HA | 0.19 a | 2.75 a | 1.584 b | 23.631 c | 0.321 a | 4.846 a | 0.029 a | 0.418 a |
| 2 | COMPOUND 1 | .25 | L/HA | 0.17 a | 2.63 a | 1.563 b | 24.066 bc | 0.301 ab | 4.642 a | 0.027 a | 0.413 a |
| 2 | COMPOUND 1 | .25 | L/HA | | | | | | | | |
| 2 | COMPOUND 1 | .25 | L/HA | | | | | | | | |
| 2 | COMPOUND 1 | .25 | L/HA | | | | | | | | |
| 3 | COMPOUND 1 | .5 | L/HA | 0.12 b | 2.03 b | 1.733 a | 28.265 a | 0.273 b | 4.464 a | 0.026 a | 0.417 a |
| 3 | COMPOUND 1 | .5 | L/HA | | | | | | | | |
| 3 | COMPOUND 1 | .5 | L/HA | | | | | | | | |
| 3 | COMPOUND 1 | .5 | L/HA | | | | | | | | |
| 4 | COMPOUND 1 | .5 | L/HA | 0.14 b | 2.13 b | 1.712 a | 25.470 abc | 0.304 ab | 4.541 a | 0.027 a | 0.401 a |
| 4 | COMPOUND 1 | .5 | L/HA | | | | | | | | |
| 4 | COMPOUND 1 | .25 | L/HA | | | | | | | | |
| 4 | COMPOUND 1 | .25 | L/HA | | | | | | | | |
| 5 | COMPOUND 1 | .25 | L/HA | 0.13 b | 1.96 b | 1.784 a | 27.899 ab | 0.289 ab | 4.516 a | 0.026 a | 0.398 a |
| 5 | COMPOUND 1 | .25 | L/HA | | | | | | | | |
| 5 | COMPOUND 1 | .5 | L/HA | | | | | | | | |
| 5 | COMPOUND 1 | .5 | L/HA | | | | | | | | |
| LSD (P = .05) | | | | 0.023 | 0.380 | 0.0938 | 3.8842 | 0.0308 | 0.8415 | 0.0054 | 0.0361 |
| Standard Deviation | | | | 0.017 | 0.276 | 0.0681 | 2.8185 | 0.0223 | 0.6106 | 0.0039 | 0.0262 |
| CV | | | | 11.21 | 11.98 | 4.06 | 10.9 | 7.51 | 13.27 | 14.58 | 6.39 |

Example 10

Introduction

Trial to compare the effect of 1 and 1.5 L/ha rates of Compound 1 applied in various configurations over three dates on Lontrel-treated thebaine crop. Sprays were applied on 24 and 28 November and 4 December, with crop at early run-up, late run-up and hook stages, respectively. Capsules were harvested from plots and from crop adjacent to the trial (Nil) on 18 February.

TABLE 10a

Effect of treatments on yield parameters.

| Trt No. | Treatment Name | Rate | Rating Unit Rate Unit | Growth Stage | STRAW kg/ha | SEED kg/ha | CAPSULE/ SEED RATIO | YIELD kg/ha |
|---|---|---|---|---|---|---|---|---|
|  | NIL |  |  |  | 1505 | 1140 | 0.937 | 2.65 |
| 1 | COMPOUUD 1 | .5 | L/HA | ERU | 1693 a | 822 a | 1.444 ab | 2.52 a |
| 1 | COMPOUND 1 | .25 | L/HA | LRU |  |  |  |  |
| 1 | COMPOUND 1 | .25 | L/HA | HOOK |  |  |  |  |
| 2 | COMPOUND 1 | .25 | L/HA | ERU | 1591 a | 831 a | 1.337 c | 2.42 a |
| 2 | COMPOUND 1 | .25 | L/HA | LRU |  |  |  |  |
| 2 | COMPOUND 1 | .5 | L/HA | HOOK |  |  |  |  |
| 3 | COMPOUND 1 | .25 | L/HA | ERU | 1706 a | 804 a | 1.484 a | 2.51 a |
| 3 | COMPOUND 1 | .5 | L/HA | LRU |  |  |  |  |
| 3 | COMPOUND 1 | .25 | L/HA | HOOK |  |  |  |  |
| 4 | COMPOUND 1 | 1 | L/HA | ERU | 1598 a | 818 a | 1.362 bc | 2.42 a |
| 4 | COMPOUND 1 | .25 | L/HA | LRU |  |  |  |  |
| 4 | COMPOUND 1 | .25 | L/HA | HOOK |  |  |  |  |
| 5 | COMPOUND 1 | .25 | L/HA | ERU | 1614 a | 750 a | 1.518 a | 2.36 a |
| 5 | COMPOUND 1 | .25 | L/HA | LRU |  |  |  |  |
| 5 | COMPOUND 1 | 1 | L/HA | HOOK |  |  |  |  |
| LSD (P = .05) |  |  |  |  | 141.7 | 86.5 | 0.1003 | 0.217 |
| Standard Deviation |  |  |  |  | 102.8 | 62.7 | 0.0728 | 0.157 |
| CV |  |  |  |  | 6.27 | 7.79 | 5.09 | 6.43 |

TABLE 10b

Effect of treatments on alkaloid parameters.

| Trt No. | Treatment Name | Rate | Rating Unit Rate Unit | STRAW MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
|  | NIL |  |  | 0.74 | 11.12 | 0.995 | 15.070 | 0.181 | 2.767 | 0.100 | 1.478 |
| 1 | COMP 1 | .5 | L/HA | 0.16 a | 2.72 a | 1.567 b | 26.545 a | 0.324 a | 5.497 a | 0.024 a | 0.408 a |
| 1 | COMP 1 | .25 | L/HA |  |  |  |  |  |  |  |  |
| 1 | COMP 1 | .25 | L/HA |  |  |  |  |  |  |  |  |
| 2 | COMP 1 | .25 | L/HA | 0.15 ab | 2.44 ab | 1.629 ab | 25.889 a | 0.310 a | 4.935 ab | 0.023 a | 0.364 ab |
| 2 | COMP 1 | .25 | L/HA |  |  |  |  |  |  |  |  |
| 2 | COMP 1 | .5 | L/HA |  |  |  |  |  |  |  |  |
| 3 | COMP 1 | .25 | L/HA | 0.15 ab | 2.50 ab | 1.609 b | 27.469 a | 0.324 a | 5.531 a | 0.023 a | 0.390 ab |
| 3 | COMP 1 | .5 | L/HA |  |  |  |  |  |  |  |  |
| 3 | COMP 1 | .25 | L/HA |  |  |  |  |  |  |  |  |
| 4 | COMP 1 | 1 | L/HA | 0.14 ab | 2.27 ab | 1.637 ab | 26.153 a | 0.313 a | 5.004 ab | 0.021 a | 0.333 b |
| 4 | COMP 1 | .25 | L/HA |  |  |  |  |  |  |  |  |
| 4 | COMP 1 | .25 | L/HA |  |  |  |  |  |  |  |  |
| 5 | COMP 1 | .25 | L/HA | 0.12 b | 1.94 b | 1.701 a | 27.451 a | 0.269 b | 4.356 b | 0.023 a | 0.361 ab |
| 5 | COMP 1 | .25 | L/HA |  |  |  |  |  |  |  |  |
| 5 | COMP 1 | 1 | L/HA |  |  |  |  |  |  |  |  |
| LSD (P = .05) |  |  |  | 0.034 | 0.555 | 0.0849 | 2.3595 | 0.0210 | 0.6203 | 0.0044 | 0.0667 |
| Standard Deviation |  |  |  | 0.024 | 0.403 | 0.0616 | 1.7121 | 0.0153 | 0.4501 | 0.0032 | 0.0484 |
| CV |  |  |  | 16.91 | 16.97 | 3.78 | 6.41 | 4.95 | 8.89 | 14.19 | 13.04 |

Example 11

Introduction

Trial to compare the effect of 1 L/ha Compound 1 applied at late bud-emergence/early hook with 1 and 2 L/ha applied over four dates and 1.5 L/ha, applied in different variations over four dates in Lontrel-treated thebaine crop. Sprays were applied on 8, 15, 19 and 23 December, with crop at ground cover, run-up, late bud-emergence and hook stages, respectively. Capsules were harvested from plots and crop adjacent to trial (Nil) on 19. February.

TABLE 11a

Effect of treatments on yield parameters.

| Trt No. | Treatment Name | Rate | Rate Unit | Growth Stage | STRAW kg/ha | SEED kg/ha | CAPSULE/ SEED RATIO | YIELD kg/ha |
|---|---|---|---|---|---|---|---|---|
|  | NIL |  |  |  | 836 | 510 | 1.139 | 1.35 |
| 1 | COMPOUND 1 | 1 | L/HA | RU | 919 a | 404 a | 1.794 a | 1.32 a |
| 2 | COMPOUND 1 | .25 | L/HA | GC | 858 a | 328 a | 1.951 a | 1.18 a |
| 2 | COMPOUND 1 | .25 | L/HA | RUN-UP |  |  |  |  |
| 2 | COMPOUND 1 | .25 | L/HA | LBE |  |  |  |  |
| 2 | COMPOUND 1 | .25 | L/HA | HOOK |  |  |  |  |
| 3 | COMPOUND 1 | .5 | L/HA | GC | 955 a | 401 a | 1.718 a | 1.36 a |
| 3 | COMPOUND 1 | .5 | L/HA | RUN-UP |  |  |  |  |
| 3 | COMPOUND 1 | .5 | L/HA | LBE |  |  |  |  |
| 3 | COMPOUND 1 | .5 | L/HA | HOOK |  |  |  |  |
| 4 | COMPOUND 1 | .5 | L/HA | GC | 830 a | 342 a | 1.799 a | 1.17 a |
| 4 | COMPOUND 1 | .5 | L/HA | RUN-UP |  |  |  |  |
| 4 | COMPOUND 1 | .25 | L/HA | LBE |  |  |  |  |
| 4 | COMPOUND 1 | .25 | L/HA | HOOK |  |  |  |  |
| 5 | COMPOUND 1 | .25 | L/HA | GC | 865 a | 306 a | 2.018 a | 1.17 a |
| 5 | COMPOUND 1 | .25 | L/HA | RUN-UP |  |  |  |  |
| 5 | COMPOUND 1 | .5 | L/HA | LBE |  |  |  |  |
| 5 | COMPOUND 1 | .5 | L/HA | HOOK |  |  |  |  |
| LSD (P = .05) |  |  |  |  | 151.9 | 119.4 | 0.2987 | 0.256 |
| Standard Deviation |  |  |  |  | 110.2 | 86.7 | 0.2167 | 0.186 |
| CV |  |  |  |  | 12.45 | 24.35 | 11.68 | 14.97 |

TABLE 11b

Effect of treatments on alkaloid parameters.

| Trt No. | Treatment Name | Rate | Rate Unit | STRAW MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
|  | NIL |  |  | 0.51 | 4.31 | 1.246 | 10.430 | 0.152 | 1.272 | 0.095 | 0.799 |
| 1 | COMPOUND 1 | 1 | L/HA | 0.10 a | 0.95 a | 1.696 ab | 15.576 ab | 0.170 a | 1.556 a | 0.019 a | 0.176 a |
| 2 | COMPOUND 1 | .25 | L/HA | 0.06 b | 0.56 b | 1.658 ab | 14.216 ab | 0.181 a | 1.560 a | 0.022 a | 0.193 a |
| 2 | COMPOUND 1 | .25 | L/HA |  |  |  |  |  |  |  |  |
| 2 | COMPOUND 1 | .25 | L/HA |  |  |  |  |  |  |  |  |
| 2 | COMPOUND 1 | .25 | L/HA |  |  |  |  |  |  |  |  |
| 3 | COMPOUND 1 | .5 | L/HA | 0.05 c | 0.46 b | 1.773 a | 16.965 a | 0.138 c | 1.314 b | 0.022 a | 0.213 a |
| 3 | COMPOUND 1 | .5 | L/HA |  |  |  |  |  |  |  |  |
| 3 | COMPOUND 1 | .5 | L/HA |  |  |  |  |  |  |  |  |
| 3 | COMPOUND 1 | .5 | L/HA |  |  |  |  |  |  |  |  |
| 4 | COMPOUND 1 | .5 | L/HA | 0.05 c | 0.40 b | 1.581 b | 12.993 b | 0.151 b | 1.243 b | 0.021 a | 0.170 a |
| 4 | COMPOUND 1 | .5 | L/HA |  |  |  |  |  |  |  |  |
| 4 | COMPOUND 1 | .25 | L/HA |  |  |  |  |  |  |  |  |
| 4 | COMPOUND 1 | .25 | L/HA |  |  |  |  |  |  |  |  |
| 5 | COMPOUND 1 | .25 | L/HA | 0.05 c | 0.42 b | 1.748 a | 15.371 ab | 0.144 bc | 1.251 b | 0.022 a | 0.194 a |
| 5 | COMPOUND 1 | .25 | L/HA |  |  |  |  |  |  |  |  |
| 5 | COMPOUND 1 | .5 | L/HA |  |  |  |  |  |  |  |  |
| 5 | COMPOUND 1 | .5 | L/HA |  |  |  |  |  |  |  |  |
| LSD (P = .05) |  |  |  | 0.014 | 0.196 | 0.1305 | 2.6228 | 0.0118 | 0.2309 | 0.0052 | 0.0492 |
| Standard Deviation |  |  |  | 0.010 | 0.142 | 0.0947 | 1.9032 | 0.0086 | 0.1676 | 0.0038 | 0.0357 |
| CV |  |  |  | 16.92 | 25.55 | 5.6 | 12.67 | 5.49 | 12.1 | 17.63 | 18.86 |

Example 12

Introduction

Trial to compare the effect of 1 and 10.5 L/ha rates of Compound 1 applied over three dates in different configurations, in Lontrel-treated thebaine crop. Sprays were applied on 26 November, 2 and 8 December, with crop at run-up, bud-emergence and hook stages, respectively. Capsules were harvested from plots and crop adjacent to the trial (Nil) on 9 February.

TABLE 12a

Effect of treatments on yield parameters.

| Trt No. | Treatment Name | Rate | Rating Unit Rate Unit | Growth Stage | STRAW kg/ha | SEED kg/ha | CAPSULE/ SEED RATIO | YIELD kg/ha |
|---|---|---|---|---|---|---|---|---|
|  | NIL |  |  |  | 1713 | 65 | 36.130 | 1.78 |
| 1 | COMPOUND 1 | .5 | L/HA | RUN-UP | 1589 a | 17 a | 110.973 a | 1.60 a |
| 1 | COMPOUND 1 | .25 | L/HA | BUD-EM |  |  |  |  |
| 1 | COMPOUND 1 | .25 | L/HA | HOOK |  |  |  |  |
| 2 | COMPOUND 1 | .25 | L/HA | RUN-UP | 1609 a | 16 a | 122.756 a | 1.63 a |
| 2 | COMPOUND 1 | .25 | L/HA | BUD-EM |  |  |  |  |
| 2 | COMPOUND 1 | .5 | L/HA | HOOK |  |  |  |  |
| 3 | COMPOUND 1 | .25 | L/HA | RUN-UP | 1669 a | 11 a | 274.635 a | 1.68 a |
| 3 | COMPOUND 1 | .5 | L/HA | BUD-EM |  |  |  |  |
| 3 | COMPOUND 1 | .25 | L/HA | HOOK |  |  |  |  |
| 4 | COMPOUND 1 | 1 | L/HA | RUN-UP | 1625 a | 13 a | 168.578 a | 1.64 a |
| 4 | COMPOUND 1 | .25 | L/HA | BUD-EM |  |  |  |  |
| 4 | COMPOUND 1 | .25 | L/HA | HOOK |  |  |  |  |
| 5 | COMPOUND 1 | .25 | L/HA | RUN-UP | 1600 a | 12 a | 194.551 a | 1.61 a |
| 5 | COMPOUND 1 | .25 | L/HA | BUD-EM |  |  |  |  |
| 5 | COMPOUND 1 | 1 | L/HA | HOOK |  |  |  |  |
| LSD (P = .05) |  |  |  |  | 89.1 | 11.2 | 215.3764 | 0.082 |
| Standard Deviation |  |  |  |  | 64.7 | 8.1 | 156.2827 | 0.059 |
| CV |  |  |  |  | 4.0 | 59.55 | 89.66 | 3.63 |

TABLE 12b

Effect of treatments on alkaloid parameters.

| Trt No. | Treatment Name | Rate | Rating Unit Rate Unit | STRAW MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
|  | NIL |  |  | 0.67 | 11.39 | 1.210 | 20.732 | 0.222 | 3.786 | 0.149 | 2.563 |
| 1 | COMP 1 | .5 | L/HA | 0.11 a | 1.72 ab | 2.053 b | 32.598 a | 0.291 a | 4.655 ab | 0.026 a | 0.401 b |
| 1 | COMP 1 | .25 | L/HA |  |  |  |  |  |  |  |  |
| 1 | COMP 1 | .25 | L/HA |  |  |  |  |  |  |  |  |
| 2 | COMP 1 | .25 | L/HA | 0.10 ab | 1.57 ab | 2.089 ab | 33.547 a | 0.278 ab | 4.428 ab | 0.026 a | 0.408 b |
| 2 | COMP 1 | .25 | L/HA |  |  |  |  |  |  |  |  |
| 2 | COMP 1 | .5 | L/HA |  |  |  |  |  |  |  |  |
| 3 | COMP 1 | .25 | L/HA | 0.11 a | 1.78 a | 2.044 b | 34.128 a | 0.285 a | 4.799 a | 0.029 a | 0.473 a |
| 3 | COMP 1 | .5 | L/HA |  |  |  |  |  |  |  |  |
| 3 | COMP 1 | .25 | L/HA |  |  |  |  |  |  |  |  |
| 4 | COMP 1 | 1 | L/HA | 0.10 ab | 1.59 ab | 2.084 ab | 33.809 a | 0.253 b | 4.129 b | 0.027 a | 0.430 ab |
| 4 | COMP 1 | .25 | L/HA |  |  |  |  |  |  |  |  |
| 4 | COMP 1 | .25 | L/HA |  |  |  |  |  |  |  |  |
| 5 | COMP 1 | .25 | L/HA | 0.09 b | 1.51 b | 2.164 a | 34.682 a | 0.251 b | 4.026 b | 0.026 a | 0.406 b |
| 5 | COMP 1 | .25 | L/HA |  |  |  |  |  |  |  |  |
| 5 | COMP 1 | 1 | L/HA |  |  |  |  |  |  |  |  |
| LSD (P = .05) |  |  |  | 0.010 | 0.200 | 0.0904 | 2.2771 | 0.0311 | 0.5972 | 0.0034 | 0.0574 |
| Standard Deviation |  |  |  | 0.007 | 0.145 | 0.0656 | 1.6523 | 0.0226 | 0.4334 | 0.0024 | 0.0416 |
| CV |  |  |  | 7.42 | 8.87 | 3.14 | 4.9 | 8.31 | 9.83 | 9.2 | 9.82 |

Example 13

Introduction

Trial to compare the effect of 1 L/ha Compound 1 applied at early run-up with 1 and 2 L/ha applied over four dates and 10.5 L/ha, applied in different variations over four dates in Lontrel-treated thebaine crop. Sprays were applied on 4, 8, 15 and 19 December, with crop at ground cover, early run-up, bud-emergence and hook stages, respectively. Capsules were harvested from the trial and from crop adjacent to the trial (Nil) on 2 March.

TABLE 13a

Effect of treatments on yield parameters.

| Trt No. | Treatment Name | Rate | Rate Unit | Grow Stg | STRAW kg/ha | SEED kg/ha | CAPSULE/SEED RATIO | YIELD kg/ha |
|---|---|---|---|---|---|---|---|---|
|  | NIL |  |  |  | 1393 | 862 | 1.142 | 2.26 |
| 1 | COMPOUND 1 | 1 | L/HA | ERU | 1249 a | 478 a | 1.895 a | 1.73 a |
| 2 | COMPOUND 1 | .25 | L/HA | GC | 1182 a | 498 a | 1.760 a | 1.68 a |
| 2 | COMPOUND 1 | .25 | L/HA | ERU |  |  |  |  |
| 2 | COMPOUND 1 | .25 | L/HA | BUD-EM |  |  |  |  |
| 2 | COMPOUND 1 | .25 | L/HA | HOOK |  |  |  |  |
| 3 | COMPOUND 1 | .5 | L/HA | GC | 1246 a | 502 a | 1.939 a | 1.75 a |
| 3 | COMPOUND 1 | .5 | L/HA | ERU |  |  |  |  |
| 3 | COMPOUND 1 | .5 | L/HA | BUD-EM |  |  |  |  |
| 3 | COMPOUND 1 | .5 | L/HA | HOOK |  |  |  |  |
| 4 | COMPOUND 1 | .5 | L/HA | GC | 1196 a | 505 a | 1.775 a | 1.70 a |
| 4 | COMPOUND 1 | .5 | L/HA | ERU |  |  |  |  |
| 4 | COMPOUND 1 | .25 | L/HA | BUD-EM |  |  |  |  |
| 4 | COMPOUND 1 | .25 | L/HA | HOOK |  |  |  |  |
| 5 | COMPOUND 1 | .25 | L/HA | GC | 1229 a | 533 a | 1.731 a | 1.76 a |
| 5 | COMPOUND 1 | .25 | L/HA | ERU |  |  |  |  |
| 5 | COMPOUND 1 | .5 | L/HA | BUD-EM |  |  |  |  |
| 5 | COMPOUND 1 | .5 | L/HA | HOOK |  |  |  |  |
| LSD (P = .05) |  |  |  |  | 100.9 | 104.1 | 0.4433 | 0.185 |
| Standard Deviation |  |  |  |  | 73.2 | 75.5 | 0.3217 | 0.134 |
| CV |  |  |  |  | 6.0 | 15.0 | 17.67 | 7.77 |

TABLE 13b

Effect of treatments on alkaloid parameters.

| Trt No. | Treatment Name | Rate | Rate Unit | STRAW MORPHINE % | MORPHINE kg/ha | THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
|  | NIL |  |  | 0.66 | 9.21 | 1.094 | 15.222 | 0.159 | 2.217 | 0.087 | 1.211 |
| 1 | COMP 1 | 1 | L/HA | 0.09 a | 1.17 a | 1.673 a | 20.901 ab | 0.245 a | 3.057 a | 0.024 ab | 0.292 a |
| 2 | COMP 1 | .25 | L/HA | 0.07 b | 0.85 b | 1.698 a | 20.069 b | 0.210 b | 2.509 b | 0.024 ab | 0.268 a |
| 2 | COMP 1 | .25 | L/HA |  |  |  |  |  |  |  |  |
| 2 | COMP 1 | .25 | L/HA |  |  |  |  |  |  |  |  |
| 2 | COMP 1 | .25 | L/HA |  |  |  |  |  |  |  |  |
| 3 | COMP 1 | .5 | L/HA | 0.05 e | 0.57 d | 1.824 a | 22.729 a | 0.170 c | 2.100 c | 0.022 ab | 0.270 a |
| 3 | COMP 1 | .5 | L/HA |  |  |  |  |  |  |  |  |
| 3 | COMP 1 | .5 | L/HA |  |  |  |  |  |  |  |  |
| 3 | COMP 1 | .5 | L/HA |  |  |  |  |  |  |  |  |
| 4 | COMP 1 | .5 | L/HA | 0.06 c | 0.74 bc | 1.693 a | 20.260 ab | 0.201 b | 2.402 bc | 0.019 b | 0.224 a |
| 4 | COMP 1 | .5 | L/HA |  |  |  |  |  |  |  |  |
| 4 | COMP 1 | .25 | L/HA |  |  |  |  |  |  |  |  |
| 4 | COMP 1 | .25 | L/HA |  |  |  |  |  |  |  |  |
| 5 | COMP 1 | .25 | L/HA | 0.05 d | 0.66 cd | 1.763 a | 21.687 ab | 0.174 c | 2.150 bc | 0.025 a | 0.303 a |
| 5 | COMP 1 | .25 | L/HA |  |  |  |  |  |  |  |  |
| 5 | COMP 1 | .5 | L/HA |  |  |  |  |  |  |  |  |
| 5 | COMP 1 | .5 | L/HA |  |  |  |  |  |  |  |  |
| LSD (P = .05) |  |  |  | 0.007 | 0.124 | 0.1415 | 2.4183 | 0.0203 | 0.3521 | 0.0056 | 0.0728 |
| Standard Deviation |  |  |  | 0.005 | 0.090 | 0.1026 | 1.7548 | 0.0148 | 0.2555 | 0.0040 | 0.0528 |
| CV |  |  |  | 7.47 | 11.3 | 5.93 | 8.31 | 7.39 | 10.46 | 17.85 | 19.45 |

Example 14

Introduction

Trial to compare the effect of 1 and 1.5 L/ha rates of Compound 1 applied in various configurations over three dates on Clopyralid (Lontrel™)-treated thebaine crop. Sprays were applied on 8, 15 and 19 December, with crop at early run-up, bud-emergence and hook stages, respectively. Capsules were harvested from plots and from crop adjacent to the trial (Nil) on 2 March.

TABLE 14a

Effect of treatments on yield parameters.

| Trt No. | Treatment Name | Rate | Rate Unit | Grow Stg | STRAW kg/ha | SEED kg/ha | CAPSULE/SEED RATIO | YIELD kg/ha |
|---|---|---|---|---|---|---|---|---|
|  | NIL |  |  |  | 1393 | 862 | 1.142 | 2.26 |
| 1 | COMPOUND 1 | .5 | L/HA | ERU | 1247 a | 424 a | 2.062 a | 1.67 a |
| 1 | COMPOUND 1 | .25 | L/HA | BUD-EM |  |  |  |  |
| 1 | COMPOUND 1 | .25 | L/HA | HOOK |  |  |  |  |
| 2 | COMPOUND 1 | .25 | L/HA | ERU | 1238 a | 477 a | 1.871 a | 1.72 a |
| 2 | COMPOUND 1 | .25 | L/HA | BUD-EM |  |  |  |  |
| 2 | COMPOUND 1 | .5 | L/HA | HOOK |  |  |  |  |
| 3 | COMPOUND 1 | .25 | L/HA | ERU | 1315 a | 501 a | 1.949 a | 1.82 a |
| 3 | COMPOUND 1 | .5 | L/HA | BUD-EM |  |  |  |  |
| 3 | COMPOUND 1 | .25 | L/HA | HOOK |  |  |  |  |
| 4 | COMPOUND 1 | 1 | L/HA | ERU | 1259 a | 459 a | 2.138 a | 1.72 a |
| 4 | COMPOUND 1 | .25 | L/HA | BUD-EM |  |  |  |  |
| 4 | COMPOUND 1 | .25 | L/HA | HOOK |  |  |  |  |
| 5 | COMPOUND 1 | .25 | L/HA | ERU | 1185 a | 487 a | 1.701 a | 1.67 a |
| 5 | COMPOUND 1 | .25 | L/HA | BUD-EM |  |  |  |  |
| 5 | COMPOUND 1 | 1 | L/HA | HOOK |  |  |  |  |
| LSD (P = .05) |  |  |  |  | 154.5 | 135.6 | 0.6501 | 0.256 |
| Standard Deviation |  |  |  |  | 112.1 | 98.4 | 0.4717 | 0.185 |
| CV |  |  |  |  | 8.98 | 20.95 | 24.27 | 10.78 |

TABLE 14b

Effect of treatments on alkaloid parameters.

| Trt No. | Treatment Name | Rate | Rate Unit | STRAW MORPHINE % | MORPHINE kg/ha | THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
|  | NIL |  |  | 0.66 | 9.21 | 1.094 | 15.222 | 0.159 | 2.217 | 0.087 | 1.211 |
| 1 | COMP 1 | .5 | L/HA | 0.09 a | 1.10 a | 1.796 ab | 22.417 a | 0.245 a | 3.065 a | 0.025 a | 0.311 a |
| 1 | COMP 1 | .25 | L/HA |  |  |  |  |  |  |  |  |
| 1 | COMP 1 | .25 | L/HA |  |  |  |  |  |  |  |  |
| 2 | COMP 1 | .25 | L/HA | 0.08 ab | 1.00 ab | 1.810 ab | 22.393 a | 0.238 ab | 2.922 a | 0.022 a | 0.278 a |
| 2 | COMP 1 | .25 | L/HA |  |  |  |  |  |  |  |  |
| 2 | COMP 1 | .5 | L/HA |  |  |  |  |  |  |  |  |
| 3 | COMP 1 | .25 | L/HA | 0.08 ab | 1.05 ab | 1.736 b | 22.815 a | 0.219 bc | 2.880 a | 0.022 a | 0.292 a |
| 3 | COMP 1 | .5 | L/HA |  |  |  |  |  |  |  |  |
| 3 | COMP 1 | .25 | L/HA |  |  |  |  |  |  |  |  |
| 4 | COMP 1 | 1 | L/HA | 0.07 bc | 0.90 ab | 1.767 b | 22.190 a | 0.218 bc | 2.729 ab | 0.019 a | 0.235 a |
| 4 | COMP 1 | .25 | L/HA |  |  |  |  |  |  |  |  |
| 4 | COMP 1 | .25 | L/HA |  |  |  |  |  |  |  |  |
| 5 | COMP 1 | .25 | L/HA | 0.07 c | 0.83 b | 1.849 a | 21.876 a | 0.205 c | 2.430 b | 0.019 a | 0.221 a |
| 5 | COMP 1 | .25 | L/HA |  |  |  |  |  |  |  |  |
| 5 | COMP 1 | 1 | L/HA |  |  |  |  |  |  |  |  |
| LSD (P = .05) |  |  |  | 0.009 | 0.216 | 0.0759 | 2.4874 | 0.0223 | 0.3491 | 0.0062 | 0.0937 |
| Standard Deviation |  |  |  | 0.006 | 0.157 | 0.0551 | 1.8049 | 0.0162 | 0.2533 | 0.0045 | 0.0680 |
| CV |  |  |  | 8.11 | 16.1 | 3.08 | 8.08 | 7.19 | 9.03 | 20.92 | 25.42 |

Example 15

Introduction

Trial to evaluate the performance of Compound 1 when tank-mixed with protectant fungicides for control of downy mildew. Treatment sprays were applied on 24 November and 1 December, with crop at early run-up and bud-emergence, respectively. Capsules were harvested from plots and from crop adjacent to the trial (Nil) on 17 February.

Penncozeb 750DF™, Activator™ and Penncozeb 420SC™ are all manufactured by Nufarm. Activator contains 850 g/L alkyl polyoxethylene ether and free fatty acids and 50 g/L isopropanol. Bion™ (acibenzolar-s-methyl) is manufactured by Syngenta and is a plant activator. Fungi-Fos™ (manufactured by Rutec) and Agri-FoS™ (manufactured by Agrichem) both contain the active ingredient "phosphoric acid".

TABLE 15a

Effect of treatments on yield parameters.

| Trt No. | Treatment Name | Rate | Rate Unit | Grow Stg | STRAW kg/ha | SEED kg/ha | CAPSULE/ SEED RATIO | YIELD kg/ha |
|---|---|---|---|---|---|---|---|---|
|  | NIL |  |  |  | 1505 | 1140 | 0.937 | 2.65 |
| 1 | COMPOUND 1 | .5 | L/HA | ERU | 1609 a | 927 a | 1.211 b | 2.53 ab |
| 1 | COMPOUND 1 | .5 | L/HA | BE |  |  |  |  |
| 2 | COMPOUND 1 | .5 | L/HA | ERU | 1731 a | 961 a | 1.271 b | 2.69 a |
| 2 | FUNGI-FOS | 3 | L/HA | ERU |  |  |  |  |
| 2 | PENNCOZEB | 2.5 | KG/HA | ERU |  |  |  |  |
| 2 | COMPOUND 1 | .33 | L/HA | BE |  |  |  |  |
| 2 | FUNGI-FOS | 3 | L/HA | BE |  |  |  |  |
| 2 | PENNCOZEB | 2.5 | KG/HA | BE |  |  |  |  |
| 3 | COMPOUND 1 | .5 | L/HA | ERU | 1609 a | 898 ab | 1.262 b | 2.51 ab |
| 3 | FUNGI-FOS | 3 | L/HA | ERU |  |  |  |  |
| 3 | ACTIVATOR | .125 | % V/V | ERU |  |  |  |  |
| 3 | COMPOUND 1 | .5 | L/HA | ERU |  |  |  |  |
| 3 | FUNGI-FOS | 3 | L/HA | BE |  |  |  |  |
| 3 | PENNCOZEB | 2.5 | KG/HA | BE |  |  |  |  |
| 3 | ACTIVATOR | .125 | % V/V | BE |  |  |  |  |
| 4 | COMPOUND 1 | .5 | L/HA | ERU | 1595 a | 736 c | 1.517 a | 2.33 b |
| 4 | FUNGI-FOS | 3 | L/HA | ERU |  |  |  |  |
| 4 | PENHCOZEB | 2.5 | KG/HA | ERU |  |  |  |  |
| 4 | BION | .08 | KG/HA | ERU |  |  |  |  |
| 4 | COMPOUND 1 | .5 | L/HA | BE |  |  |  |  |
| 4 | FUNGI-FOS | 3 | L/HA | BE |  |  |  |  |
| 4 | PENNCOZEB | 2.5 | KG/HA | BE |  |  |  |  |
| 4 | BION | .08 | KG/HA | BE |  |  |  |  |
| 5 | COMPOUND 1 | .5 | L/HA | ERU | 1635 a | 802 bc | 1.425 a | 2.44 b |
| 5 | FUNGI-FOS | 3 | L/HA | ERU |  |  |  |  |
| 5 | PENNCOZEB | 2.5 | KG/HA | ERU |  |  |  |  |
| 5 | BION | .08 | KG/HA | ERU |  |  |  |  |
| 5 | ACTIVATOR | .125 | % V/V | ERU |  |  |  |  |
| 5 | COMPOUND 1 | .5 | L/HA | BE |  |  |  |  |
| 5 | FUNGI-FOS | 3 | L/HA | BE |  |  |  |  |
| 5 | PENNCOZEB | 2.5 | KG/HA | BE |  |  |  |  |
| 5 | BION | .08 | KG/HA | BE |  |  |  |  |
| 5 | ACTIVATOR | .125 | % V/V | BE |  |  |  |  |
| LSD (P = .05) |  |  |  |  | 143.9 | 111.3 | 0.1370 | 0.234 |
| Standard Deviation |  |  |  |  | 104.4 | 80.7 | 0.0994 | 0.170 |
| CV |  |  |  |  | 6.39 | 9.34 | 7.43 | 6.8 |

TABLE 15b

Effect of treatments on alkaloid parameters.

| Trt No. | Treatment Name | Rate | Rate Unit | STRAW MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
|  | NIL |  |  | 0.74 | 11.12 | 0.995 | 15.070 | 0.181 | 2.767 | 0.100 | 1.478 |
| 1 | COMPOUND 1 | .5 | L/HA | 0.18 a | 2.83 a | 1.673 a | 26.982 a | 0.312 a | 5.044 a | 0.030 b | 0.487 b |
| 1 | COMPOUND 1 | .5 | L/HA |  |  |  |  |  |  |  |  |
| 2 | COMPOUND 1 | .5 | L/HA | 0.18 a | 3.09 a | 1.633 a | 28.249 a | 0.293 ab | 5.079 a | 0.034 ab | 0.580 ab |
| 2 | FUNGI-FOS | 3 | L/HA |  |  |  |  |  |  |  |  |
| 2 | PENNCOZEB | 2.5 | KG/HA |  |  |  |  |  |  |  |  |
| 2 | COMPOUND 1 | .5 | L/HA |  |  |  |  |  |  |  |  |
| 2 | FUNGI-FOS | 3 | L/HA |  |  |  |  |  |  |  |  |
| 2 | PENNCOZEB | 2.5 | KG/HA |  |  |  |  |  |  |  |  |
| 3 | COMPOUND 1 | .5 | L/HA | 0.18 a | 2.93 a | 1.630 a | 26.133 a | 0.275 bc | 4.444 b | 0.034 ab | 0.532 ab |
| 3 | FUNGI-FOS | 3 | L/HA |  |  |  |  |  |  |  |  |
| 3 | PENNCOZEB | 2.5 | KG/HA |  |  |  |  |  |  |  |  |
| 3 | ACTIVATOR | .125 | % V/V |  |  |  |  |  |  |  |  |
| 3 | COMPOUND 1 | .5 | L/HA |  |  |  |  |  |  |  |  |
| 3 | FUNGI-FOS | 3 | L/HA |  |  |  |  |  |  |  |  |
| 3 | PENNCOZEB | 2.5 | KG/HA |  |  |  |  |  |  |  |  |
| 3 | ACTIVATOR | .125 | % V/V |  |  |  |  |  |  |  |  |
| 4 | COMPOUND 1 | .5 | L/HA | 0.18 a | 2.83 a | 1.678 a | 26.739 a | 0.267 c | 4.111 b | 0.042 a | 0.655 a |
| 4 | FUNGI-FOS | 3 | L/HA |  |  |  |  |  |  |  |  |
| 4 | PENNCOZEB | 2.5 | KG/HA |  |  |  |  |  |  |  |  |
| 4 | BION | .08 | KG/HA |  |  |  |  |  |  |  |  |
| 4 | COMPOUND 1 | .5 | L/HA |  |  |  |  |  |  |  |  |
| 4 | FUNGI-FOS | 3 | L/HA |  |  |  |  |  |  |  |  |

TABLE 15b-continued

Effect of treatments on alkaloid parameters.

| Trt No. | Treatment Name | Rate | Rate Unit | STRAW MORPHINE % | MOR- PHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
| 4 | PENNCOZEB | 2.5 | KG/HA | | | | | | | | |
| 4 | BION | .08 | KG/HA | | | | | | | | |
| 5 | COMPOUND 1 | .5 | L/HA | 0.18 a | 2.98 a | 1.686 a | 27.621 a | 0.268 c | 4.402 b | 0.041 a | 0.668 a |
| 5 | FUNGI-FOS | 3 | L/HA | | | | | | | | |
| 5 | PENNCOZEB | 2.5 | KG/HA | | | | | | | | |
| 5 | BION | .08 | KG/HA | | | | | | | | |
| 5 | ACTIVATOR | .125 | % V/V | | | | | | | | |
| 5 | COMPOUND 1 | .5 | L/HA | | | | | | | | |
| 5 | FUNGI-FOS | 3 | L/HA | | | | | | | | |
| 5 | PENNCOZEB | 2.5 | KG/HA | | | | | | | | |
| 5 | BION | .08 | KG/HA | | | | | | | | |
| 5 | ACTIVATOR | .125 | % V/V | | | | | | | | |
| LSD (P = .05) | | | | 0.030 | 0.532 | 0.0868 | 2.6001 | 0.0211 | 0.5701 | 0.0075 | 0.1289 |
| Standard Deviation | | | | 0.022 | 0.386 | 0.0630 | 1.8867 | 0.0152 | 0.4095 | 0.0054 | 0.0935 |
| CV | | | | 12.17 | 13.19 | 3.8 | 6.95 | 5.36 | 8.87 | 15.03 | 16.0 |

Example 16

Introduction

Trial to evaluate the performance of Compound 1 when tank-mixed with protectant fungicides for control of downy mildew. Treatment sprays were applied on 24 November and 1 December, with crop at early run-up and bud-emergence, respectively. Capsules were harvested from plots and from crop adjacent to the trial (Nil) on 17 February.

TABLE 16a

Effect of treatments on yield parameters.

| Trt No. | Treatment Name | Rate | Rate Unit | Grow Stg | STRAW kg/ha | SEED kg/ha | CAPSULE/ SEED RATIO | YIELD kg/ha |
|---|---|---|---|---|---|---|---|---|
| | NIL | | | | 1505 | 1140 | 0.937 | 2.65 |
| 1 | COMPOUND 1 | .5 | L/HA | ERU | 1800 a | 851 a | 1.477 a | 2.65 a |
| 1 | COMPOUND 1 | .5 | L/HA | BE | | | | |
| 2 | COMPOUND 1 | .5 | L/HA | ERU | 1789 a | 798 a | 1.574 a | 2.59 a |
| 2 | ACTIVATOR | .125 | % V/V | ERU | | | | |
| 2 | COMPOUND 1 | .33 | L/HA | BE | | | | |
| 2 | ACTIVATOR | .125 | % V/V | BE | | | | |
| 3 | COMPOUND 1 | .5 | L/HA | ERU | 1744 a | 807 a | 1.521 a | 2.55 a |
| 3 | PENNCOZEB | 3.5 | L/HA | ERU | | | | |
| 3 | COMPOUND 1 | .5 | L/HA | BE | | | | |
| 3 | PENNCOZEB | 3.5 | L/HA | BE | | | | |
| 4 | COMPOUND 1 | .5 | L/HA | ERU | 1872 a | 853 a | 1.538 a | 2.73 a |
| 4 | PENNCOZEB | 2.5 | KG/HA | ERU | | | | |
| 4 | COMPOUND 1 | .5 | L/HA | BE | | | | |
| 4 | PENNCOZEB | 2.5 | KG/HA | BE | | | | |
| 5 | COMPOUND 1 | .5 | L/HA | ERU | 1833 a | 825 a | 1.568 a | 2.66 a |
| 5 | PENNCOZEB | 2.5 | KG/HA | ERU | | | | |
| 5 | ACTIVATOR | .125 | % V/V | ERU | | | | |
| 5 | COMPOUND 1 | .5 | L/HA | BE | | | | |
| 5 | PENNCOZEB | 2.5 | KG/HA | BE | | | | |
| 5 | ACTIVATOR | .125 | % V/V | BE | | | | |
| LSD (P = .05) | | | | | 143.8 | 117.4 | 0.2573 | 0.193 |
| Standard Deviation | | | | | 104.3 | 85.2 | 0.1867 | 0.140 |
| CV | | | | | 5.77 | 10.3 | 12.16 | 5.32 |

TABLE 16b

Effect of treatments on alkaloid parameters.

| Trt No. | Treatment Name | Rate | Rate Unit | STRAW MORPHINE % | MOR-PHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
| 1 | COMPOUND 1 | .5 | L/HA | 0.18 b | 3.24 b | 1.571 b | 28.323 a | 0.315 b | 5.681 b | 0.026 b | 0.457 b |
| 1 | COMPOUND 1 | .5 | L/HA | | | | | | | | |
| 2 | COMPOUND 1 | .5 | L/HA | 0.18 b | 3.22 b | 1.661 a | 29.707 a | 0.323 ab | 5.780 ab | 0.026 b | 0.456 b |
| 2 | ACTIVATOR | .125 | % V/V | | | | | | | | |
| 2 | COMPOUND 1 | .5 | L/HA | | | | | | | | |
| 2 | ACTIVATOR | .125 | % V/V | | | | | | | | |
| 3 | COMPOUND 1 | .5 | L/HA | 0.18 b | 3.15 b | 1.604 ab | 28.058 a | 0.305 b | 5.358 b | 0.026 b | 0.444 b |
| 3 | PENNCOZEB | 3.5 | L/HA | | | | | | | | |
| 3 | COMPOUND 1 | .5 | L/HA | | | | | | | | |
| 3 | PENNCOZEB | 3.5 | L/HA | | | | | | | | |
| 4 | COMPOUND 1 | .5 | L/HA | 0.20 a | 3.97 a | 1.544 b | 28.846 a | 0.340 a | 6.360 a | 0.027 b | 0.502 ab |
| 4 | PENNCOZEB | 2.5 | KG/HA | | | | | | | | |
| 4 | COMPOUND 1 | .5 | L/HA | | | | | | | | |
| 4 | PENNCOZEB | 2.5 | KG/HA | | | | | | | | |
| 5 | COMPOUND 1 | .5 | L/HA | 0.19 ab | 3.45 ab | 1.589 ab | 29.097 a | 0.317 ab | 5.809 ab | 0.030 a | 0.553 a |
| 5 | PENNCOZEB | 2.5 | KG/HA | | | | | | | | |
| 5 | ACTIVATOR | .125 | % V/V | | | | | | | | |
| 5 | COMPOUN | .5 | L/HA | | | | | | | | |
| 5 | PENNCOZEB | 2.5 | KG/HA | | | | | | | | |
| 5 | ACTIVATOR | .125 | % V/V | | | | | | | | |
| LSD (P = .05) | | | | 0.020 | 0.577 | 0.0803 | 2.3694 | 0.0236 | 0.5640 | 0.0030 | 0.0719 |
| Standard | | | | 0.015 | 0.415 | 0.0583 | 1.7193 | 0.0171 | 0.4093 | 0.0022 | 0.0522 |
| CV | | | | 7.87 | 12.17 | 3.66 | 5.97 | 5.36 | 7.06 | 8.06 | 10.82 |

Example 17

Introduction

Trial to evaluate the performance of Compound 1 when tank-mixed with curative fungicides for control of downy mildew. Treatment sprays were applied on 28 November (late run-up), with Ridomil applied separately on 1 December (bud-emergence). Capsules were harvested from plots and from crop adjacent to the trial (Nil) on 17 February.

TABLE 17a

Effect of treatments on yield parameters.

| Trt No. | Treatment Name | Rate | Rate Unit | Grow Stg | STRAW kg/ha | SEED kg/ha | CAPSULE/ SEED RATIO | YIELD kg/ha |
|---|---|---|---|---|---|---|---|---|
| | NIL | | | | 1505 | 1140 | 0.937 | 2.65 |
| 1 | COMPOUND 1 | 1 | L/HA | LRU | 1691 a | 753 a | 1.624 a | 2.44 a |
| 1 | RIDOMIL MZ 720 | 2.5 | KG/HA | BE | | | | |
| 1 | ACTIVATOR | .125 | % V/V | BE | | | | |
| 2 | COMPOUND 1 | 1 | L/HA | BE | 1693 a | 667 a | 6.094 a | 2.36 a |
| 2 | RIDOMIL MZ 720 | 2.5 | KG/HA | BE | | | | |
| 2 | ACTIVATOR | .125 | % V/V | BE | | | | |
| 3 | COMPOUND 1 | 1 | L/HA | BE | 1687 a | 763 a | 6.648 a | 2.45 a |
| 3 | RIDOMIL MZ 720 | 2.5 | KG/HA | BE | | | | |
| 4 | COMPOUND 1 | 1 | L/HA | BE | 1747 a | 803 a | 1.908 a | 2.55 a |
| 4 | ACROBAT | 2 | KG/HA | BE | | | | |
| 5 | COMPOUND 1 | 1 | L/HA | BE | 1755 a | 669 a | 7.607 a | 2.42 a |
| 5 | ACROBAT | 2 | KG/HA | BE | | | | |
| 5 | ACTIVATOR | .125 | % V/V | BE | | | | |
| LSD (P = .05) | | | | | 103.3 | 250.1 | 8.9757 | 0.299 |
| Standard Deviation | | | | | 74.9 | 181.5 | 6.5130 | 0.217 |
| CV | | | | | 4.37 | 24.83 | 136.37 | 8.88 |

TABLE 17b

Effect of treatments on alkaloid parameters.

| Trt No. | Treatment Name | Rate | Rating Unit Rate Unit | STRAW MORPHINE % | MOR- PHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
|  | NIL |  |  | 0.74 | 11.12 | 0.995 | 15.070 | 0.181 | 2.767 | 0.100 | 1.478 |
| 1 | COMPOUND 1 | 1 | L/HA | 0.17 a | 2.90 a | 1.592 a | 26.926 a | 0.265 a | 4.501 a | 0.027 a | 0.457 a |
| 1 | RIDOMIL MZ | 2.5 | KG/HA |  |  |  |  |  |  |  |  |
| 1 | ACTIVATOR | .125 | % V/V |  |  |  |  |  |  |  |  |
| 2 | COMPOUND 1 | 1 | L/HA | 0.16 a | 2.74 a | 1.643 a | 27.763 a | 0.267 a | 4.526 a | 0.029 a | 0.485 a |
| 2 | RIDOMIL MZ | 2.5 | KG/HA |  |  |  |  |  |  |  |  |
| 2 | ACTIVATOR | .125 | % V/V |  |  |  |  |  |  |  |  |
| 3 | COMPOUND 1 | 1 | L/HA | 0.18 a | 3.03 a | 1.609 a | 27.169 a | 0.276 a | 4.685 a | 0.025 a | 0.427 a |
| 3 | RIDOMIL MZ | 2.5 | KG/HA |  |  |  |  |  |  |  |  |
| 4 | COMPOUND 1 | 1 | L/HA | 0.17 a | 3.02 a | 1.601 a | 27.944 a | 0.283 a | 4.952 a | 0.026 a | 0.445 a |
| 4 | ACROBAT | 2 | KG/HA |  |  |  |  |  |  |  |  |
| 5 | COMPOUND 1 | 1 | L/HA | 0.16 a | 2.90 a | 1.572 a | 27.596 a | 0.261 a | 4.604 a | 0.024 a | 0.420 a |
| 5 | ACROBAT | 2 | KG/HA |  |  |  |  |  |  |  |  |
| 5 | ACTIVATOR | .125 | % V/V |  |  |  |  |  |  |  |  |
| LSD (P = .05) |  |  |  | 0.025 | 0.401 | 0.1261 | 2.9225 | 0.0253 | 0.5726 | 0.0048 | 0.0801 |
| Standard Deviation |  |  |  | 0.018 | 0.291 | 0.0915 | 2.1207 | 0.0183 | 0.4155 | 0.0035 | 0.0581 |
| CV |  |  |  | 10.52 | 9.97 | 5.71 | 7.72 | 6.78 | 8.93 | 13.33 | 13.01 |

Example 18

Introduction

Trial to evaluate various rates of Compound 2 applied at different growth stages in Lontrel-treated or otherwise untreated morphine crop. Treatment sprays were applied on 7, 22 and 29 November, 2 and 9 December, with crop at 10-12 leaf, run-up, bud-emergence, hook and early flowering stages, respectively. Clopyralid (Lontrel™) was applied at 1 L/ha, across half of all plots, on 7 November. Capsules were harvested from 2 m×2 m quadrats placed in Lontrel-treated and otherwise untreated halves of all plots on 6 February. Data were analysed separately for Lontrel-treated and non-Lontrel crop. Results for plots sprayed at each sowing date were used as replicates to calculate means for different rates of Compound 2.

TABLE 18a

Effect of treatments on yield parameters of otherwise untreated crop. Treatment means are of data for five single plots each sprayed with the appropriate rate at different growth stages.

| Trt No. | Treatment Name | Rate | Rate Unit | STRAW kg/ha | SEED kg/ha | CAPSULE/ SEED RATIO | YIELD t/ha |
|---|---|---|---|---|---|---|---|
| 1 | NIL |  |  | 1108 ab | 1235 ab | 0.621 b | 2.34 a |
| 2 | COMPOUND 2 | .05 | L/HA | 1086 ab | 1275 a | 0.590 b | 2.36 a |
| 3 | COMPOUND 2 | .1 | L/HA | 1014 b | 1097 c | 0.641 b | 2.11 b |
| 4 | COMPOUND 2 | .5 | L/HA | 1098 ab | 1081 c | 0.717 a | 2.18 ab |
| 5 | COMPOUND 2 | 1 | L/HA | 1208 a | 1133 bc | 0.742 a | 2.34 a |
| LSD (P = Various) |  |  |  | 115.1 | 102.3 | 0.0613 | 0.196 |
| Std Deviation |  |  |  | 83.5 | 74.3 | 0.0445 | 0.142 |
| CV |  |  |  | 7.57 | 6.38 | 6.71 | 6.29 |

TABLE 18b

Effect of treatments on alkaloid parameters of otherwise untreated crop.
Treatment means are of data for five single plots each sprayed with the
appropriate rate at different growth stages.

| Trt No | Treatment Name | Rate | Rate Unit | STRAW MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
| 1 | NIL | | | 2.04 a | 22.53 a | 0.094 b | 1.07 b | 0.023 c | 0.26 b | 0.043 a | 0.47 a |
| 2 | COMPOUND 2 | .05 | L/HA | 1.94 a | 21.06 ab | 0.144 b | 1.58 b | 0.039 c | 0.43 b | 0.047 a | 0.51 a |
| 3 | COMPOUND 2 | .1 | L/HA | 1.70 a | 17.00 b | 0.404 b | 4.26 b | 0.133 b | 1.40 b | 0.053 a | 0.53 a |
| 4 | COMPOUND 2 | .5 | L/HA | 0.93 b | 10.24 c | 1.094 a | 11.89 a | 0.289 a | 3.19 a | 0.042 a | 0.46 a |
| 5 | COMPOUND 2 | 1 | L/HA | 0.84 b | 10.00 c | 1.227 a | 15.04 a | 0.297 a | 3.64 a | 0.041 a | 0.49 a |
| LSD (P = .05) | | | | 0.335 | 4.114 | 0.3331 | 4.160 | 0.0910 | 1.209 | 0.0198 | 0.205 |
| Std Deviation | | | | 0.243 | 2.985 | 0.2417 | 3.019 | 0.0660 | 0.877 | 0.0144 | 0.149 |
| CV | | | | 16.29 | 18.47 | 40.79 | 44.61 | 42.27 | 49.2 | 31.78 | 30.11 |

TABLE 18c

Effect of treatments on yield parameters of Lontrel-treated crop.
Treatment means are of data for five single plots each sprayed
with the appropriate rate at different growth stages.

| Trt No | Treatment Name | Rate | Rate Unit | STRAW kg/ha | SEED kg/ha | CAPSULE/SEED RATIO | YIELD t/ha |
|---|---|---|---|---|---|---|---|
| 1 | NIL | | | 1778 a | 123 a | 10.606 b | 1.90 a |
| 2 | COMPOUND 2 | .05 | L/HA | 1858 a | 95 a | 17.329 a | 1.95 a |
| 3 | COMPOUND 2 | .1 | L/HA | 1821 a | 131 a | 13.334 ab | 1.95 a |
| 4 | COMPOUND 2 | .5 | L/HA | 1735 a | 90 a | 17.513 a | 1.83 a |
| 5 | COMPOUND 2 | 1 | L/HA | 1794 a | 79 a | 16.375 ab | 1.87 a |
| LSD (P = .05) | | | | 5.7327 | 167.9 | 66.1 | 0.179 |
| Standard Deviation | | | | 4.1598 | 121.8 | 47.9 | 0.130 |
| CV | | | | 27.67 | 6.78 | 46.39 | 6.85 |

TABLE 18d

Effect of treatments on alkaloid parameters of Lontrel-treated crop.
Treatment means are of data for five single plots each sprayed with
the appropriate rate at different growth stages.

| Trt No | Treatment Name | Rate | Rate Unit | STRAW MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
| 1 | NIL | | | 1.66 a | 29.71 a | 0.135 b | 2.39 b | 0.016 c | 0.29 b | 0.098 ab | 1.74 ab |
| 2 | COMPOUND 2 | .05 | L/HA | 1.65 a | 30.76 a | 0.192 b | 3.52 b | 0.027 bc | 0.49 b | 0.105 a | 1.95 a |
| 3 | COMPOUND 2 | .1 | L/HA | 1.47 a | 26.66 b | 0.442 b | 8.14 b | 0.092 b | 1.70 b | 0.107 a | 1.95 a |
| 4 | COMPOUND 2 | .5 | L/HA | 0.80 b | 14.14 c | 1.213 a | 20.69 a | 0.260 a | 4.46 a | 0.076 bc | 1.33 bc |
| 5 | COMPOUND 2 | 1 | L/HA | 0.67 b | 12.45 c | 1.415 a | 24.84 a | 0.247 a | 4.40 a | 0.067 c | 1.23 c |
| LSD (P = .05) | | | | 0.187 | 2.586 | 0.3127 | 6.159 | 0.0230 | 0.416 | 0.0692 | 1.451 |
| Std Deviation | | | | 0.135 | 1.876 | 0.2269 | 4.469 | 0.0167 | 0.302 | 0.0502 | 1.053 |
| CV | | | | 10.84 | 8.25 | 33.4 | 37.5 | 18.39 | 18.38 | 39.09 | 46.44 |

Example 19

Introduction

Trial to evaluate various rates of Compound 2 applied at different growth stages in Lontrel-treated or otherwise untreated thebaine crop. Treatment sprays were applied on 7, 22 and 29 November, 2 and 9 December, with crop at 10-12 leaf, run-up, bud-emergence, hook and early flowering stages, respectively. Clopyralid (Lontrel™) was applied at 1 L/ha, across half of all plots, on 7 November. Capsules were harvested from 2 m×2 m quadrats placed in Lontrel-treated and otherwise untreated halves of all plots on 12 February. Data were analysed separately for Lontrel-treated and non-Lontrel crop. Results for plots sprayed at each sowing date were used as replicates to calculate means for different rates of Compound 2.

TABLE 19a

Effect of treatments on yield parameters of otherwise untreated crop.
Treatment means are of data for five single plots each sprayed with
the appropriate rate at different growth stages.

| Trt No | Treatment Name | Rate | Rate Unit | STRAW kg/ha | SEED kg/ha | CAPSULE/ SEED RATIO | YIELD t/ha |
|---|---|---|---|---|---|---|---|
| 1 | NIL | | | 963 a | 1105 a | 0.603 c | 2.07 a |
| 2 | COMPOUND 2 | 05 | L/HA | 984 a | 1142 a | 0.596 c | 2.13 a |
| 3 | COMPOUND 2 | 1 | L/HA | 1058 a | 1159 a | 0.633 bc | 2.22 a |
| 4 | COMPOUND 2 | .5 | L/HA | 1012 a | 1019 a | 0.691 a | 2.03 a |
| 5 | COMPOUND 2 | 1 | L/HA | 1061 a | 1090 a | 0.676 ab | 2.15 a |
| LSD (P = .05) | | | | 120.6 | 134.9 | 0.0483 | 0.246 |
| Standard Deviation | | | | 87.5 | 97.9 | 0.0351 | 0.178 |
| CV | | | | 8.62 | 8.88 | 5.48 | 8.42 |

TABLE 19b

Effect of treatments on alkaloid parameters of otherwise untreated crop.
Treatment means are of data for five single plots each sprayed with the appropriate
rate at different growth stages.

| Trt No | Treatment Name | Rate | Rate Unit | STRAW MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
| 1 | NIL | | | 0.64 a | 6.14 a | 0.523 c | 5.02 d | 0.196 c | 1.87 c | 0.045 a | 0.43 a |
| 2 | COMPOUND 2 | .05 | L/HA | 0.56 a | 5.57 ab | 0.582 c | 5.69 d | 0.237 bc | 2.31 bc | 0.035 b | 0.34 ab |
| 3 | COMPOUND 2 | .1 | L/HA | 0.43 b | 4.54 b | 0.704 b | 7.37 c | 0.302 ab | 3.15 a | 0.024 c | 0.26 bc |
| 4 | COMPOUND 2 | .5 | L/HA | 0.28 c | 2.93 c | 0.932 a | 9.35 b | 0.320 a | 3.17 a | 0.017 cd | 0.17 cd |
| 5 | COMPOUND 2 | 1 | L/HA | 0.20 c | 2.14 c | 0.979 a | 10.29 a | 0.274 ab | 2.93 ab | 0.011 d | 0.12 d |
| LSD (P = .05) | | | | 0.092 | 1.500 | 0.0790 | 0.872 | 0.0708 | 0.644 | 0.0090 | 0.125 |
| Std Dev | | | | 0.067 | 1.088 | 0.0574 | 0.633 | 0.0514 | 0.467 | 0.0065 | 0.091 |
| CV | | | | 15.73 | 25.53 | 7.71 | 8.39 | 19.34 | 17.4 | 24.97 | 34.5 |

TABLE 19c

Effect of treatments on yield parameters of Lontrel-treated crop.
Treatment means are of data for five single plots each sprayed with the appropriate
rate at different growth stages.

| Trt No | Treatment Name | Rate | Rate Unit | STRAW kg/ha | SEED kg/ha | CAPSULE/ SEED RATIO | YIELD t/ha |
|---|---|---|---|---|---|---|---|
| 1 | NIL | | | 1454 a | 48 a | 23.954 a | 1.50 a |
| 2 | COMPOUND 2 | .05 | L/HA | 1415 a | 112 a | 21.217 a | 1.53 a |
| 3 | COMPOUND 2 | .1 | L/HA | 1342 a | 60 a | 16.232 a | 1.40 a |
| 4 | COMPOUND 2 | .5 | L/HA | 1352 a | 82 a | 23.942 a | 1.43 a |
| 5 | COMPOUND 2 | 1 | L/HA | 1375 a | 41 a | 26.523 a | 1.41 a |
| LSD (P = .05) | | | | 134.1 | 85.3 | 14.0862 | 0.169 |
| Std Deviation | | | | 97.3 | 61.9 | 10.2213 | 0.123 |
| CV | | | | 7.01 | 90.29 | 45.68 | 8.43 |

TABLE 19d

Effect of treatments on alkaloid parameters of Lontrel-treated crop.
Treatment means are of data for five single plots each sprayed with the appropriate
rate at different growth stages.

| Trt No | Treatment Name | Rate | Rate Unit | STRAW MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
| 1 | NIL | | | 0.67 a | 9.73 a | 0.736 d | 10.75 c | 0.199 b | 2.92 b | 0.096 a | 1.39 a |
| 2 | COMPOUND 2 | .05 | L/HA | 0.66 a | 9.28 a | 0.769 d | 10.82 c | 0.225 b | 3.15 b | 0.083 a | 1.18 b |

TABLE 19d-continued

Effect of treatments on alkaloid parameters of Lontrel-treated crop.
Treatment means are of data for five single plots each sprayed with the appropriate
rate at different growth stages.

| Trt No | Treatment Name | Rate | Rate Unit | STRAW MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
| 3 | COMPOUND 2 | .1 | L/HA | 0.47 b | 6.48 b | 0.983 c | 12.94 a | 0.317 a | 4.15 a | 0.057 b | 0.79 c |
| 4 | COMPOUND 2 | .5 | L/HA | 0.27 c | 3.71 c | 1.259 b | 16.89 b | 0.340 a | 4.57 a | 0.033 c | 0.45 d |
| 5 | COMPOUND 2 | 1 | L/HA | 0.22 c | 3.09 c | 1.435 a | 19.66 a | 0.313 a | 4.33 a | 0.027 c | 0.37 d |
| LSD (P = .05) | | | | 0.058 | 1.057 | 0.1263 | 2.503 | 0.0515 | 0.715 | 0.0136 | 0.175 |
| Std Deviation | | | | 0.042 | 0.767 | 0.0917 | 1.816 | 0.0374 | 0.519 | 0.0099 | 0.127 |
| CV | | | | 9.14 | 11.88 | 8.84 | 12.78 | 13.4 | 13.57 | 16.74 | 15.15 |

Example 20

Introduction

Trial to evaluate sequential sprays of 0.4 L/ha Compound 2 on morphine crop. Sprays were applied, to a single 3 m×40 m strip, on 7, 22 and 29 November, 2 and 9 December, with crop at 10-12 leaf, run-up, bud-emergence, hook and early flowering stages, respectively. Capsules were harvested (on 6 February) from three quadrats placed in the sprayed strip and data from these was compared with data from untreated plots (Nil) in adjacent crop.

TABLE 20a

Effect of treatment on yield parameters.

| Trt No | Treatment Name | Rate | Rate Unit | Growth Stage | STRAW kg/ha | SEED kg/ha | CAPSULE/ SEED RATIO | YIELD t/ha |
|---|---|---|---|---|---|---|---|---|
| 1 | NIL | | | | 1108 | 1235 | 0.621 | 2.34 |
| 2 | COMPOUND 2 | .4 | L/HA | 10-12LF | 983 | 893 | 0.762 | 1.88 |
| 2 | COMPOUND 2 | .4 | L/HA | RUN-UP | | | | |
| 2 | COMPOUND 2 | .4 | L/HA | BUD-EM | | | | |
| 2 | COMPOUND 2 | .4 | L/HA | HOOK | | | | |
| 2 | COMPOUND 2 | .4 | L/HA | EF | | | | |

TABLE 20b

Effect of treatment on alkaloid parameters.

| Trt No | Treatment Name | Rate | Rate Unit | STRAW MORPHINE % | MORPHINE kg/ha | STRAW THEBAINE % | THEBAINE kg/ha | STRAW O'PAVIN % | ORIPAVINE kg/ha | STRAW CODEINE % | CODEINE kg/ha |
|---|---|---|---|---|---|---|---|---|---|---|---|
| 1 | NIL | | | 2.04 | 22.53 | 0.094 | 1.07 | 0.023 | 0.26 | 0.043 | 0.47 |
| 2 | COMPOUND 2 | .4 | L/HA | 0.17 | 1.70 | 1.890 | 18.46 | 0.308 | 3.01 | 0.027 | 0.25 |
| 2 | COMPOUND 2 | .4 | L/HA | | | | | | | | |
| 2 | COMPOUND 2 | .4 | L/HA | | | | | | | | |
| 2 | COMPOUND 2 | .4 | L/HA | | | | | | | | |
| 2 | COMPOUND 2 | .4 | L/HA | | | | | | | | |

Example 21

Introduction

Trial to evaluate an application of Compound 5 at different water volumes (153 or 250 L/ha) in morphine crop. It was applied on 13 December to a morphine crop at hook stage. Capsules were harvested from trial plots on 3 February.

TABLE 21a

Effect of treatments on yield parameters.

| Trt No | Treatment Name | Rate | Rate Unit | Water Vol | Unit | Grow Stg | STRAW kg/ha | SEED kg/ha | CAPSULE/ SEED RATIO | YIELD t/ha |
|---|---|---|---|---|---|---|---|---|---|---|
| 1 | NIL | | | | | | 1418 a | 1720 a | 0.587 a | 3.14 a |
| 2 | COMPOUND 5 | 3 | KG/HA | 153 | L/HA | HOOK | 1338 a | 1586 a | 0.600 a | 2.92 a |
| 3 | COMPOUND 5 | 3 | KG/HA | 250 | L/HA | HOOK | 1468 a | 1748 a | 0.595 a | 3.22 a |
| LSD (P = .05) | | | | | | | 156.2 | 190.4 | 0.0203 | 0.346 |
| Standard Deviation | | | | | | | 68.9 | 84.0 | 0.0090 | 0.153 |
| CV | | | | | | | 4.89 | 4.99 | 1.51 | 4.93 |

TABLE 21b

Effect of treatments on alkaloid parameters.

| Trt No | Treatment Name | Rate | Water Vol | STRAW MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|
| 1 | NIL | | | 2.26 a | 32.34 a | 0.097 b | 1.294 b | 0.016 b | 0.209 b | 0.088 a | 1.204 a |
| 2 | COMP 5 | 3 KG | 153 L/HA | 1.23 c | 16.61 b | 1.010 a | 13.313 a | 0.225 a | 2.939 a | 0.115 a | 1.577 a |
| 3 | COMP 5 | 3 KG | 250 L/HA | 1.37 b | 20.33 b | 0.796 a | 11.513 a | 0.176 a | 2.551 a | 0.121 a | 1.795 a |
| LSD (P = .05) | | | | 0.109 | 6.057 | 0.2217 | 3.3058 | 0.0505 | 0.6875 | 0.0495 | 0.7807 |
| Standard Deviation | | | | 0.048 | 2.672 | 0.0978 | 1.4585 | 0.0223 | 0.3033 | 0.0218 | 0.3444 |
| CV | | | | 2.97 | 11.57 | 15.42 | 16.75 | 16.02 | 15.97 | 20.21 | 22.58 |

Example 22

Introduction

Trial to evaluate most appropriate application rate of Compound 5 in Lontrel-treated thebaine crop. Treatments were applied on 2 December, with crop at hook stage. Capsules were harvested from trial plots on 29 January.

TABLE 22a

Effect of treatments on yield parameters.

| | Rating Unit | | | | | CAPSULE/ | |
|---|---|---|---|---|---|---|---|
| Trt No | Treatment Name | Rate | Rate Unit | STRAW kg/ha | SEED kg/ha | SEED RATIO | YIELD t/ha |
| 1 | NIL | | | 1373 b | 35 a | 27.940 ab | 1.41 b |
| 2 | COMPOUND 5 | 1 | KG/HA | 1403 ab | 33 a | 30.143 ab | 1.44 ab |
| 3 | COMPOUND 5 | 2 | KG/HA | 1510 ab | 39 a | 28.277 ab | 1.55 ab |
| 4 | COMPOUND 5 | 3 | KG/HA | 1586 a | 38 a | 31.973 a | 1.62 a |
| 5 | COMPOUND 5 | 4 | KG/HA | 1473 ab | 89 a | 16.171 b | 1.56 ab |
| 6 | COMPOUND 5 | 5 | KG/HA | 1498 ab | 89 a | 23.547 ab | 1.58 ab |
| 7 | COMPOUND 5 | 6 | KG/HA | 1448 ab | 69 a | 20.230 ab | 1.52 ab |
| LSD (P = .05) | | | | 177.0 | 55.5 | 12.5222 | 0.182 |
| Standard Deviation | | | | 135.6 | 42.5 | 9.5927 | 0.140 |
| CV | | | | 9.22 | 75.95 | 37.66 | 9.15 |

TABLE 22b

Effect of treatments on alkaloid parameters.

| | Rating Unit | | | STRAW | | STRAW | | STRAW | | STRAW | |
|---|---|---|---|---|---|---|---|---|---|---|---|
| Trt No | Treatment Name | Rate | Rate Unit | MORPHINE % | MORPHINE kg/ha | THEBAINE % | THEBAINE kg/ha | O'PAVINE % | ORIPAVINE kg/ha | CODEINE % | CODEINE kg/ha |
| 1 | NIL | | | 0.79 a | 10.89 a | 0.714 e | 9.788 d | 0.177 c | 2.436 c | 0.092 a | 1.257 a |
| 2 | COMPOUND 5 | 1 | KG/HA | 0.66 b | 9.25 b | 0.947 d | 13.295 c | 0.287 b | 4.028 b | 0.094 a | 1.320 a |
| 3 | COMPOUND 5 | 2 | KG/HA | 0.53 c | 8.04 b | 1.068 c | 16.139 b | 0.328 a | 4.946 a | 0.078 b | 1.167 ab |
| 4 | COMPOUND 5 | 3 | KG/HA | 0.42 d | 6.64 c | 1.288 ab | 20.461 a | 0.337 a | 5.351 a | 0.064 c | 1.008 bc |
| 5 | COMPOUND 5 | 4 | KG/HA | 0.41 d | 6.11 c | 1.226 b | 18.174 ab | 0.339 a | 5.001 a | 0.053 c | 0.782 c |
| 6 | COMPOUND 5 | 5 | KG/HA | 0.41 d | 6.10 c | 1.306 ab | 19.608 a | 0.343 a | 5.144 a | 0.056 c | 0.831 c |

TABLE 22b-continued

Effect of treatments on alkaloid parameters.

| Rating Unit | | | | STRAW | STRAW | | STRAW | | STRAW | | |
| --- | --- | --- | --- | --- | --- | --- | --- | --- | --- | --- | --- |
| Trt Treatment No Name | Rate | Rate Unit | | MORPHINE % | MORPHINE kg/ha | THEBAINE % | THEBAINE kg/ha | O'PAVINE % | ORIPAVINE kg/ha | CODEINE % | CODEINE kg/ha |
| 7 COMPOUND 5 | 6 | KG/HA | | 0.37 d | 5.40 c | 1.366 a | 19.780 a | 0.342 a | 4.958 a | 0.054 c | 0.784 c |
| LSD (P = .05) | | | | 0.061 | 1.397 | 0.1081 | 2.7771 | 0.0171 | 0.6397 | 0.0134 | 0.2331 |
| Standard Deviation | | | | 0.047 | 1.070 | 0.0828 | 2.1274 | 0.0131 | 0.4901 | 0.0103 | 0.1785 |
| CV | | | | 9.07 | 14.29 | 7.32 | 12.7 | 4.27 | 10.77 | 14.7 | 17.49 |

Example 23

Introduction

Trial to evaluate most appropriate application time of Compound 5 in Lontrel-treated thebaine crop. Treatments were applied on 28 November, 2, 9 and 12 December, with crop at bud-emergence, hook, early-flower and full-flower stages. Capsules were harvested from trial plots on 11 February.

TABLE 23a

Effect of treatments on yield parameters.

| Rating Unit | | | | | | CAPSULE/ | |
| --- | --- | --- | --- | --- | --- | --- | --- |
| Trt Treatment No Name | Rate | Rate Unit | Grow Stg | STRAW kg/ha | SEED kg/ha | SEED RATIO | YIELD t/ha |
| 1 NIL | | | | 1380 b | 24 b | 45.332 a | 1.41 b |
| 2 COMPOUND 5 | 2.75 | KG/HA | BUD-EM | 1479 a | 42 a | 26.798 b | 1.52 a |
| 3 COMPOUND 5 | 2.75 | KG/HA | HOOK | 1235 c | 25 b | 38.948 ab | 1.26 c |
| 4 COMPOUND 5 | 2.75 | KG/HA | EF | 1224 c | 21 b | 42.748 a | 1.24 c |
| 5 COMPOUND 5 | 2.75 | KG/HA | FF | 1333 b | 25 b | 47.649 a | 1.36 b |
| LSD (P = .05) | | | | 95.5 | 11.6 | 13.3683 | 0.092 |
| Standard Deviation | | | | 69.3 | 8.4 | 9.7004 | 0.067 |
| CV | | | | 5.21 | 30.7 | 24.07 | 4.92 |

TABLE 23b

Effect of treatments on alkaloid parameters.

| Rating Unit | | | | STRAW | MOR- | STRAW | | STRAW | | STRAW | |
| --- | --- | --- | --- | --- | --- | --- | --- | --- | --- | --- | --- |
| Trt Treatment No Name | Rate | Rate Unit | Grow Stg | MORPHINE % | PHINE kg/ha | THEBAINE % | THEBAINE kg/ha | O'PAVINE % | ORIPAVINE kg/ha | CODEINE % | CODEINE kg/ha |
| 1 NIL | | | | 0.77 a | 10.59 a | 0.661 c | 9.10 d | 0.171 c | 2.35 c | 0.104 a | 1.44 a |
| 2 COMP 5 | 2.75 | KG/HA | BE | 0.43 c | 6.32 bc | 1.106 a | 16.36 a | 0.335 a | 4.96 a | 0.079 b | 1.17 b |
| 3 COMP 5 | 2.75 | KG/HA | HOOK | 0.50 b | 6.17 bc | 1.009 b | 12.47 c | 0.309 b | 3.82 b | 0.087 b | 1.08 b |
| 4 COMP 5 | 2.75 | KG/HA | EF | 0.45 bc | 5.46 c | 1.096 a | 13.39 bc | 0.297 b | 3.62 b | 0.058 c | 0.71 c |
| 5 COMP 5 | 2.75 | KG/HA | FF | 0.51 b | 6.82 b | 1.077 a | 14.36 b | 0.291 b | 3.87 b | 0.064 c | 0.86 c |
| LSD (P = .05) | | | | 0.063 | 1.207 | 0.0602 | 1.161 | 0.0229 | 0.362 | 0.0099 | 0.186 |
| Standard Deviation | | | | 0.046 | 0.876 | 0.0437 | 0.842 | 0.0166 | 0.263 | 0.0072 | 0.135 |
| CV | | | | 8.68 | 12.38 | 4.41 | 6.41 | 5.92 | 7.05 | 9.18 | 12.83 |

Example 24

Introduction

Trial to determine whether or not sequential applications of Compound 5 were more effective in increasing thebaine and oripavine than single applications. The trial was conducted in Lontrel-treated thebaine crop. Sprays were applied on 28 November, 2 and 9 December, with crop at bud-emergence, hook and early flowering stages, respectively. Capsules were harvested from trial plots on 11 February.

TABLE 24a

Effect of treatments on yield parameters.

| Trt No | Treatment Name | Rate | Rate Unit | Grow Stg | STRAW kg/ha | SEED kg/ha | CAPSULE/ SEED RATIO | YIELD t/ha |
|---|---|---|---|---|---|---|---|---|
| 1 | NIL | | | | 1421 a | 37 b | 30.324 a | 1.46 a |
| 2 | COMPOUND 5 | 2.75 | KG/HA | BUD-EM | 1439 a | 62 a | 21.763 a | 1.50 a |
| 3 | COMPOUND 5 | 2.75 | KG/HA | HOOK | 1241 b | 28 b | 36.393 a | 1.27 b |
| 4 | COMPOUND 5 | 1.375 | KG/HA | BUD-EM | 1397 a | 51 ab | 21.091 a | 1.45 a |
| 4 | COMPOUND 5 | 1.375 | KG/HA | HOOK | | | | |
| 5 | COMPOUND 5 | .92 | KG/HA | BUD-EM | 1377 a | 50 ab | 21.493 a | 1.43 a |
| 5 | COMPOUND 5 | .92 | KG/HA | HOOK | | | | |
| 5 | COMPOUND 5 | .92 | KG/HA | EF | | | | |
| LSD (P = .05) | | | | | 88.3 | 22.2 | 14.5531 | 0.094 |
| Standard Deviation | | | | | 64.1 | 16.1 | 10.5601 | 0.068 |
| CV | | | | | 4.66 | 35.5 | 40.29 | 4.81 |

TABLE 24b

Effect of treatments on alkaloid parameters.

| Trt No | Treatment Name | Rate | Rate Unit | Grow Stg | STRAW MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|---|
| 1 | NIL | | | | 0.78 a | 11.09 a | 0.633 c | 8.99 c | 0.165 d | 2.34 c | 0.100 a | 1.42 a |
| 2 | COMP 5 | 2.75 | KG/HA | BE | 0.45 b | 6.41 b | 1.100 b | 15.83 a | 0.363 b | 5.23 a | 0.077 b | 1.11 b |
| 3 | COMP 5 | 2.75 | KG/HA | HK | 0.39 b | 4.83 c | 1.153 a | 14.30 b | 0.335 c | 4.16 b | 0.063 c | 0.78 c |
| 4 | COMP 5 | 1.375 | KG/HA | BE | 0.42 b | 5.84 bc | 1.096 b | 15.32 ab | 0.361 b | 5.05 a | 0.075 b | 1.05 b |
| 4 | COMP 5 | 1.375 | KG/HA | HK | | | | | | | | |
| 5 | COMP 5 | .92 | KG/HA | BE | 0.40 b | 5.51 bc | 1.162 a | 16.01 a | 0.378 a | 5.20 a | 0.063 c | 0.86 c |
| 5 | COMP 5 | .92 | KG/HA | HK | | | | | | | | |
| 5 | COMP 5 | .92 | KG/HA | EF | | | | | | | | |
| LSD (P = .05) | | | | | 0.057 | 1.080 | 0.0407 | 1.097 | 0.0130 | 0.362 | 0.0095 | 0.159 |
| Standard Deviation | | | | | 0.041 | 0.784 | 0.0295 | 0.796 | 0.0095 | 0.263 | 0.0069 | 0.115 |
| CV | | | | | 8.52 | 11.64 | 2.87 | 5.65 | 2.95 | 5.98 | 9.1 | 11.04 |

Example 25

Introduction

Trial to evaluate the efficacy of Compound 5, when used in tank-mixes with fungicides for control of downy mildew, Lontrel-treated thebaine crop. Compound 5 was tested with a curative fungicide (Ridomil) and protectant fungicide (Penncozeb), in the presence and absence of an adjuvant (Activator). Sprays were applied on 2 December, with crop at hook stage, and capsules harvested on 29 January.

TABLE 25a

Effect of treatments on yield parameters.

| Trt No | Treatment Name | Rate | Rate Unit | STRAW kg/ha | SEED kg/ha | CAPSULE/ SEED RATIO | YIELD t/ha |
|---|---|---|---|---|---|---|---|
| 1 | RIDOMIL | 2.5 | KG/HA | 1572 a | 79 a | 17.496 a | 1.65 a |
| 1 | ACTIVATOR | .125 | % V/V | | | | |
| 2 | RIDOMIL | 2.5 | KG/HA | 1631 a | 75 a | 17.336 a | 1.71 a |
| 2 | ACTIVATOR | .125 | % V/V | | | | |
| 2 | COMPOUND 5 | 3 | KG/HA | | | | |
| 3 | RIDOMIL | 2.5 | KG/HA | 1680 a | 47 a | 28.113 a | 1.73 a |
| 3 | COMPOUND 5 | 3 | KG/HA | | | | |
| 4 | PENNCOZEB | 2.5 | KG/HA | 1609 a | 54 a | 23.023 a | 1.66 a |
| 4 | ACTIVATOR | .125 | % V/V | | | | |
| 4 | COMPOUND 5 | 3 | KG/HA | | | | |
| 5 | PENNCOZEB | 2.5 | KG/HA | 1703 a | 82 a | 21.317 a | 1.79 a |

TABLE 25a-continued

Effect of treatments on yield parameters.

| Trt No | Treatment Name | Rate | Rate Unit | STRAW kg/ha | SEED kg/ha | CAPSULE/ SEED RATIO | YIELD t/ha |
|---|---|---|---|---|---|---|---|
| 5 | COMPOUND 5 | 3 | KG/HA | | | | |
| 6 | PENNCOZEB | 3.5 | L/HA | 1584 a | 80 a | 25.283 a | 1.66 a |
| 6 | COMPOUND 5 | 3 | KG/HA | | | | |
| LSD (P = .05) | | | | 180.9 | 73.9 | 14.6763 | 0.164 |
| Standard Deviation | | | | 137.1 | 56.0 | 11.1243 | 0.124 |
| CV | | | | 8.41 | 80.82 | 50.35 | 7.33 |

TABLE 25b

Effect of treatments on alkaloid parameters.

| Trt No | Treatment Name | Rate | Rate Unit | STRAW MORPHINE % | MORPHINE kg/ha | STRAW THEBAINE % | THEBAINE kg/ha | STRAW ORIPAVIN % | ORIPAVINE kg/ha | STRAW CODEINE % | CODEINE kg/ha |
|---|---|---|---|---|---|---|---|---|---|---|---|
| 1 | RIDOMIL | 2.5 | KG/HA | 0.67 a | 10.49 a | 0.821 b | 12.962 b | 0.213 b | 3.368 b | 0.083 a | 1.316 a |
| 1 | ACTIVATOR | .125 | % V/V | | | | | | | | |
| 2 | RIDOMIL | 2.5 | KG/HA | 0.50 b | 7.91 b | 1.140 a | 18.698 a | 0.309 a | 5.058 a | 0.068 ab | 1.089 abc |
| 2 | ACTIVATOR | .125 | % V/V | | | | | | | | |
| 2 | COMPOUND 5 | 3 | KG/HA | | | | | | | | |
| 3 | RIDOMIL | 2.5 | KG/HA | 0.42 b | 7.06 b | 1.196 a | 20.134 a | 0.340 a | 5.705 a | 0.071 ab | 1.188 ab |
| 3 | COMPOUND 5 | 3 | KG/HA | | | | | | | | |
| 4 | PENNCOZEB | 2.5 | KG/HA | 0.39 b | 6.20 b | 1.262 a | 20.352 a | 0.337 a | 5.439 a | 0.059 b | 0.946 bc |
| 4 | ACTIVATOR | .125 | % V/V | | | | | | | | |
| 4 | COMPOUND 5 | 3 | KG/HA | | | | | | | | |
| 5 | PENNCOZEB | 2.5 | KG/HA | 0.41 b | 6.96 b | 1.212 a | 20.654 a | 0.344 a | 5.859 a | 0.063 b | 1.064 abc |
| 5 | COMPOUND 5 | 3 | KG/HA | | | | | | | | |
| 6 | PENNCOZEB | 3.5 | L/HA | 0.38 b | 6.07 b | 1.275 a | 20.235 a | 0.352 a | 5.575 a | 0.056 b | 0.889 c |
| 6 | COMPOUND 5 | 3 | KG/HA | | | | | | | | |
| LSD (P = .05) | | | | 0.168 | 2.488 | 0.2009 | 4.3048 | 0.0666 | 1.2890 | 0.0156 | 0.2669 |
| Standard Deviation | | | | 0.127 | 1.886 | 0.1522 | 3.2630 | 0.0504 | 0.9771 | 0.0118 | 0.2023 |
| CV | | | | 27.65 | 25.32 | 13.23 | 17.32 | 15.97 | 18.91 | 17.79 | 18.7 |

Example 26

Introduction

Trial to evaluate the efficacy of Compound 5, when used in tank-mixes with fungicides for control of downy mildew, Lontrel-treated thebaine crop. Compound 5 was tested with various curative fungicides (Ridomil, Acrobat, Amistar and BAS 518). Sprays were applied on 2 December, with crop at hook stage. Capsules were harvested from plots and from untreated crop (Nil) adjacent to trial on 31 January.

TABLE 26a

Effect of treatments on yield parameters.

| Trt No | Treatment Name | Rate | Rate Unit | STRAW kg/ha | SEED kg/ha | CAPSULE/SEED RATIO | YIELD t/ha |
|---|---|---|---|---|---|---|---|
| | NIL | | | 1572 | 79 | 17.496 | 1.65 |
| 1 | COMPOUND 5 | 3 | KG/HA | 1528 a | 44 b | 25.759 a | 1.57 a |
| 2 | RIDOMIL | 2.5 | KG/HA | 1589 a | 55 ab | 20.475 a | 1.64 a |
| 2 | COMPOUND 5 | 3 | KG/HA | | | | |
| 3 | ACROBAT | 2 | KG/HA | 1580 a | 61 ab | 19.197 a | 1.64 a |
| 3 | COMPOUND 5 | 3 | KG/HA | | | | |
| 4 | BAS 518 | 2 | KG/HA | 1627 a | 67 a | 19.882 a | 1.69 a |
| 4 | COMPOUND 5 | 3 | KG/HA | | | | |
| 5 | AMISTAR | .375 | KG/HA | 1585 a | 48 ab | 25.838 a | 1.63 a |
| 5 | COMPOUND 5 | 3 | KG/HA | | | | |

TABLE 26a-continued

Effect of treatments on yield parameters.

| Trt No | Treatment Name | Rate | Rate Unit | STRAW kg/ha | SEED kg/ha | CAPSULE/SEED RATIO | YIELD t/ha |
|---|---|---|---|---|---|---|---|
| 6 | RIDOMIL | 1.25 | KG/HA | 1548 a | 47 ab | 23.429 a | 1.60 a |
| 6 | AMISTAR | .188 | KG/HA | | | | |
| 6 | COMPOUND 5 | 3 | KG/HA | | | | |
| LSD (P = .05) | | | | 127.3 | 18.1 | 9.9023 | 0.125 |
| Standard Deviation | | | | 96.5 | 13.7 | 7.5057 | 0.095 |
| CV | | | | 6.12 | 25.57 | 33.46 | 5.81 |

TABLE 26b

Effect of treatments on alkaloid parameters.

| Trt No | Treatment Name | Rate | Rate Unit | STRAW MORPHINE % | STRAW MORPHINE kg/ha | STRAW THEBAINE % | STRAW THEBAINE kg/ha | STRAW ORIPAVIN % | STRAW ORIPAVINE kg/ha | STRAW CODEINE % | STRAW CODEINE kg/ha |
|---|---|---|---|---|---|---|---|---|---|---|---|
| | NIL | | | 0.67 | 10.49 | 0.821 | 12.962 | 0.213 | 3.368 | 0.083 | 1.316 |
| 1 | COMPOUND 5 | 3 | KG/HA | 0.37 a | 5.58 a | 1.085 a | 16.621 a | 0.323 a | 4.944 a | 0.057 a | 0.877 a |
| 2 | RIDOMIL | 2.5 | KG/HA | 0.36 a | 5.71 a | 1.066 a | 16.959 a | 0.305 a | 4.848 a | 0.060 a | 0.948 a |
| 2 | COMPOUND 5 | 3 | KG/HA | | | | | | | | |
| 3 | ACROBAT | 2 | KG/HA | 0.36 a | 5.69 a | 1.090 a | 17.244 a | 0.310 a | 4.904 a | 0.060 a | 0.957 a |
| 3 | COMPOUND 5 | 3 | KG/HA | | | | | | | | |
| 4 | BAS 518 | 2 | KG/HA | 0.39 a | 6.37 a | 1.035 a | 16.863 a | 0.305 a | 4.964 a | 0.063 a | 1.021 a |
| 4 | COMPOUND 5 | 3 | KG/HA | | | | | | | | |
| 5 | AMISTAR | .375 | KG/HA | 0.36 a | 5.64 a | 1.156 a | 18.365 a | 0.317 a | 5.038 a | 0.056 a | 0.897 a |
| 5 | COMPOUND 5 | 3 | KG/HA | | | | | | | | |
| 6 | RIDOMIL | 1.25 | KG/HA | 0.39 a | 6.06 a | 1.054 a | 16.345 a | 0.302 a | 4.676 a | 0.062 a | 0.966 a |
| 6 | AMISTAR | .188 | KG/HA | | | | | | | | |
| 6 | COMPOUND 5 | 3 | KG/HA | | | | | | | | |
| LSD (P = .05) | | | | 0.039 | 0.734 | 0.1209 | 2.7331 | 0.0290 | 0.7056 | 0.0072 | 0.1493 |
| Standard Deviation | | | | 0.030 | 0.556 | 0.0917 | 2.0717 | 0.0219 | 0.5348 | 0.0054 | 0.1132 |
| CV | | | | 7.99 | 9.52 | 8.48 | 12.14 | 7.07 | 10.92 | 9.07 | 11.98 |

Example 27

Introduction

Trial to evaluate the efficacy of Compound 5 at two different water rates (153 and 250 L/ha) and when mixed with two different rates (0.1 and 1 L/ha) of Compound 2. The trial was established Lontrel-treated thebaine crop and sprays were applied on 10 December, with crop at hook stage. Capsules were harvested from plots on 12 February.

TABLE 27a

Effect of treatments on yield parameters.

| Trt No | Treatment Name | Rate | Rate Unit | Water Vol | STRAW kg/ha | SEED kg/ha | CAPSULE/SEED RATIO | YIELD t/ha |
|---|---|---|---|---|---|---|---|---|
| 1 | NIL | | | | 1033 a | 205 a | 4.805 ab | 1.24 a |
| 2 | COMPOUND 5 | 3 | KG/HA | 153 L/HA | 1027 a | 176 a | 4.319 b | 1.20 a |
| 3 | COMPOUND 5 | 3 | KG/HA | 250 L/HA | 1091 a | 205 a | 4.047 b | 1.30 a |
| 4 | COMPOUND 5 | 3 | KG/HA | 153 L/HA | 1039 a | 190 a | 4.252 b | 1.23 a |
| 4 | COMPOUND 2 | .1 | L/HA | 153 L/HA | | | | |
| 5 | COMPOUND 5 | 3 | KG/HA | 153 L/HA | 1023 a | 148 a | 5.910 a | 1.17 a |
| 5 | COMPOUND 2 | 1 | L/HA | 153 L/HA | | | | |
| LSD (P = .05) | | | | | 143.1 | 75.2 | 1.2474 | 0.188 |
| Standard Deviation | | | | | 103.8 | 54.5 | 0.9051 | 0.136 |
| CV | | | | | 9.96 | 29.53 | 19.4 | 11.1 |

TABLE 27b

Effect of treatments on alkaloid parameters.

| Trt No | Treatment Name | Rate | Rate Unit | Water Vol | STRAW MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|---|---|
| 1 | NIL | | | | 0.89 a | 9.20 a | 0.894 d | 9.10 d | 0.247 c | 2.58 b | 0.114 a | 1.16 a |
| 2 | COMP 5 | 3 | KG/HA | 153 L/HA | 0.47 b | 4.86 bc | 1.386 c | 14.18 c | 0.405 a | 4.15 a | 0.076 b | 0.78 b |
| 3 | COMP 5 | 3 | KG/HA | 250 L/HA | 0.50 b | 5.44 b | 1.375 c | 15.01 bc | 0.424 a | 4.62 a | 0.074 b | 0.82 b |
| 4 | COMP 5 | 3 | KG/HA | 153 L/HA | 0.31 c | 3.26 cd | 1.614 b | 16.73 b | 0.432 a | 4.53 a | 0.042 c | 0.43 c |
| 4 | COMP 2 | .1 | L/HA | 153 L/HA | | | | | | | | |
| 5 | COMP 5 | 3 | KG/HA | 153 L/HA | 0.20 d | 2.08 d | 1.890 a | 19.36 a | 0.276 b | 2.84 b | 0.026 d | 0.26 c |
| 5 | COMP 2 | 1 | L/HA | 153 L/HA | | | | | | | | |
| LSD (P = .05) | | | | | 0.082 | 1.787 | 0.0716 | 2.025 | 0.0280 | 0.461 | 0.0134 | 0.211 |
| Standard Deviation | | | | | 0.059 | 1.297 | 0.0519 | 1.470 | 0.0203 | 0.335 | 0.0097 | 0.153 |
| CV | | | | | 12.5 | 26.11 | 3.63 | 9.88 | 5.69 | 8.95 | 14.69 | 22.27 |

Example 28

Introduction

Trial to evaluate the application of different rates of Compound 4 (applied with 0.125% v/v Activator adjuvant), at five different dates and in Lontrel-treated or otherwise untreated morphine crop. Sprays were applied to single plots on 14, 20 and 28 November, 11 and 17 December, with crop at 10-12 leaf, row cover, early run-up, bud-emergence and hook stages, respectively. Lontrel (1 L/ha) was applied across half of all plots on 20 November. Capsules were harvested from 2 m×2 m quadrats placed in each half-plot on 19 February. Results for plots sprayed at each sowing date were used as replicates to calculate means for different rates of Compound 4 (Tables 28a&b). Results for alkaloid assays and production of crop sprayed with 1 kg/ha Compound 4 at early run-up, bud-emergence and hook stages in individual (unreplicated) plots are shown in Table 28c.

TABLE 28a

Effect of treatments on yield parameters.

| Trt No | Treatment Name | Rate | Rate Unit | STRAW kg/ha | SEED kg/ha | CAPSULE/SEED RATIO | YIELD t/ha |
|---|---|---|---|---|---|---|---|
| 1 | LONTREL | 1 | L/HA | 2175 a | 73 b | 22.484 a | 2.25 b |
| 1 | NIL | | | | | | |
| 2 | LONTREL | 1 | L/HA | 2223 a | 79 b | 22.735 a | 2.30 b |
| 2 | COMPOUND 4 | .02 | KG/HA | | | | |
| 3 | LONTREL | 1 | L/HA | 2050 ab | 73 b | 20.581 a | 2.12 b |
| 3 | COMPOUND 4 | .1 | KG/HA | | | | |
| 4 | LONTREL | 1 | L/HA | 2215 a | 79 b | 20.642 a | 2.29 b |
| 4 | COMPOUND 4 | .2 | KG/HA | | | | |
| 5 | LONTREL | 1 | L/HA | 2149 a | 71 b | 21.363 a | 2.22 b |
| 5 | COMPOUND 4 | 1 | KG/HA | | | | |
| 6 | NIL | | | 1800 c | 2038 a | 0.614 b | 3.84 a |
| 6 | NIL | | | | | | |
| 7 | NIL | | | 1806 c | 2026 a | 0.618 b | 3.83 a |
| 7 | COMPOUND 4 | .02 | KG/HA | | | | |
| 8 | NIL | | | 1764 c | 1976 a | 0.619 b | 3.74 a |
| 8 | COMPOUND 4 | .1 | KG/HA | | | | |
| 9 | NIL | | | 1802 c | 2026 a | 0.617 b | 3.83 a |
| 9 | COMPOUND 4 | .2 | KG/HA | | | | |
| 10 | NIL | | | 1894 bc | 2159 a | 0.611 b | 4.05 a |
| 10 | COMPOUND 4 | 1 | KG/HA | | | | |
| LSD (P = .05) | | | | 198.3 | 202.2 | 6.2954 | 0.323 |
| Standard Deviation | | | | 155.1 | 158.2 | 4.9252 | 0.253 |
| CV | | | | 7.8 | 14.93 | 44.42 | 8.29 |

TABLE 28b

Effect of treatments on alkaloid parameters.

| Trt No | Treatment Name | Rate | Rating Unit Rate Unit | STRAW MORPHINE % | MORPHINE kg/ha | STRAW THEBAINE % | THEBAINE kg/ha | STRAW O'PAVIN % | ORIPAVINE kg/ha | STRAW CODEINE % | CODEINE kg/ha |
|---|---|---|---|---|---|---|---|---|---|---|---|
| 1 | LONTREL | 1 | L/HA | 1.99 a-d | 43.38 a | 0.105 bc | 2.292 b | 0.010 b | 0.226 bc | 0.122 b | 2.659 bc |
| 1 | NIL | | | | | | | | | | |
| 2 | LONTREL | 1 | L/HA | 1.89 bcd | 42.20 ab | 0.105 bc | 2.327 b | 0.009 b | 0.212 bc | 0.124 b | 2.744 bc |
| 2 | COMP 4 | .02 | KG/HA | | | | | | | | |
| 3 | LONTREL | 1 | L/HA | 1.89 bcd | 39.01 abc | 0.105 bc | 2.175 b | 0.010 b | 0.212 bc | 0.124 b | 2.557 bc |
| 3 | COMP 4 | .1 | KG/HA | | | | | | | | |
| 4 | LONTREL | 1 | L/HA | 1.85 cde | 41.18 abc | 0.114 bc | 2.503 b | 0.012 b | 0.269 bc | 0.136 b | 3.006 ab |
| 4 | COMP 4 | .2 | KG/HA | | | | | | | | |
| 5 | LONTREL | 1 | L/HA | 1.66 e | 35.98 bc | 0.240 ab | 5.049 a | 0.046 ab | 0.956 ab | 0.162 a | 3.496 a |
| 5 | COMP 4 | 1 | KG/HA | | | | | | | | |
| 6 | NIL | | | 2.09 ab | 37.51 abc | 0.046 c | 0.842 b | 0.006 b | 0.102 c | 0.075 c | 1.356 d |
| 6 | NIL | | | | | | | | | | |
| 7 | NIL | | | 2.16 a | 39.23 abc | 0.053 c | 0.974 b | 0.007 b | 0.126 c | 0.082 c | 1.490 d |
| 7 | COMP 4 | .02 | KG/HA | | | | | | | | |
| 8 | NIL | | | 2.03 a-d | 35.96 bc | 0.054 c | 0.967 b | 0.007 b | 0.126 c | 0.080 c | 1.434 d |
| 8 | COMP 4 | .1 | KG/HA | | | | | | | | |
| 9 | NIL | | | 2.06 abc | 37.06 abc | 0.072 c | 1.296 b | 0.011 b | 0.195 c | 0.095 c | 1.700 d |
| 9 | COMP 4 | .2 | KG/HA | | | | | | | | |
| 10 | NIL | | | 1.82 de | 34.67 c | 0.277 a | 5.132 a | 0.074 a | 1.369 a | 0.122 b | 2.314 c |
| 10 | COMP 4 | 1 | KG/HA | | | | | | | | |
| LSD (P = .05) | | | | 0.194 | 6.229 | 0.1225 | 2.2692 | 0.0365 | 0.6766 | 0.0255 | 0.5288 |
| Std Dev | | | | 0.152 | 4.874 | 0.0958 | 1.7753 | 0.0286 | 0.5293 | 0.0199 | 0.4137 |
| CV | | | | 7.79 | 12.62 | 81.84 | 75.36 | 148.41 | 139.55 | 17.78 | 18.18 |

TABLE 28c

Effect of treatments on alkaloid parameters.

| Trt No | Treatment Name | GS | MORPHINE % | MORPHINE kg/ha | STRAW THEBAINE % | THEBAINE kg/ha | STRAW O'PAVINE % | ORIPAVINE kg/ha | STRAW CODEINE % | CODEINE kg/ha |
|---|---|---|---|---|---|---|---|---|---|---|
| 1 | LONTREL | ERU | 1.96 | 43.63 | 0.108 | 2.404 | 0.010 | 0.223 | 0.119 | 2.649 |
| 2 | COMP 4 | ERU | 1.96 | 45.75 | 0.121 | 2.824 | 0.013 | 0.303 | 0.154 | 3.594 |
| 3 | LONTREL | BUD-EM | 2.05 | 49.12 | 0.104 | 2.492 | 0.015 | 0.359 | 0.130 | 3.115 |
| 4 | COMP 4 | BUD-EM | 1.72 | 38.91 | 0.321 | 7.261 | 0.069 | 1.561 | 0.204 | 4.614 |
| 5 | LONTREL | HOOK | 2.03 | 41.53 | 0.105 | 2.148 | 0.010 | 0.205 | 0.124 | 2.537 |
| 6 | COMP 4 | HOOK | 1.41 | 27.78 | 0.549 | 10.815 | 0.125 | 2.463 | 0.240 | 4.728 |
| 7 | NIL | ERU | 1.94 | 36.65 | 0.034 | 0.642 | 0.005 | 0.094 | 0.060 | 1.133 |
| 8 | COMP 4 | ERU | 2.05 | 40.96 | 0.115 | 2.298 | 0.020 | 0.400 | 0.130 | 2.597 |
| 9 | NIL | BUD-EM | 2.18 | 44.49 | 0.072 | 1.470 | 0.008 | 0.163 | 0.091 | 1.857 |
| 10 | COMP 4 | BUD-EM | 1.60 | 29.17 | 0.464 | 8.459 | 0.144 | 2.625 | 0.146 | 2.662 |
| 11 | NIL | HOOK | 2.20 | 35.27 | 0.055 | 0.882 | 0.007 | 0.112 | 0.083 | 1.330 |
| 12 | COMP 4 | HOOK | 1.50 | 27.45 | 0.668 | 12.224 | 0.187 | 3.422 | 0.137 | 2.507 |

Example 29

Introduction

Trial to evaluate the effect of application of methyl jasmonate to morphine crop. Treatments were applied on 10 and 20 December, with crop at early flowering and early green capsule stages, respectively. Capsules were harvested on 12 February.

TABLE 29

Effect of methyl jasmonate on capsule/seed ratio and alkaloid assay parameters.

| Trt No | Treatment Name | Rate | Rate Unit | Grow Stg | CAPSULE/ SEED RATIO | STRAW MORPHINE % | STRAW THEBAINE % | STRAW O'PAVINE % | STRAW CODEINE % |
|---|---|---|---|---|---|---|---|---|---|
| 1 | NIL | | | | 0.558 b | 1.99 a | 0.030 c | 0.005 c | 0.043 c |
| 2 | METHYL JAS | .15 | L/ha | EF | 0.575 a | 2.04 a | 0.042 b | 0.009 b | 0.064 b |
| 3 | METHYL JAS | .3 | L/ha | EF | 0.581 a | 2.09 a | 0.051 a | 0.011 a | 0.075 a |
| 4 | METHYL JAS | .15 | L/ha | GCAPS | 0.577 a | 2.01 a | 0.033 c | 0.005 c | 0.044 c |

TABLE 29-continued

Effect of methyl jasmonate on capsule/seed ratio and alkaloid assay parameters.

| Trt No | Treatment Name | Rate | Rate Unit | Grow Stg | CAPSULE/ SEED RATIO | STRAW MORPHINE % | STRAW THEBAINE % | STRAW O'PAVINE % | STRAW CODEINE % |
|---|---|---|---|---|---|---|---|---|---|
| 5 | METHYL JAS | .3 | L/ha | GCAPS | 0.577 a | 2.04 a | 0.029 c | 0.004 c | 0.042 c |
| LSD (P = .05) | | | | | 0.0120 | 0.133 | 0.0074 | 0.0021 | 0.0070 |
| Standard Deviation | | | | | 0.0087 | 0.097 | 0.0054 | 0.0015 | 0.0051 |
| CV | | | | | 1.52 | 4.76 | 14.48 | 22.7 | 9.52 |

Example 30

Introduction

Trial to compare a single application of 1 L/ha Compound 1 with sequential applications totaling 1 L/ha Compound 1, in Lontrel-treated thebaine crop. Sprays were applied on 15 November (ground cover), 26 November (mid-late run-up), and 2 December (bud-emergence). Capsules were harvested on 10 February.

TABLE 30a

Effect of treatments on yield parameters.

| Trt No. | Treatment Name | Rate | Rate Unit | Grow Stg | CAPSULE/ SEED RATIO | STRAW kg/ha | SEED kg/ha | YIELD t/ha |
|---|---|---|---|---|---|---|---|---|
| 1 | LONTREL | .8 | L/HA | GC | 2.431 b | 903 a | 297 a | 1.20 a |
| 2 | LONTREL | .8 | L/HA | GC | 2.991 b | 856 a | 206 b | 1.06 a |
| 2 | COMPOUND 1 | 1 | L/HA | GC | | | | |
| 3 | LONTREL | .8 | L/HA | GC | 3.579 ab | 905 a | 186 b | 1.09 a |
| 3 | COMPOUND 1 | 1 | L/HA | M-LRU | | | | |
| 4 | LONTREL | .8 | L/HA | GC | 3.649 ab | 857 a | 180 b | 1.04 a |
| 4 | COMPOUND 1 | .33 | L/HA | GC | | | | |
| 4 | COMPOUND 1 | .33 | L/HA | M-LRU | | | | |
| 4 | COMPOUND 1 | .33 | L/HA | BE | | | | |
| 5 | LONTREL | .8 | L/HA | GC | 4.618 a | 904 a | 141 b | 1.05 a |
| 5 | COMPOUND 1 | .5 | L/HA | GC | | | | |
| 5 | COMPOUND 1 | .5 | L/HA | BE | | | | |
| LSD (P = .05) | | | | | 1.3388 | 170.2 | 63.1 | 0.156 |
| Standard Deviation | | | | | 0.9714 | 123.5 | 45.8 | 0.113 |
| CV | | | | | 28.13 | 13.96 | 22.68 | 10.39 |

TABLE 30b

Effect of treatments on alkaloid parameters.

| Trt No | Treatment Name | Rate | Grow Stg | STRAW MORPHINE % | MORPHINE kg/ha | STRAW CODEINE % | CODEINE kg/ha | STRAW THEBAINE % | THEBAINE kg/ha | STRAW O'PAVINE % | ORIPAVINE kg/ha |
|---|---|---|---|---|---|---|---|---|---|---|---|
| 1 | LONTREL | .8 | GC | 0.63 a | 5.71 a | 0.082 a | 0.741 a | 1.374 d | 12.459 b | 0.359 b | 3.257 a |
| 2 | LONTREL | .8 | GC | 0.22 b | 1.93 b | 0.038 b | 0.324 b | 1.744 c | 14.933 ab | 0.420 a | 3.632 a |
| 2 | COMP. 1 | 1 | GC | | | | | | | | |
| 3 | LONTREL | .8 | GC | 0.17 c | 1.51 bc | 0.027 b | 0.246 b | 2.011 a | 18.170 a | 0.424 a | 3.873 a |
| 3 | COMP. 1 | 1 | M-LRU | | | | | | | | |
| 4 | LONTREL | .8 | GC | 0.13 c | 1.13 c | 0.044 b | 0.357 b | 1.971 ab | 16.835 a | 0.377 b | 3.221 a |
| 4 | COMP. 1 | .33 | GC | | | | | | | | |
| 4 | COMP. 1 | .33 | M-LRU | | | | | | | | |
| 4 | COMP. 1 | .33 | BE | | | | | | | | |
| 5 | LONTREL | .8 | GC | 0.13 c | 1.15 c | 0.030 b | 0.269 b | 1.897 b | 17.120 a | 0.368 b | 3.296 a |
| 5 | COMP. 1 | .5 | GC | | | | | | | | |
| 5 | COMP. 1 | .5 | BE | | | | | | | | |
| LSD (P = .05) | | | | 0.044 | 0.495 | 0.0183 | 0.1547 | 0.0782 | 3.0432 | 0.0384 | 0.9352 |
| Std Deviation | | | | 0.032 | 0.359 | 0.0132 | 0.1123 | 0.0568 | 2.2082 | 0.0279 | 0.6786 |
| CV | | | | 12.37 | 15.72 | 29.99 | 28.98 | 3.16 | 13.89 | 7.15 | 19.64 |

Example 31

Introduction

Trial to evaluate reduced rates of Compound 1, tank-mixed with a soybean oil adjuvant, in Lontrel-treated thebaine crop. Sprays were applied on 4 November (row cover) and 29 November (late run-up), with 0.9 L/ha Lontrel applied to all plots on 10 November. Capsules were harvested on 16 February.

SprayTech™ oil is manufactured by SprayTech Inc and contains 95% soybean oil.

TABLE 31a

Effect of treatments on yield parameters.

| Trt No. | Treatment Name | Rate | Rate Unit | Grow Stg | CAPSULE/ SEED RATIO | STRAW kg/ha | SEED kg/ha | YIELD t/ha |
|---|---|---|---|---|---|---|---|---|
| 1 | NIL | | | | 1.237 a | 2136 a | 1214 a | 3.35 a |
| 2 | COMPOUND 1 | .5 | L/HA | RC | 1.241 a | 1972 a | 1116 a | 3.09 b |
| 2 | COMPOUND 1 | .5 | L/HA | LRU | | | | |
| 3 | COMPOUND 1 | .5 | L/HA | RC | 1.346 a | 2054 a | 1069 a | 3.12 ab |
| 3 | SPRAYTECH OIL | .5 | L/HA | RC | | | | |
| 3 | COMPOUND 1 | .5 | L/HA | LRU | | | | |
| 3 | SPRAYTECH OIL | .5 | L/HA | LRU | | | | |
| 4 | COMPOUND 1 | .4 | L/HA | RC | 1.260 a | 2013 a | 1131 a | 3.15 ab |
| 4 | SPRAYTECH OIL | .4 | L/HA | RC | | | | |
| 4 | COMPOUND 1 | .4 | L/HA | LRU | | | | |
| 4 | SPRAYTECH OIL | .4 | L/HA | LRU | | | | |
| 5 | COMPOUND 1 | .35 | L/HA | RC | 1.220 a | 2023 a | 1181 a | 3.20 ab |
| 5 | SPRAYTECH OIL | .35 | L/HA | RC | | | | |
| 5 | COMPOUND 1 | .35 | L/HA | LRU | | | | |
| 5 | SPRAYTECH OIL | .35 | L/HA | LRU | | | | |
| LSD (P = .05) | | | | | 0.2203 | 186.7 | 161.0 | 0.237 |
| Standard Deviation | | | | | 0.1598 | 135.5 | 116.8 | 0.172 |
| CV | | | | | 12.68 | 6.64 | 10.22 | 5.4 |

TABLE 31b

Effect of treatments on alkaloid parameters.

| Rating Unit | | | | STRAW | | STRAW | | STRAW | | STRAW | |
|---|---|---|---|---|---|---|---|---|---|---|---|
| Trt No. | Treatment Name | Rate | Grow Stg | MORPHINE % | MORPHINE kg/ha | CODEINE % | CODEINE kg/ha | THEBAINE % | THEBAINE kg/ha | O'PAVINE % | ORIPAVINE kg/ha |
| 1 | NIL | | | 1.06 a | 22.76 a | 0.073 a | 1.55 a | 0.900 c | 19.12 c | 0.324 c | 6.90 b |
| 2 | COMPOUND 1 | .5 | RC | 0.43 bc | 8.41 bc | 0.032 bc | 0.62 b | 1.527 a | 30.10 ab | 0.604 a | 11.92 a |
| 2 | COMPOUND 1 | .5 | LRU | | | | | | | | |
| 3 | COMPOUND 1 | .5 | RC | 0.34 c | 6.98 a | 0.029 c | 0.60 b | 1.545 a | 31.63 a | 0.592 a | 12.14 a |
| 3 | S'TECH OIL | .5 | RC | | | | | | | | |
| 3 | COMPOUND 1 | .5 | LRU | | | | | | | | |
| 3 | S'TECH OIL | .5 | LRU | | | | | | | | |
| 4 | COMPOUND 1 | .4 | RC | 0.50 b | 10.09 b | 0.033 bc | 0.67 b | 1.376 b | 27.69 b | 0.553 b | 11.11 a |
| 4 | S'TECH OIL | .4 | RC | | | | | | | | |
| 4 | COMPOUND 1 | .4 | LRU | | | | | | | | |
| 4 | S'TECH OIL | .4 | LRU | | | | | | | | |
| 5 | COMPOUND 1 | .35 | RC | 0.50 b | 10.02 b | 0.038 b | 0.75 b | 1.441 b | 29.12 ab | 0.559 b | 11.33 a |
| 5 | S'TECH OIL | .35 | RC | | | | | | | | |
| 5 | COMPOUND 1 | .35 | LRU | | | | | | | | |
| 5 | S'TECH OIL | .35 | LRU | | | | | | | | |
| LSD (P = .05) | | | | 0.117 | 2.593 | 0.0075 | 0.1694 | 0.0811 | 3.105 | 0.0323 | 1.3049 |
| Standard Deviation | | | | 0.085 | 1.882 | 0.0054 | 0.1229 | 0.0589 | 2.253 | 0.0234 | 0.9468 |
| CV | | | | 14.97 | 16.15 | 13.31 | 14.65 | 4.33 | 8.18 | 4.45 | 8.87 |

Example 32

Introduction

Trial to evaluate reduced rates of Compound 1, tank-mixed with Codacide a vegetable oil adjuvant, in Lontrel-treated thebaine crop. Sprays were applied on 3 November (row cover) and 25 November (late run-up), with 0.9 L/ha Lontrel applied to all plots on 10 November. Capsules were harvested on 17 February.

Codacide™ is manufactured by Microcide Limited and is a 95% natural vegetable oil adjuvant.

TABLE 32a

Effect of treatments on yield parameters.

| Trt No. | Treatment Name | Rate | Rate Unit | Grow Stg | CAPSULE/ SEED RATIO | STRAW kg/ha | SEED kg/ha | YIELD t/ha |
|---|---|---|---|---|---|---|---|---|
| 1 | NIL | | | | 3.525 c | 1724 a | 348 a | 2.07 a |
| 2 | COMPOUND 1 | .5 | L/HA | RC | 4.636 ab | 1700 a | 261 b | 1.96 a |
| 2 | COMPOUND 1 | .5 | L/HA | LRU | | | | |
| 3 | COMPOUND 1 | .5 | L/HA | RC | 4.524 ab | 1646 a | 263 b | 1.91 a |
| 3 | CODACIDE OIL | .5 | L/HA | RC | | | | |
| 3 | COMPOUND 1 | .5 | L/HA | LRU | | | | |
| 3 | CODACIDE OIL | .5 | L/HA | LRU | | | | |
| 4 | COMPOUND 1 | .4 | L/HA | RC | 3.924 bc | 1588 a | 283 b | 1.87 a |
| 4 | CODACIDE OIL | .4 | L/HA | RC | | | | |
| 4 | COMPOUND 1 | .4 | L/HA | LRU | | | | |
| 4 | CODACIDE OIL | .4 | L/HA | LRU | | | | |
| 5 | COMPOUND 1 | .35 | L/HA | RC | 5.121 a | 1652 a | 240 b | 1.89 a |
| 5 | CODACIDE OIL | .35 | L/HA | RC | | | | |
| 5 | COMPOUND 1 | .35 | L/HA | LRU | | | | |
| 5 | CODACIDE OIL | .35 | L/HA | LRU | | | | |
| LSD (P = .05) | | | | | 0.7782 | 213.8 | 55.4 | 0.261 |
| Standard Deviation | | | | | 0.5647 | 155.1 | 40.2 | 0.189 |
| CV | | | | | 12.99 | 9.33 | 14.42 | 9.75 |

TABLE 32b

Effect of treatments on alkaloid parameters.

| Trt No. | Treatment Name | Rate | Grow Stg | STRAW MORPHINE % | MORPHINE kg/ha | STRAW CODEINE % | CODEINE kg/ha | STRAW THEBAINE % | THEBAINE kg/ha | STRAW O'PAVIN % | ORIPAVINE kg/ha |
|---|---|---|---|---|---|---|---|---|---|---|---|
| 1 | NIL | | | 0.74 a | 12.86 a | 0.134 a | 2.31 a | 1.185 c | 20.44 b | 0.251 c | 4.349 b |
| 2 | COMPOUND 1 | .5 | RC | 0.15 c | 2.51 b | 0.038 c | 0.65 b | 1.851 a | 31.48 a | 0.374 a | 6.366 a |
| 2 | COMPOUND 1 | .5 | LRU | | | | | | | | |
| 3 | COMPOUND 1 | .5 | RC | 0.15 c | 2.42 b | 0.038 c | 0.63 b | 1.799 a | 29.68 a | 0.352 b | 5.806 a |
| 3 | CODACIDE | .5 | RC | | | | | | | | |
| 3 | COMPOUND 1 | .5 | LRU | | | | | | | | |
| 3 | CODACIDE | .5 | LRU | | | | | | | | |
| 4 | COMPOUND 1 | .4 | RC | 0.18 b | 2.79 b | 0.044 b | 0.69 b | 1.792 a | 28.43 a | 0.379 a | 6.065 a |
| 4 | CODACIDE | .4 | RC | | | | | | | | |
| 4 | COMPOUND 1 | .4 | LRU | | | | | | | | |
| 4 | CODACIDE | .4 | LRU | | | | | | | | |
| 5 | COMPOUND 1 | .35 | RC | 0.20 b | 3.29 b | 0.046 b | 0.75 b | 1.725 b | 28.52 a | 0.377 a | 6.222 a |
| 5 | CODACIDE | .35 | RC | | | | | | | | |
| 5 | COMPOUND 1 | .35 | LRU | | | | | | | | |
| 5 | CODACIDE | .35 | LRU | | | | | | | | |
| LSD (P = .05) | | | | 0.026 | 1.110 | 0.0046 | 0.184 | 0.0612 | 3.8330 | 0.0190 | 0.9118 |
| Standard Deviation | | | | 0.019 | 0.805 | 0.0034 | 0.133 | 0.0444 | 2.7813 | 0.0138 | 0.6616 |
| CV | | | | 6.6 | 16.87 | 5.61 | 13.24 | 2.66 | 10.04 | 3.98 | 11.48 |

Example 33

Introduction

Trial to evaluate reduced rates of Compound 1, tank-mixed with a rapeseed oil adjuvant, in Lontrel-treated thebaine crop. Sprays were applied on 23 November (ground cover) and 1 December (late run-up), with 1 L/ha Lontrel applied to all plots on 1 December. Capsules were harvested on 15 February.

TABLE 33a

Effect of treatments on yield parameters.

| Trt No. | Treatment Name | Rate | Rate Unit | Grow Stg | CAPSULE/ SEED RATIO | STRAW kg/ha | SEED kg/ha | YIELD t/ha |
|---|---|---|---|---|---|---|---|---|
| 1 | NIL | | | | 1.808 b | 1032 bc | 410 a | 1.44 a |
| 2 | COMPOUND 1 | .5 | L/HA | RC | 2.594 a | 1161 a | 318 b | 1.48 a |
| 2 | COMPOUND 1 | .5 | L/HA | LRU | | | | |
| 3 | COMPOUND 1 | .5 | L/HA | RC | 2.651 a | 1106 ab | 302 b | 1.41 a |
| 3 | CODACIDE OIL | .5 | L/HA | RC | | | | |
| 3 | COMPOUND 1 | .5 | L/HA | LRU | | | | |
| 3 | CODACIDE OIL | .5 | L/HA | LRU | | | | |
| 4 | COMPOUND 1 | .4 | L/HA | RC | 2.690 a | 980 c | 253 b | 1.23 b |
| 4 | CODACIDE OIL | .4 | L/HA | RC | | | | |
| 4 | COMPOUND 1 | .4 | L/HA | LRU | | | | |
| 4 | CODACIDE OIL | .4 | L/HA | LRU | | | | |
| 5 | COMPOUND 1 | .35 | L/HA | RC | 2.730 a | 1149 a | 308 b | 1.46 a |
| 5 | CODACIDE OIL | .35 | L/HA | RC | | | | |
| 5 | COMPOUND 1 | .35 | L/HA | LRU | | | | |
| 5 | CODACIDE OIL | .35 | L/HA | LRU | | | | |
| LSD (P = .05) | | | | | 0.4080 | 85.5 | 78.3 | 0.135 |
| Standard Deviation | | | | | 0.2961 | 62.0 | 56.8 | 0.098 |
| CV | | | | | 11.87 | 5.71 | 17.84 | 7.0 |

TABLE 33b

Effect of treatments on alkaloid parameters.

| Trt No. | Treatment Name | Rate | Grow Stg | STRAW MORPHINE % | MORPHINE kg/ha | STRAW CODEINE % | CODEINE kg/ha | STRAW THEBAINE % | THEBAINE kg/ha | STRAW O'PAVIN % | ORIPAVINE kg/ha |
|---|---|---|---|---|---|---|---|---|---|---|---|
| 1 | NIL | | | 0.43 a | 4.47 a | 0.057 a | 0.58 b | 1.29 b | 13.32 c | 0.259 a | 2.69 ab |
| 2 | COMPOUND 1 | .5 | RC | 0.09 b | 1.01 b | 0.027 c | 0.31 b | 1.64 a | 19.08 a | 0.261 a | 3.01 a |
| 2 | COMPOUND 1 | .5 | LRU | | | | | | | | |
| 3 | COMPOUND 1 | .5 | RC | 0.09 b | 0.99 b | 0.030 bc | 0.33 b | 1.67 a | 18.42 a | 0.248 a | 2.75 ab |
| 3 | CODACIDE | .5 | RC | | | | | | | | |
| 3 | COMPOUND 1 | .5 | LRU | | | | | | | | |
| 3 | CODACIDE | .5 | LRU | | | | | | | | |
| 4 | COMPOUND 1 | .4 | RC | 0.09 b | 0.91 b | 0.035 b | 0.33 b | 1.69 a | 16.56 b | 0.259 a | 2.57 b |
| 4 | CODACIDE | .4 | RC | | | | | | | | |
| 4 | COMPOUND 1 | .4 | LRU | | | | | | | | |
| 4 | CODACIDE | .4 | LRU | | | | | | | | |
| 5 | COMPOUND 1 | .35 | RC | 0.10 b | 1.18 b | 0.033 b | 0.37 b | 1.66 a | 19.03 a | 0.263 a | 3.06 a |
| 5 | CODACIDE | .35 | RC | | | | | | | | |
| 5 | COMPOUND 1 | .35 | LRU | | | | | | | | |
| 5 | CODACIDE | .35 | LRU | | | | | | | | |
| LSD (P = .05) | | | | 0.020 | 0.477 | 0.0054 | 0.0763 | 0.0809 | 1.4594 | 0.0285 | 0.3958 |
| Std Deviation | | | | 0.015 | 0.346 | 0.0039 | 0.0554 | 0.0587 | 1.0590 | 0.0207 | 0.2872 |
| CV | | | | 9.19 | 20.24 | 10.78 | 14.43 | 3.69 | 6.13 | 8.01 | 10.2 |

Example 34

Introduction

Trial to evaluate combinations of Compound 1+Sunny, in Lontrel-treated thebaine crop. Sprays were applied on 9 November, with crop at ground cover and 0.9 L/ha Lontrel applied over the whole trial on 10 November. Capsules were harvested on 18 February.

Sunny™ is manufactured by Aquamarine BV and is a plant growth regulator. It contains the active ingredient uniconazole-p.

TABLE 34a

Effect of treatments on yield parameters.

| Trt No. | Treatment Name | Rate | Rate Unit | Grow Stg | CAPSULE/SEED RATIO | STRAW kg/ha | SEED kg/ha | YIELD t/ha |
|---|---|---|---|---|---|---|---|---|
| 1 | NIL | | | | 1.707 ab | 1395 a | 870 b | 2.27 ab |
| 2 | COMPOUND 1 | 1 | L/HA | GC | 1.922 a | 1286 a | 808 b | 2.09 b |
| 3 | SUNNY | 1 | L/HA | GC | 1.352 ab | 1414 a | 1038 a | 2.45 a |
| 3 | CODACIDE OIL | 1 | L/HA | GC | | | | |
| 4 | COMPOUND 1 | 1 | L/HA | GC | 1.362 ab | 1428 a | 932 ab | 2.36 ab |
| 4 | SUNNY | 1 | L/HA | GC | | | | |
| 4 | CODACIDE OIL | 1 | L/HA | GC | | | | |
| 5 | COMPOUND 1 | .5 | L/HA | GC | 1.190 b | 1287 a | 957 ab | 2.24 ab |
| 5 | SUNNY | 1 | L/HA | GC | | | | |
| 5 | CODACIDE OIL | 1 | L/HA | GC | | | | |
| LSD (P = .05) | | | | | 0.6294 | 165.6 | 148.3 | 0.281 |
| Standard Deviation | | | | | 0.4567 | 120.2 | 107.6 | 0.204 |
| CV | | | | | 30.31 | 8.82 | 11.68 | 8.94 |

TABLE 34b

Effect of treatments on alkaloid parameters.

| Trt No. | Treatment Name | Rate | Rate Unit | STRAW MORPHINE % | MORPHINE kg/ha | STRAW CODEINE % | CODEINE kg/ha | STRAW THEBAINE % | THEBAINE kg/ha | STRAW O'PAVIN % | ORIPAVINE kg/ha |
|---|---|---|---|---|---|---|---|---|---|---|---|
| 1 | NIL | | | 0.76 b | 10.56 b | 0.107 a | 1.56 a | 1.035 c | 14.63 c | 0.316 b | 4.34 c |
| 2 | COMPOUND 1 | 1 | L/HA | 0.29 d | 3.72 d | 0.054 b | 0.69 b | 1.458 a | 18.89 b | 0.487 a | 6.30 ab |
| 3 | SUNNY | 1 | L/HA | 0.85 a | 12.05 a | 0.112 a | 1.59 a | 1.079 c | 15.30 c | 0.323 b | 4.56 c |
| 3 | CODACIDE | 1 | L/HA | | | | | | | | |
| 4 | COMPOUND 1 | 1 | L/HA | 0.33 d | 4.65 cd | 0.052 b | 0.74 b | 1.488 a | 21.35 a | 0.493 a | 7.08 a |
| 4 | SUNNY | 1 | L/HA | | | | | | | | |
| 4 | CODACIDE | 1 | L/HA | | | | | | | | |
| 5 | COMPOUND 1 | .5 | L/HA | 0.44 c | 5.70 c | 0.060 b | 0.77 b | 1.362 b | 17.52 b | 0.467 a | 6.01 b |
| 5 | SUNNY | 1 | L/HA | | | | | | | | |
| 5 | CODACIDE | 1 | L/HA | | | | | | | | |
| LSD (P = .05) | | | | 0.070 | 1.460 | 0.0172 | 0.3756 | 0.0744 | 2.1867 | 0.0447 | 0.9342 |
| Std Deviation | | | | 0.051 | 1.060 | 0.0125 | 0.2726 | 0.0540 | 1.5867 | 0.0324 | 0.6779 |
| CV | | | | 9.47 | 14.44 | 16.22 | 25.54 | 4.2 | 9.05 | 7.77 | 11.99 |

Example 35

Introduction

Trial to evaluate combinations of Compound 1+Sunny+Lontrel, in thebaine crop. Sprays were applied on 9 November, with crop at ground cover, and capsules were harvested on 18 February.

TABLE 35a

Effect of treatments on yield parameters.

| Trt No. | Treatment Name | Rate | Rate Unit | Grow Stg | CAPSULE/SEED RATIO | STRAW kg/ha | SEED kg/ha | YIELD t/ha |
|---|---|---|---|---|---|---|---|---|
| 1 | LONTREL | 1 | L/HA | GC | 12.193 a | 1627 a | 113 bc | 1.74 ab |
| 2 | LONTREL | 1 | L/HA | GC | 12.136 a | 1496 a | 91 c | 1.59 b |
| 2 | COMPOUND 1 | 1 | L/HA | GC | | | | |
| 3 | LONTREL | 1 | L/HA | GC | 5.607 b | 1622 a | 206 a | 1.83 a |
| 3 | SUNNY | 1 | L/HA | GC | | | | |
| 3 | CODACIDE OIL | 1 | L/HA | GC | | | | |
| 4 | LONTREL | 1 | L/HA | GC | 8.232 ab | 1573 a | 163 ab | 1.73 ab |
| 4 | COMPOUND 1 | 1 | L/HA | GC | | | | |
| 4 | SUNNY | 1 | L/HA | GC | | | | |
| 4 | CODACIDE OIL | 1 | L/HA | GC | | | | |
| 5 | LONTREL | 1 | L/HA | GC | 8.320 ab | 1611 a | 139 bc | 1.75 ab |
| 5 | COMPOUND 1 | .5 | L/HA | GC | | | | |
| 5 | SUNNY | 1 | L/HA | GC | | | | |

TABLE 35a-continued

Effect of treatments on yield parameters.

| Trt No. | Treatment Name | Rate | Rate Unit | Grow Stg | CAPSULE/ SEED RATIO | STRAW kg/ha | SEED kg/ha | YIELD t/ha |
|---|---|---|---|---|---|---|---|---|
| 5 | CODACIDE OIL | 1 | L/HA | GC | | | | |
| LSD (P = .05) | | | | | 3.9376 | 138.1 | 58.4 | 0.184 |
| Standard Deviation | | | | | 2.8573 | 100.2 | 42.4 | 0.134 |
| CV | | | | | 30.73 | 6.32 | 29.8 | 7.75 |

TABLE 35b

Effect of treatments on alkaloid parameters.

| Trt No. | Treatment Name | Rate | Rate Unit | STRAW MORPHINE % | MORPHINE kg/ha | STRAW CODEINE % | CODEINE kg/ha | STRAW THEBAINE % | THEBAINE kg/ha | STRAW O'PAVIN % | ORIPAVINE kg/ha |
|---|---|---|---|---|---|---|---|---|---|---|---|
| 1 | LONTREL | 1 | L/HA | 0.70 b | 11.39 b | 0.161 a | 2.60 a | 1.23 e | 19.89 b | 0.208 e | 3.40 d |
| 2 | LONTREL | 1 | L/HA | 0.25 e | 3.76 e | 0.073 d | 1.08 d | 1.72 b | 25.69 a | 0.346 c | 5.22 b |
| 2 | COMPOUND 1 | 1 | L/HA | | | | | | | | |
| 3 | LONTREL | 1 | L/HA | 0.79 a | 12.80 a | 0.148 b | 2.40 b | 1.31 d | 21.34 b | 0.269 d | 4.38 c |
| 3 | SUNNY | 1 | L/HA | | | | | | | | |
| 3 | CODACIDE | 1 | L/HA | | | | | | | | |
| 4 | LONTREL | 1 | L/HA | 0.28 d | 4.40 d | 0.063 e | 0.97 e | 1.79 a | 28.19 a | 0.415 a | 6.53 a |
| 4 | COMPOUND 1 | 1 | L/HA | | | | | | | | |
| 4 | SUNNY | 1 | L/HA | | | | | | | | |
| 4 | CODACIDE | 1 | L/HA | | | | | | | | |
| 5 | LONTREL | 1 | L/HA | 0.36 c | 5.90 c | 0.082 c | 1.30 c | 1.70 c | 27.34 a | 0.400 b | 6.50 a |
| 5 | COMPOUND 1 | .5 | L/HA | | | | | | | | |
| 5 | SUNNY | 1 | L/HA | | | | | | | | |
| 5 | CODACIDE | 1 | L/HA | | | | | | | | |
| LSD (P = .05) | | | | 0.000 | 0.000 | 0.0000 | 0.0000 | 0.0000 | 2.7613 | 0.0000 | 0.7740 |
| Standard Deviation | | | | 0.000 | 0.000 | 0.0000 | 0.0000 | 0.0000 | 2.0037 | 0.0000 | 0.5616 |
| CV | | | | 0.0 | 0.0 | 0.0 | 0.0 | 0.0 | 8.18 | 0.0 | 10.79 |

Example 36

Introduction

Trial to evaluate split applications of Compound 1+Sunny, in Lontrel-treated thebaine crop. Sprays were applied on 3, 9 and 25 November, with crop at row cover, ground cover and late run-up, respectively. Capsules were harvested on 17 February.

Pulse™ is an adjuvant manufactured by Monsanto which contains 1000 g/L modified poly-dimethyl siloxane.

TABLE 36a

Effect of treatments on yield parameters.

| Trt No. | Treatment Name | Rate | Rate Unit | Grow Stg | CAPSULE/ SEED RATIO | STRAW kg/ha | SEED kg/ha | YIELD t/ha |
|---|---|---|---|---|---|---|---|---|
| 1 | NIL | | | | 4.582 a | 1786 ab | 290 c | 2.07 c |
| 2 | SUNNY | .5 | L/HA | GC | 2.111 b | 1801 ab | 602 a | 2.40 abc |
| 2 | COMPOUND 1 | .5 | L/HA | GC | | | | |
| 2 | PULSE | .2 | % V/V | GC | | | | |
| 2 | SUNNY | .5 | L/HA | LRU | | | | |
| 2 | COMPOUND 1 | .5 | L/HA | LRU | | | | |
| 2 | PULSE | .2 | % V/V | LRU | | | | |
| 3 | SUNNY | .5 | L/HA | RC | 2.715 b | 1739 b | 447 b | 2.19 bc |
| 3 | COMPOUND 1 | .5 | L/HA | RC | | | | |
| 3 | PULSE | .2 | % V/V | RC | | | | |
| 3 | SUNNY | .5 | L/HA | LRU | | | | |
| 3 | COMPOUND 1 | .5 | L/HA | LRU | | | | |
| 3 | PULSE | .2 | % V/V | LRU | | | | |
| 4 | COMPOUND 1 | .5 | L/HA | RC | 2.034 b | 1815 ab | 625 a | 2.44 ab |
| 4 | SUNNY | .5 | L/HA | GC | | | | |
| 4 | PULSE | .2 | % V/V | GC | | | | |

TABLE 36a-continued

Effect of treatments on yield parameters.

| Trt No. | Treatment Name | Rate | Rate Unit | Grow Stg | CAPSULE/ SEED RATIO | STRAW kg/ha | SEED kg/ha | YIELD t/ha |
|---|---|---|---|---|---|---|---|---|
| 4 | SUNNY | .5 | L/HA | LRU | | | | |
| 4 | COMPOUND 1 | .5 | L/HA | LRU | | | | |
| 4 | PULSE | .2 | % V/V | LRU | | | | |
| 5 | TREATMENT 5 | | | | 2.227 b | 2071 a | 645 a | 2.72 a |
| LSD (P = .05) | | | | | 0.8096 | 268.8 | 105.6 | 0.324 |
| Standard Deviation | | | | | 0.5875 | 195.1 | 76.6 | 0.235 |
| CV | | | | | 21.49 | 10.59 | 14.69 | 9.95 |

TABLE 36b

Effect of treatments on alkaloid parameters.

| Trt No. | Treatment Name | Rate | Grow Stg | STRAW MORPHINE % | MORPHINE kg/ha | STRAW CODEINE % | CODEINE kg/ha | STRAW THEBAINE % | THEBAINE kg/ha | STRAW O'PAVIN % | ORIPAVINE kg/ha |
|---|---|---|---|---|---|---|---|---|---|---|---|
| 1 | NIL | | | 0.67 a | 11.97 a | 0.124 a | 2.19 a | 1.216 b | 21.73 b | 0.267 c | 4.81 c |
| 2 | SUNNY | .5 | GC | 0.19 c | 3.36 c | 0.049 b | 0.89 c | 1.839 a | 33.11 a | 0.424 b | 7.65 b |
| 2 | COMPOUND 1 | .5 | GC | | | | | | | | |
| 2 | PULSE | .2 | GC | | | | | | | | |
| 2 | SUNNY | .5 | LRU | | | | | | | | |
| 2 | COMPOUND 1 | .5 | LRU | | | | | | | | |
| 2 | PULSE | .2 | LRU | | | | | | | | |
| 3 | SUNNY | .5 | RC | 0.19 bc | 3.33 c | 0.051 b | 0.88 c | 1.790 a | 31.13 a | 0.393 b | 6.83 b |
| 3 | COMPOUND 1 | .5 | RC | | | | | | | | |
| 3 | PULSE | .2 | RC | | | | | | | | |
| 3 | SUNNY | .5 | LRU | | | | | | | | |
| 3 | COMPOUND 1 | .5 | LRU | | | | | | | | |
| 3 | PULSE | .2 | LRU | | | | | | | | |
| 4 | COMPOUND 1 | .5 | RC | 0.23 bc | 4.07 bc | 0.054 b | 0.97 bc | 1.820 a | 32.91 a | 0.422 b | 7.72 b |
| 4 | SUNNY | .5 | GC | | | | | | | | |
| 4 | PULSE | .2 | GC | | | | | | | | |
| 4 | SUNNY | .5 | LRU | | | | | | | | |
| 4 | COMPOUND 1 | .5 | LRU | | | | | | | | |
| 4 | PULSE | .2 | LRU | | | | | | | | |
| 5 | TREATMENT 5 | | | 0.24 b | 5.00 b | 0.051 b | 1.05 b | 1.773 a | 36.79 a | 0.467 a | 9.67 a |
| LSD (P = .05) | | | | 0.050 | 0.997 | 0.0075 | 0.130 | 0.0979 | 5.479 | 0.0343 | 1.411 |
| Standard Deviation | | | | 0.036 | 0.723 | 0.0055 | 0.094 | 0.0711 | 3.975 | 0.0249 | 1.024 |
| CV | | | | 11.91 | 13.04 | 8.32 | 7.88 | 4.21 | 12.77 | 6.31 | 13.96 |

Example 37

Introduction

Trial to evaluate combinations of methyl jasmonate with Compound 1 in Lontrel-treated thebaine crop. Sprays were applied on 4, 17 and 29 November, 3 and 6 December, with crop at row cover, early run-up, late run-up, bud-emergence and early hook stages, respectively. Lontrel (0.9 L/ha) was applied to all plots on 10 November. Capsules were harvested on 12 February.

TABLE 37a

Effect of treatments on yield parameters.

| Trt No. | Treatment Name | Rate | Rate Unit | Grow Stg | CAPSULE/ SEED RATIO | STRAW kg/ha | SEED kg/ha | YIELD t/ha |
|---|---|---|---|---|---|---|---|---|
| 1 | NIL | | | | 1.403 ab | 2280 a | 1154 ab | 3.43 a |
| 2 | COMPOUND 1 | .33 | L/HA | ERU | 1.495 a | 2168 a | 1053 b | 3.22 a |
| 2 | COMPOUND 1 | .33 | L/HA | BE | | | | |
| 2 | COMPOUND 1 | .33 | L/HA | EHOOK | | | | |
| 3 | COMPOUND 1 | .33 | L/HA | ERU | 0.946 b | 1893 a | 1399 a | 3.29 a |
| 3 | METHYL JASMONATE | .33 | L/HA | ERU | | | | |
| 3 | ACTIVATOR | .065 | % V/V | ERU | | | | |

TABLE 37a-continued

Effect of treatments on yield parameters.

| Trt No. | Treatment Name | Rate | Rate Unit | Grow Stg | CAPSULE/ SEED RATIO | STRAW kg/ha | SEED kg/ha | YIELD t/ha |
|---|---|---|---|---|---|---|---|---|
| 3 | COMPOUND 1 | .33 | L/HA | BE | | | | |
| 3 | METHYL JASMONATE | .33 | L/HA | BE | | | | |
| 3 | ACTIVATOR | .065 | % V/V | BE | | | | |
| 3 | COMPOUND 1 | .33 | L/HA | EHOOK | | | | |
| 3 | METHYL JASMONATE | .33 | L/HA | EHOOK | | | | |
| 3 | ACTIVATOR | .065 | % V/V | EHOOK | | | | |
| 4 | COMPOUND 1 | .5 | L/HA | RC | 1.106 ab | 1990 a | 1256 ab | 3.24 a |
| 4 | COMPOUND 1 | .5 | L/HA | LRU | | | | |
| 5 | COMPOUND 1 | .5 | L/HA | RC | 1.074 ab | 2199 a | 1419 a | 3.62 a |
| 5 | COMPOUND 1 | .5 | L/HA | LRU | | | | |
| 5 | METHYL JASMONATE | .5 | L/HA | LRU | | | | |
| 5 | ACTIVATOR | .125 | % V/V | LRU | | | | |
| 5 | METHYL JASMONATE | .5 | L/HA | EHOOK | | | | |
| 5 | ACTIVATOR | .125 | % V/V | EHOOK | | | | |
| LSD (P = .05) | | | | | 0.4656 | 408.0 | 286.2 | 0.512 |
| Standard Deviation | | | | | 0.3192 | 279.7 | 196.2 | 0.351 |
| CV | | | | | 26.5 | 13.28 | 15.62 | 10.45 |

TABLE 37b

Effect of treatments on alkaloid parameters.

| Trt No. | Treatment Name | Rate | Grow Stg | STRAW MORPHINE % | MOR- PHINE kg/ha | STRAW CODEINE % | CODEINE kg/ha | STRAW THEBAINE % | THEBAINE kg/ha | STRAW O'PAVIN % | ORIPAVINE kg/ha |
|---|---|---|---|---|---|---|---|---|---|---|---|
| 1 | NIL | | | 0.89 a | 21.20 a | 0.09 a | 2.10 a | 1.03 c | 23.87 c | 0.32 c | 7.39 b |
| 2 | COMPOUND 1 | .33 | ERU | 0.38 bc | 8.50 b | 0.04 c | 0.84 b | 1.83 a | 39.82 a | 0.58 a | 12.68 a |
| 2 | COMPOUND 1 | .33 | BE | | | | | | | | |
| 2 | COMPOUND 1 | .33 | EHOOK | | | | | | | | |
| 3 | COMPOUND 1 | .33 | ERU | 0.35 c | 6.84 b | 0.04 c | 0.69 b | 1.92 a | 36.22 ab | 0.64 a | 12.15 a |
| 3 | METH JAS | .33 | ERU | | | | | | | | |
| 3 | ACTIVATOR | .065 | ERU | | | | | | | | |
| 3 | COMPOUND 1 | .33 | BE | | | | | | | | |
| 3 | METH JAS | .33 | BE | | | | | | | | |
| 3 | ACTIVATOR | .065 | BE | | | | | | | | |
| 3 | COMPOUND 1 | .33 | EHOOK | | | | | | | | |
| 3 | METH JAS | .33 | EHOOK | | | | | | | | |
| 3 | ACTIVATOR | .065 | EHOOK | | | | | | | | |
| 4 | COMPOUND 1 | .5 | RC | 0.65 ab | 5.94 b | 0.06 b | 0.63 b | 1.56 b | 32.54 b | 0.48 b | 12.33 a |
| 4 | COMPOUND 1 | .5 | LRU | | | | | | | | |
| 5 | COMPOUND 1 | .5 | RC | 0.45 bc | 10.72 b | 0.05 bc | 1.05 b | 1.87 a | 40.35 a | 0.66 a | 14.18 a |
| 5 | COMPOUND 1 | .5 | LRU | | | | | | | | |
| 5 | METH JAS | .5 | LRU | | | | | | | | |
| 5 | ACTIVATOR | .125 | LRU | | | | | | | | |
| 5 | METH JAS | .5 | EHOOK | | | | | | | | |
| 5 | ACTIVATOR | .125 | EHOOK | | | | | | | | |
| LSD (P = .05) | | | | 0.264 | 7.292 | 0.015 | 0.571 | 0.135 | 6.149 | 0.090 | 2.018 |
| Standard Deviation | | | | 0.190 | 4.875 | 0.011 | 0.382 | 0.097 | 4.111 | 0.065 | 1.349 |
| CV | | | | 34.92 | 45.82 | 19.64 | 36.0 | 5.91 | 11.89 | 12.03 | 11.49 |

Example 38

Introduction

Trial to evaluate combinations of methyl jasmonate with Compound 1 in Lontrel-treated thebaine crop. Sprays were applied on 4, 17 and 26 November, 3 and 6 December, with crop at row cover, early run-up, late run-up, hook and early flowering stages, respectively. Lontrel (0.9 L/ha) was applied to all plots on 10 November. Capsules were harvested on 17 February.

TABLE 38a

Effect of treatments on yield parameters.

| Trt No. | Treatment Name | Rate | Rate Unit | Grow Stg | CAPSULE/ SEED RATIO | STRAW kg/ha | SEED kg/ha | YIELD t/ha |
|---|---|---|---|---|---|---|---|---|
| 1 | NIL | | | | 3.450 c | 1540 a | 315 a | 1.86 a |
| 2 | COMPOUND 1 | .33 | L/HA | ERU | 6.587 a | 1279 b | 146 c | 1.43 b |
| 2 | COMPOUND 1 | .33 | L/HA | HOOK | | | | |
| 2 | COMPOUND 1 | .33 | L/HA | EF | | | | |
| 3 | COMPOUND 1 | .33 | L/HA | ERU | 2.744 c | 1294 b | 331 a | 1.63 ab |
| 3 | METHYL JASMONATE | .33 | L/HA | ERU | | | | |
| 3 | ACTIVATOR | .065 | % V/V | ERU | | | | |
| 3 | COMPOUND 1 | .33 | L/HA | HOOK | | | | |
| 3 | METHYL JASMONATE | .33 | L/HA | HOOK | | | | |
| 3 | ACTIVATOR | .065 | % V/V | HOOK | | | | |
| 3 | COMPOUND 1 | .33 | L/HA | EF | | | | |
| 3 | METHYL JASMONATE | .33 | L/HA | EF | | | | |
| 3 | ACTIVATOR | .065 | % V/V | EF | | | | |
| 4 | COMPOUND 1 | .5 | L/HA | RC | 4.907 b | 1543 a | 236 b | 1.78 a |
| 4 | COMPOUND 1 | .5 | L/HA | LRU | | | | |
| 5 | COMPOUND 1 | .5 | L/HA | RC | 2.940 c | 1212 b | 289 ab | 1.50 b |
| 5 | COMPOUND 1 | .5 | L/HA | LRU | | | | |
| 5 | METHYL JASMONATE | .5 | L/HA | LRU | | | | |
| 5 | ACTIVATOR | .065 | % V/V | LRU | | | | |
| 5 | METHYL JASMONATE | .5 | L/HA | EF | | | | |
| 5 | ACTIVATOR | .125 | % V/V | EF | | | | |
| LSD (P = .05) | | | | | 1.3348 | 178.2 | 61.9 | 0.220 |
| Standard Deviation | | | | | 0.9686 | 129.3 | 44.9 | 0.160 |
| CV | | | | | 23.48 | 9.42 | 17.07 | 9.76 |

TABLE 38b

Effect of treatments on alkaloid parameters.

| Trt No. | Treatment Name | Rate | Grow Stg | STRAW MORPHINE % | MORPHINE kg/ha | STRAW CODEINE % | CODEINE kg/ha | STRAW THEBAINE % | THEBAINE kg/ha | STRAW O'PAVIN % | ORIPAVINE kg/ha |
|---|---|---|---|---|---|---|---|---|---|---|---|
| 1 | NIL | | | 0.71 a | 10.87 a | 0.14 a | 2.11 a | 1.33 d | 20.50 b | 0.27 d | 4.12 bc |
| 2 | COMPOUND 1 | .33 | ERU | 0.11 c | 1.36 d | 0.04 bc | 0.54 cd | 2.14 b | 27.26 a | 0.31 c | 3.97 c |
| 2 | COMPOUND 1 | .33 | HOOK | | | | | | | | |
| 2 | COMPOUND 1 | .33 | EF | | | | | | | | |
| 3 | COMPOUND 1 | .33 | ERU | 0.12 c | 1.60 cd | 0.04 c | 0.45 d | 2.29 a | 29.31 a | 0.37 ab | 4.81 ab |
| 3 | METH JAS | .33 | ERU | | | | | | | | |
| 3 | ACTIVATOR | .065 | ERU | | | | | | | | |
| 3 | COMPOUND 1 | .33 | HOOK | | | | | | | | |
| 3 | METH JAS | .33 | HOOK | | | | | | | | |
| 3 | ACTIVATOR | .065 | HOOK | | | | | | | | |
| 3 | COMPOUND 1 | .33 | EF | | | | | | | | |
| 3 | METH JAS | .33 | EF | | | | | | | | |
| 3 | ACTIVATOR | .065 | EF | | | | | | | | |
| 4 | COMPOUND 1 | .5 | RC | 0.17 b | 2.63 b | 0.05 b | 0.72 b | 1.91 c | 29.42 a | 0.35 b | 5.48 a |
| 4 | COMPOUND 1 | .5 | LRU | | | | | | | | |
| 5 | COMPOUND 1 | .5 | RC | 0.17 b | 2.05 c | 0.05 b | 0.58 c | 2.15 b | 25.93 a | 0.40 a | 4.82 ab |
| 5 | COMPOUND 1 | .5 | LRU | | | | | | | | |
| 5 | METH JAS | .5 | LRU | | | | | | | | |
| 5 | ACTIVATOR | .065 | LRU | | | | | | | | |
| 5 | METH JAS | .5 | EF | | | | | | | | |
| 5 | ACTIVATOR | .125 | EF | | | | | | | | |
| LSD (P = .05) | | | | 0.025 | 0.472 | 0.010 | 0.099 | 0.103 | 3.374 | 0.023 | 0.784 |
| Standard Deviation | | | | 0.018 | 0.343 | 0.007 | 0.072 | 0.075 | 2.448 | 0.017 | 0.569 |
| CV | | | | 6.95 | 9.25 | 11.09 | 8.15 | 3.8 | 9.24 | 4.96 | 12.27 |

Example 39

Introduction

Trial to evaluate combinations of methyl jasmonate with Compound 1 in Lontrel-treated thebaine crop. Sprays were applied on 15, 22 and 26 November, 2 and 6 December, with crop at ground cover, early run-up, mid-late run-up, bud-emergence and hook stages, respectively. Lontrel (0.8 L/ha) was applied to all plots on 15 November. Capsules were harvested on 10 February.

TABLE 39a

Effect of treatments on yield parameters.

| Trt No. | Treatment Name | Rate | Rate Unit | Grow Stg | CAPSULE/ SEED RATIO | STRAW kg/ha | SEED kg/ha | YIELD t/ha |
|---|---|---|---|---|---|---|---|---|
| 1 | NIL | | | | 2.791 b | 1420 ab | 377 a | 1.80 ab |
| 2 | COMPOUND 1 | .33 | L/HA | ERU | 4.532 a | 1364 b | 223 b | 1.59 c |
| 2 | COMPOUND 1 | .33 | L/HA | BE | | | | |
| 2 | COMPOUND 1 | .33 | L/HA | HOOK | | | | |
| 3 | COMPOUND 1 | .33 | L/HA | ERU | 2.428 b | 1495 a | 437 a | 1.93 a |
| 3 | METHYL JASMONATE | .33 | L/HA | ERU | | | | |
| 3 | COMPOUND 1 | .33 | L/HA | BE | | | | |
| 3 | METHYL JASMONATE | .33 | L/HA | BE | | | | |
| 3 | COMPOUND 1 | .33 | L/HA | HOOK | | | | |
| 3 | METHYL JASMONATE | .33 | L/HA | HOOK | | | | |
| 4 | COMPOUND 1 | .5 | L/HA | GC | 4.051 a | 1381 ab | 241 b | 1.62 bc |
| 4 | COMPOUND 1 | .5 | L/HA | M-LRU | | | | |
| 5 | COMPOUND 1 | .5 | L/HA | GC | 2.991 b | 1372 ab | 350 a | 1.72 bc |
| 5 | COMPOUND 1 | .5 | L/HA | M-LRU | | | | |
| 5 | METHYL JASMONATE | .5 | L/HA | M-LRU | | | | |
| 5 | METHYL JASMONATE | .5 | L/HA | HOOK | | | | |
| LSD (P = .05) | | | | | 0.9901 | 116.3 | 97.4 | 0.184 |
| Standard Deviation | | | | | 0.7185 | 84.4 | 70.7 | 0.134 |
| CV | | | | | 21.39 | 6.0 | 21.72 | 7.71 |

TABLE 39b

Effect of treatments on alkaloid parameters.

| Trt No. | Treatment Name | Rate | Grow Stg | STRAW MORPHINE % | MORPHINE kg/ha | STRAW CODEINE % | CODEINE kg/ha | STRAW THEBAINE % | THEBAINE kg/ha | STRAW O'PAVIN % | ORIPAVINE kg/ha |
|---|---|---|---|---|---|---|---|---|---|---|---|
| 1 | NIL | | | 0.65 a | 8.80 a | 0.104 a | 1.45 a | 1.29 c | 16.83 c | 0.34 a | 4.50 a |
| 2 | COMPOUND 1 | .33 | ERU | 0.13 c | 1.71 b | 0.024 b | 0.31 b | 1.88 a | 25.74 ab | 0.36 a | 4.95 a |
| 2 | COMPOUND 1 | .33 | BE | | | | | | | | |
| 2 | COMPOUND 1 | .33 | HOOK | | | | | | | | |
| 3 | COMPOUND 1 | .33 | ERU | 0.13 c | 2.00 b | 0.024 b | 0.35 b | 1.90 a | 28.38 a | 0.36 a | 5.37 a |
| 3 | METH JAS | .33 | ERU | | | | | | | | |
| 3 | COMPOUND 1 | .33 | BE | | | | | | | | |
| 3 | METH JAS | .33 | BE | | | | | | | | |
| 3 | COMPOUND 1 | .33 | HOOK | | | | | | | | |
| 3 | METH JAS | .33 | HOOK | | | | | | | | |
| 4 | COMPOUND 1 | .5 | GC | 0.16 bc | 2.17 b | 0.028 b | 0.38 b | 1.74 b | 24.08 b | 0.37 a | 5.14 a |
| 4 | COMPOUND 1 | .5 | M-LRU | | | | | | | | |
| 5 | COMPOUND 1 | .5 | GC | 0.19 b | 2.44 b | 0.032 b | 0.42 b | 1.88 a | 25.65 ab | 0.38 a | 5.17 a |
| 5 | COMPOUND 1 | .5 | M-LRU | | | | | | | | |
| 5 | METH JAS | .5 | M-LRU | | | | | | | | |
| 5 | METH JAS | .5 | HOOK | | | | | | | | |
| LSD (P = .05) | | | | 0.032 | 0.852 | 0.0178 | 0.341 | 0.062 | 3.555 | 0.045 | 0.818 |
| Standard Deviation | | | | 0.023 | 0.605 | 0.0127 | 0.242 | 0.044 | 2.523 | 0.032 | 0.581 |
| CV | | | | 9.0 | 17.65 | 29.95 | 41.61 | 2.51 | 10.45 | 8.86 | 11.6 |

Example 40

Introduction

Trial to evaluate sequential applications of methyl jasmonate in Lontrel-treated thebaine crop. Sprays were applied on 16, 22 and 26 November, 2 and 6 December, with crop at ground cover, early run-up, mid-late run-up, late bud-emergence and hook stages, respectively. Capsules were harvested on 1 February.

TABLE 40a

Effect of treatments on yield parameters.

| Trt No. | Treatment Name | Rate | Rate Unit | Grow Stg | CAPSULE/ SEED RATIO | STRAW kg/ha | SEED kg/ha | YIELD t/ha |
|---|---|---|---|---|---|---|---|---|
| 1 | LONTREL | .8 | L/HA | GC | 18.226 a | 1157 a | 48 a | 1.20 a |
| 2 | LONTREL | .8 | L/HA | GC | 17.385 a | 1116 a | 49 a | 1.16 a |

TABLE 40a-continued

Effect of treatments on yield parameters.

| Trt No. | Treatment Name | Rate | Rate Unit | Grow Stg | CAPSULE/ SEED RATIO | STRAW kg/ha | SEED kg/ha | YIELD t/ha |
|---|---|---|---|---|---|---|---|---|
| 2 | METHYL JASMONATE | .05 | L/HA | GC | | | | |
| 2 | ACTIVATOR | .125 | % V/V | GC | | | | |
| 2 | METHYL JASMONATE | .05 | L/HA | ERU | | | | |
| 2 | ACTIVATOR | .125 | % V/V | ERU | | | | |
| 2 | METHYL JASMONATE | .05 | L/HA | M-LRU | | | | |
| 2 | ACTIVATOR | .125 | % V/V | M-LRU | | | | |
| 2 | METHYL JASMONATE | .05 | L/HA | LBE | | | | |
| 2 | ACTIVATOR | .125 | % V/V | LBE | | | | |
| 2 | METHYL JASMONATE | .05 | L/HA | HOOK | | | | |
| 2 | ACTIVATOR | .125 | % V/V | HOOK | | | | |
| 3 | LONTREL | .8 | L/HA | GC | 14.718 a | 1016 b | 50 a | 1.07 b |
| 3 | METHYL JASMONATE | .1 | L/HA | GC | | | | |
| 3 | ACTIVATOR | .125 | % V/V | GC | | | | |
| 3 | METHYL JASMONATE | .1 | L/HA | ERU | | | | |
| 3 | ACTIVATOR | .125 | % V/V | ERU | | | | |
| 3 | METHYL JASMONATE | .1 | L/HA | M-LRU | | | | |
| 3 | ACTIVATOR | .125 | % V/V | M-LRU | | | | |
| 3 | METHYL JASMONATE | .1 | L/HA | BE | | | | |
| 3 | ACTIVATOR | .125 | % V/V | BE | | | | |
| 3 | METHYL JASMONATE | .1 | L/HA | HOOK | | | | |
| 3 | ACTIVATOR | .125 | % V/V | HOOK | | | | |
| 4 | TREATMENT 4 | | | | 11.449 ab | 200 c | 13 b | 0.21 c |
| 5 | TREATMENT 5 | | | | 5.772 b | 270 c | 33 a | 0.30 c |
| LSD (P = .05) | | | | | 6.4109 | 87.6 | 16.9 | 0.094 |
| Standard Deviation | | | | | 4.6519 | 63.6 | 12.3 | 0.068 |
| CV | | | | | 34.43 | 8.45 | 31.85 | 8.63 |

TABLE 40b

Effect of treatments on alkaloid parameters.

| Trt No. | Treatment Name | Rate | Grow Stg | STRAW MORPHINE % | MORPHINE kg/ha | STRAW CODEINE % | CODEINE kg/ha | STRAW THEBAINE % | THEBAINE kg/ha | STRAW O'PAVIN % | ORIPAVINE kg/ha |
|---|---|---|---|---|---|---|---|---|---|---|---|
| 1 | LONTREL | .8 | GC | 0.70 a | 8.10 a | 0.13 a | 1.45 a | 1.48 c | 17.09 c | 0.42 c | 4.82 c |
| 2 | LONTREL | .8 | GC | 0.52 b | 5.81 b | 0.07 b | 0.73 b | 1.86 b | 20.75 a | 0.58 a | 6.45 a |
| 2 | METH JAS | .05 | GC | | | | | | | | |
| 2 | ACTIVATOR | .125 | GC | | | | | | | | |
| 2 | METH JAS | .05 | ERU | | | | | | | | |
| 2 | ACTIVATOR | .125 | ERU | | | | | | | | |
| 2 | METH JAS | .05 | M-LRU | | | | | | | | |
| 2 | ACTIVATOR | .125 | M-LRU | | | | | | | | |
| 2 | METH JAS | .05 | LBE | | | | | | | | |
| 2 | ACTIVATOR | .125 | LBE | | | | | | | | |
| 2 | METH JAS | .05 | HOOK | | | | | | | | |
| 2 | ACTIVATOR | .125 | HOOK | | | | | | | | |
| 3 | LONTREL | .8 | GC | 0.55 b | 5.61 b | 0.07 b | 0.74 b | 1.85 b | 18.77 b | 0.56 a | 5.73 b |
| 3 | METH JAS | .1 | GC | | | | | | | | |
| 3 | ACTIVATOR | .125 | GC | | | | | | | | |
| 3 | METH JAS | .1 | ERU | | | | | | | | |
| 3 | ACTIVATOR | .125 | ERU | | | | | | | | |
| 3 | METH JAS | .1 | M-LRU | | | | | | | | |
| 3 | ACTIVATOR | .125 | M-LRU | | | | | | | | |
| 3 | METH JAS | .1 | LBE | | | | | | | | |
| 3 | ACTIVATOR | .125 | LBE | | | | | | | | |
| 3 | METH JAS | .1 | HOOK | | | | | | | | |
| 3 | ACTIVATOR | .125 | HOOK | | | | | | | | |
| 4 | TRT 4 | .5 | GC | 0.24 c | 0.53 c | 0.04 c | 0.08 c | 2.27 a | 5.13 d | 0.53 ab | 1.18 d |
| 5 | TRT 5 | .5 | GC | 0.21 c | 0.58 c | 0.05 c | 0.13 c | 2.25 a | 6.06 d | 0.50 b | 1.33 d |
| LSD (P = .05) | | | | 0.051 | 0.668 | 0.020 | 0.236 | 0.129 | 1.363 | 0.051 | 0.481 |
| Standard Deviation | | | | 0.037 | 0.480 | 0.014 | 0.169 | 0.093 | 0.979 | 0.037 | 0.346 |
| CV | | | | 8.25 | 11.63 | 20.22 | 27.01 | 4.78 | 7.22 | 7.07 | 8.85 |

The invention claimed is:

1. A method of decreasing the proportion of morphine and increasing the proportion of thebaine and/or oripavine in a poppy plant comprising the step of applying an effective amount of an acylcyclohexanedione compound or agriculturally acceptable salt thereof of Formula (II)

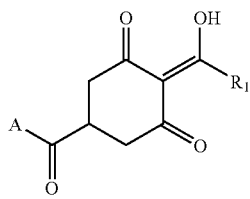

(II)

wherein $R_1$ is optionally substituted alkyl or optionally substituted aryl; and A is $OR_2$ or $NR_3R_4$ wherein $R_2$ is selected from the group consisting of hydrogen, optionally substituted alkyl, optionally substituted alkenyl, optionally substituted alkynyl and optionally substituted aryl; and $R_3$ and $R_4$ are independently selected from hydrogen, optionally substituted alkyl, optionally substituted alkenyl, optionally substituted alkynyl and optionally substituted aryl; or one of $R_3$ or $R_4$ is alkoxy and the other as defined above or $R_3$ and $R_4$ together with the nitrogen atom to which they are attached form a 5- or 6-membered heterocyclic ring which may contain an additional oxygen or sulfur atom;

to said poppy plant or locus thereof.

2. The method according to claim 1 wherein said acylcyclohexanedione compound is a compound of Formula (I):

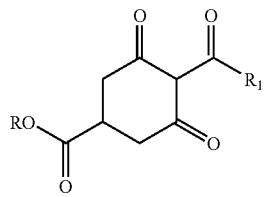

(I)

wherein R is selected from the group consisting of hydrogen, optionally substituted alkyl optionally substituted alkenyl, optionally substituted alkynyl and optionally substituted aryl; and $R_1$ is optionally substituted alkyl or optionally substituted aryl;

or an agriculturally acceptable salt or ester thereof.

3. The method according to claim 1 wherein said acylcyclohexanedione compound or agriculturally acceptable salt thereof is selected from the group consisting of trinexapac-ethyl and prohexadione-calcium.

4. The method according to claim 1 wherein said acylcyclohexanedione compound is trinexapac-ethyl.

5. The method according to claim 2, wherein the acylcyclohexanedione compound is prohexadione-calcium.

6. The method according to claim 1 wherein the composition further comprises clopyralid.

7. The method according to claim 1 when the composition further comprises at least one fungicide.

8. The method according to claim 1 wherein the composition is applied to either a morphine variety or thebaine variety.

* * * * *